(12) United States Patent
Cox et al.

(10) Patent No.: US 11,878,961 B2
(45) Date of Patent: Jan. 23, 2024

(54) NEXT GENERATION FKBP52 TARGETING DRUGS FOR THE TREATMENT OF PROSTATE AND BREAST CANCER

(71) Applicants: Board of Regents, The University of Texas System, Austin, TX (US); The University of British Columbia, Vancouver (CA)

(72) Inventors: Marc Cox, El Paso, TX (US); Artem Cherkasov, Vancouver (CA); Fuqiang Ban, Vancouver (CA)

(73) Assignees: Board of Regents, The University of Texas System, Austin, TX (US); The University of British Columbia, Vancouver (CA)

( * ) Notice: Subject to any disclaimer, the term of this patent is extended or adjusted under 35 U.S.C. 154(b) by 104 days.

(21) Appl. No.: 17/153,340

(22) Filed: Jan. 20, 2021

(65) Prior Publication Data

US 2021/0230125 A1   Jul. 29, 2021

Related U.S. Application Data

(60) Provisional application No. 62/963,873, filed on Jan. 21, 2020.

(51) Int. Cl.
  *C07D 249/08*    (2006.01)
  *A61K 45/06*     (2006.01)
  *A61K 31/4196*   (2006.01)

(52) U.S. Cl.
  CPC ............ *C07D 249/08* (2013.01); *A61K 45/06* (2013.01); *A61K 31/4196* (2013.01)

(58) Field of Classification Search
  CPC ................................................. A61K 31/4196
  See application file for complete search history.

(56) References Cited

U.S. PATENT DOCUMENTS 10,322,113 B2  6/2019  Cox et al.
10,682,339 B2  6/2020  Cox et al.

OTHER PUBLICATIONS

Alam, et al., "3D-QSAR, Docking, ADME/Tox studies on Flavone analogs reveal anticancer activity through Tankyrase inhibition," Scientific Reports 2019,9.
Anderson, "The process of structure-based drug design," Chemistry & biology 2003, 10 (9), 787-797.
Araujo, et al., "Computational studies of TGF-beta Ri (ALK-5) inhibitors: Analysis of the binding interactions between ligand-receptor using 2D and 3D techniques," European Journal of Pharmaceutical Sciences 2013, 49 (4), 542-549.
Awale, et al., "Chemical Space: Big Data Challenge for Molecular Diversity," Chimia 2017, 71 (10), 661-666.
Bonomo, et al., "Promising Tools in Prostate Cancer Research: Selective Non-Steroidal Cytochrome P450 17A1 Inhibitors," Scientific Reports 2016, 6.
Bracher, et al., "Crystal Structures of the Free and Ligand-Bound FK1-FK2 Domain Segment of FKBP52 Reveal a Flexible Inter-Domain Hinge," Journal of Molecular Biology 2013, 425 (22), 4134-4144.
Caballero, 3D-QSAR (CoMFA and CoMSIA) and pharmacophore (GALAHAD) studies on the differential inhibition of aldose reductase by flavonoid compounds. Journal of Molecular Graphics & Modelling 2010, 29 (3), 363-371.
Capecchi, et al., "PubChem and ChEMBL beyond Lipinski," Molecular Informatics 2019, 38 (5).
Cavasotto, et al., "Quantum Chemical Approaches in Structure-Based Virtual Screening and Lead Optimization," Frontiers in Chemistry 2018, 6.
Chatterjee, et al., "ImmtorLig_DB: repertoire of virtually screened small molecules against immune receptors to bolster host immunity," Scientific Reports 2019, 9.
Cheng, et al., "Structure-Based Virtual Screening for Drug Discovery: a Problem-Centric Review," Aaps Journal 2012,14 (1), 133-141.
Cherkasov, et al., "QSAR Modeling: Where Have You Been? Where Are You Going To?," Journal of Medicinal Chemistry 2014, 57 (12), 4977-5010.
Chirico, et al., "Real External Predictivity of QSAR Models: How To Evaluate It? Comparison of Different Validation Criteria and Proposal of Using the Concordance Correlation Coefficient," Journal of Chemical Information and Modeling 2011, 51 (9), 2320-2335.
Cramer, et al., "Comparative molecular field analysis (CoMFA)," 1. Effect of shape on binding of steroids to carrier proteins. Journalof the American Chemical Society 1988, 110 (18), 5959-5967.
De Angelo, et al., "Studies on the Dual Activity of EGFR and HER-2 Inhibitors Using Structure-Based Drug Design Techniques," International journal of molecular sciences 2018, 19 (12), 3728.
De Benedetti, et al., "Computational quantum chemistry and adaptive ligand modeling in mechanistic QSAR," Drug Discovery Today 2010, 15 (19-20), 859-866.
De Leon, et al., "Targeting the regulation of androgen receptor signaling by the heat shock protein 90 cochaperone FKBP52 in prostate cancer cells," Proceedings of the National Academy of Sciences of the United States of America 2011, 108 (29), 11878-11883.
Dey, et al., "A machine learning based intrusion detection scheme for data fusion in mobile clouds involving heterogeneous client networks," Information Fusion 2019, 49, 205-215.
Fang, et al., "3DQSAR and docking studies of flavonoids as potent *Escherichia coli* inhibitors," Scientific Reports 2016, 6.
Feng, et al., "Combined pharmacophore-guided 3D-QSAR, molecular docking and molecular dynamics studies for evodiamine analogs as DNA topoisomerase I inhibitors," Journal of the Taiwan Institute of Chemical Engineers 2017, 78, 81-95.

(Continued)

*Primary Examiner* — Kevin E Weddington
(74) *Attorney, Agent, or Firm* — Yee & Associates, P.C.

(57) ABSTRACT

Procedures for inhibiting hormone receptor activation include administering to a subject in need of hormone receptor inhibition a compound having a chemical structure of a molecule that, when docked in the PPIase pocket, could disrupt proline-rich loop conformation and interactions. Procedures for treating prostate cancer or breast cancer include administering to a subject having prostate cancer or breast cancer a compound having a chemical structure of a molecule that, when docked in the PPIase pocket, could disrupt proline-rich loop conformation and interactions.

21 Claims, 39 Drawing Sheets

(56) References Cited

OTHER PUBLICATIONS

Gaali et al, "Selective inhibitors of the FK506-binding protein 51 by induced fit," Nature Chemical Biology 2015, 11 (1), 33-+.
Gaudio, et al., "Proposition, validation and analysis of QSAR models," Química Nov. 2001, 24 (5), 658-671.
Gopalakrishnan, et al., "Exploration of Pipecolate Sulfonamides as Binders of the FK506-Binding Proteins 51 and 52," Journal of Medicinal Chemistry 2012, 55 (9), 4123-4131.
Gramatica, et al., "Principles of QSAR models validation: internal and external," QSAR & combinatorial science 2007, 26 (5), 694-701.
Guo, et al., "In silico rational design and virtual screening of antioxidant tripeptides based on 3D-QSAR modeling," Journal of Molecular Structure 2019, 1193, 223-230.
Hong, et al., "Elevated FKBP52 expression indicates a poor outcome in patients with breast cancer," Oncology Letters 2017, 14 (5), 5379-5385.
Huang, et al., "QSAR Pharmacophore-based Virtual Screening, CoMFA and CoMSIA Modeling and Molecular Docking towards Identifying Lead Compounds for Breast Cancer ProteaseInhibitors," British Journal of Pharmaceutical Research 2017, 20 (1).
Irwin, et al., "ZINC: A Free Tool to Discover Chemistry for Biology," Journal of Chemical Information and Modeling 2012, 52 (7), 1757-1768.
Kaushik, et al., "Ligand-Based Approach for In-silico Drug Designing," Bioinformatics Techniques for Drug Discovery: Applications for Complex Diseases 2018, 11-19.
Kubinyi, "QSAR and 3D QSAR in drug design Part 2: applications and problems," Drug Discovery Today 1997, 2 (12), 538-546.
Kubinyi, et al., "3D QSAR in Drug Design: vol. 2: Ligand-Protein Interactions and Molecular Similarity," Springer: 1998; vol. 2.
Kumar, et al., "E-pharmacophore modelling, virtual screening, molecular dynamics simulations and in-silico ADME analysis for identification of potential E6 inhibitors against cervical cancer," Journal of Molecular Structure 2019, 1189, 299-306.
Kumar, et al., "Virtual screening strategies: Recent advances in the identification and design of anti-cancer agents," Methods 2015, 71, 64-70.
Langer, et al., "Virtual screening an effective tool for lead structure discovery," Current pharmaceutical design 2001, 7 (7), 509-527.
Leal, et al., "Hologram QSAR Models of a Series of 6-Arylquinazolin-4-Amine Inhibitors of a New Alzheimer's Disease Target: Dual Specificity Tyrosine-Phosphorylation-Regulated Kinase-1A Enzyme," International Journal of Molecular Sciences 2015, 16 (3), 5235-5253.
Li, et al., "Characterization of a New Class of Androgen Receptor Antagonists with Potential Therapeutic Application in Advanced Prostate Cancer," Molecular Cancer Therapeutics 2013, 12 (11), 2425-2435.
Li, et al., "Discovery of Small-Molecule Inhibitors Selectively Targeting the DNA-Binding Domain of the Human Androgen Receptor," J Med Chem 2014, 57 (15), 6458-6467.
Li, et al., "New molecular insights into the tyrosyl-tRNA synthase inhibitors: CoMFA, CoMSIA analyses and molecular docking studies," Scientific Reports 2017, 7.
Li, et al., "Structure of the N-terminal domain of human FKBP52," Acta Crystallographica Section D-Biological Crystallography 2003, 59, 16-22.
Lionta, et al., "Structure-Based Virtual Screening for Drug Discovery: Principles, Applications and Recent Advances," Current Topics in Medicinal Chemistry 2014, 14 (16), 1923-1938.
Llanos, et al., "Computational approach to the history of chemical reactivity: Exploring Reaxys database," Abstracts of Papers of the American Chemical Society 2017, 254.
Mahdi, et al., "Similarity Search Techniques in Exploratory Search: A Review", IEEE-Region-10 Conference (IEEE TENCON), IEEE Reg 10, South Korea, Oct 28-31; Ieee: IEEE Reg 10, South Korea, 2018; pp. 2193-2198.
Maltarollo, et al., "Advanced QSAR Studies on PPAR delta Ligands Related to Metabolic Diseases," Journal of the Brazilian Chemical Society 2012, 23 (1), 85-U421.
Nandy, et al., "Exploring molecular fingerprints of selective PPAR delta agonists through comparative and validated chemometric techniques," Sar and Qsar in Environmental Research 2015, 26 (5), 363-382.
Netzeva, et al., "Current status of methods for defining the applicability domain of (quantitative) structure activity relationships—The report and recommendations of ECVAM Workshop 52," Atla-Alternatives to Laboratory Animals 2005, 33 (2), 155-173.
Nunes, et al., "Chemoface: a Novel Free User-Friendly Interface for Chemometrics," Journal of the Brazilian Chemical Society 2012, 23 (11), 2003-2010.
O'Boyle, et al., "PubChem as a biologics database," Abstracts of Papers of the American Chemical Society 2017, 254.
O'Boyle, et al., "Testing Assumptions and Hypotheses for Rescoring Success in Protein-Ligand Docking," Journal of Chemical Information and Modeling 2009, 49 (8), 1871-1878.
Ou-Yang, et al., "Computational drug discovery," Acta Pharmacologica Sinica 2012, 33 (9), 1131-1140.
Pick, et al., "Structure-activity relationships of flavonoids as inhibitors of breast cancer resistance protein (BCRP)," Bioorg. Med. Chem. 2011, 19 (6), 2090-2102.
Saikia, et al., "Molecular Docking: Challenges, Advances and its Use in Drug Discovery Perspective," Current Drug Targets 2019, 20 (5), 501-521.
Salum, et al., "Structure-Based Approach for the Study of Estrogen Receptor Binding Affinity and Subtype Selectivity," Journal of Chemical Information and Modeling 2008, 48 (11), 2243-2253.
Shahbaaz, et al., "Designing novel possible kinase inhibitor derivatives as therapeutics against *Mycobacterium tuberculosis*: An in silico study," Scientific Reports 2019, 9.
Spena, et al., "Virtual screening identifies a PIN1 inhibitor with possible antiovarian cancer effects," Journal of Cellular Physiology 2019, 234 (9), 15708-15716.
Stope, et al., "Re: Targeting the Regulation of Androgen Receptor Signaling by the Heat Shock Protein 90 Cochaperone FKBP52 in Prostate Cancer Cells," European Urology 2012, 62 (5), 931-932.
Svensson, et al., "Virtual Screening Data Fusion Using Both Structure- and Ligand-Based Methods," Journal of Chemical Information and Modeling 2012, 52 (1), 225-232.
Tan, et al., "Comprehensive Modeling and Discovery of Mebendazole as a Novel TRAF2-and NCK-interacting Kinase Inhibitor," Scientific Reports 2016, 6.
Tong, et al., "Molecular Virtual Screening Studies of Herbicidal Sulfonylurea Analogues Using Molecular Docking and Topomer CoMFA Research," Journal of Structural Chemistry 2019, 60 (2), 210-218.
Vora, et al., "Structure based virtual screening, 3D-QSAR, molecular dynamics and ADMET studies for selection of natural inhibitors against structural and non-structural targets of Chikungunya," Journal of Biomolecular Structure & Dynamics 2019, 37 (12), 3150-3161.
Warren, et al., "Essential considerations for using protein-ligand structures in drug discovery," Drug Discovery Today 2012, 17 (23-24), 1270-1281.
Xie, et al., "Early development of GMC1, a novel molecule targeting FKBP52 for the treatment of hormone-refractory prostate cancer" Cancer Research 2017, 77.
Xie, et al., "Pharmacophore modeling, virtual screening, and 3D-QSAR studies on a series of non-steroidal aromatase inhibitors," Medicinal Chemistry Research 2015, 24 (5), 1901-1915.
Yao, et al., "3DQSAR, molecular docking and molecular dynamics simulations study of 3-pyrimidin-4-yl-oxazolidin-2-one derivatives to explore the structure requirements of mutant IDH1inhibitors," Journal of Molecular Structure 2019, 1189, 187-202.
Yap, et al., "PaDEL-Descriptor: An Open Source Software to Calculate Molecular Descriptors and Fingerprints," Journal of Computational Chemistry 2011, 32 (7), 1466-1474.
Zhang, et al., "Molecular Modeling and Design Studies of Purine Derivatives as Novel CDK2 Inhibitors," Molecules 2018, 23 (11).

(56) References Cited

OTHER PUBLICATIONS

Zhang, et al., "Recent In Silico Research in High-Throughput Drug Discovery and Molecular Biochemistry," Current Topics in Medicinal Chemistry 2019, 19 (2), 103-104.

Zhang, et al., "Virtual Screening, Biological Evaluation, and 3D-QSAR Studies of New HIV-1 Entry Inhibitors That Function via the CD4 Primary Receptor," Molecules 2018, 23 (11).

Zhou, et al., "Discovery of Novel Androgen Receptor Ligands by Structure-based Virtual Screening and Bioassays," Genomics Proteomics & Bioinformatics 2019, 16 (6), 416-427.

Zhu, et al., "Identifying Potential Dual Inhibitory Candidates for Non-Small Cell Lung Cancer through Molecular Docking, 3D-QSAR Pharmacophore-based Virtual Screening,Comparative Molecular Field and Similarity Indices Analysis Modeling," Journal of Pharmaceutical Research International 2018, 24 (3).

TRAINING SET

TO FIG. 2B

16
$IC_{50} = 100 \mu M$, $pIC_{50} = 4.00$

18
$IC_{50} = 100 \mu M$, $pIC_{50} = 4.00$

15
$IC_{50} = 100 \mu M$, $pIC_{50} = 4.00$

17
$IC_{50} = 40.3 \mu M$, $pIC_{50} = 4.40$

24
$IC_{50} = 20.5 \mu M$, $pIC_{50} = 4.70$

26
$IC_{50} = 43.9 \mu M$, $pIC_{50} = 4.36$

23
$IC_{50} = 17.7 \mu M$, $pIC_{50} = 4.75$

25
$IC_{50} = 100 \mu M$, $pIC_{50} = 4.00$

38

IC$_{50}$ = 3.41μM, pIC$_{50}$ = 5.47

41

IC$_{50}$ = 100μM, pIC$_{50}$ = 4.00

37

IC$_{50}$ = 50μM, pIC$_{50}$ = 4.30

40

IC$_{50}$ = 100μM, pIC$_{50}$ = 4.00

TEST SET

IC$_{50}$ = 9.37μM, pIC$_{50}$ = 5.03

IC$_{50}$ = 32.5μM, pIC$_{50}$ = 4.49

IC$_{50}$ = 69.9μM, pIC$_{50}$ = 4.16

IC$_{50}$ = 100μM, pIC$_{50}$ = 4.00

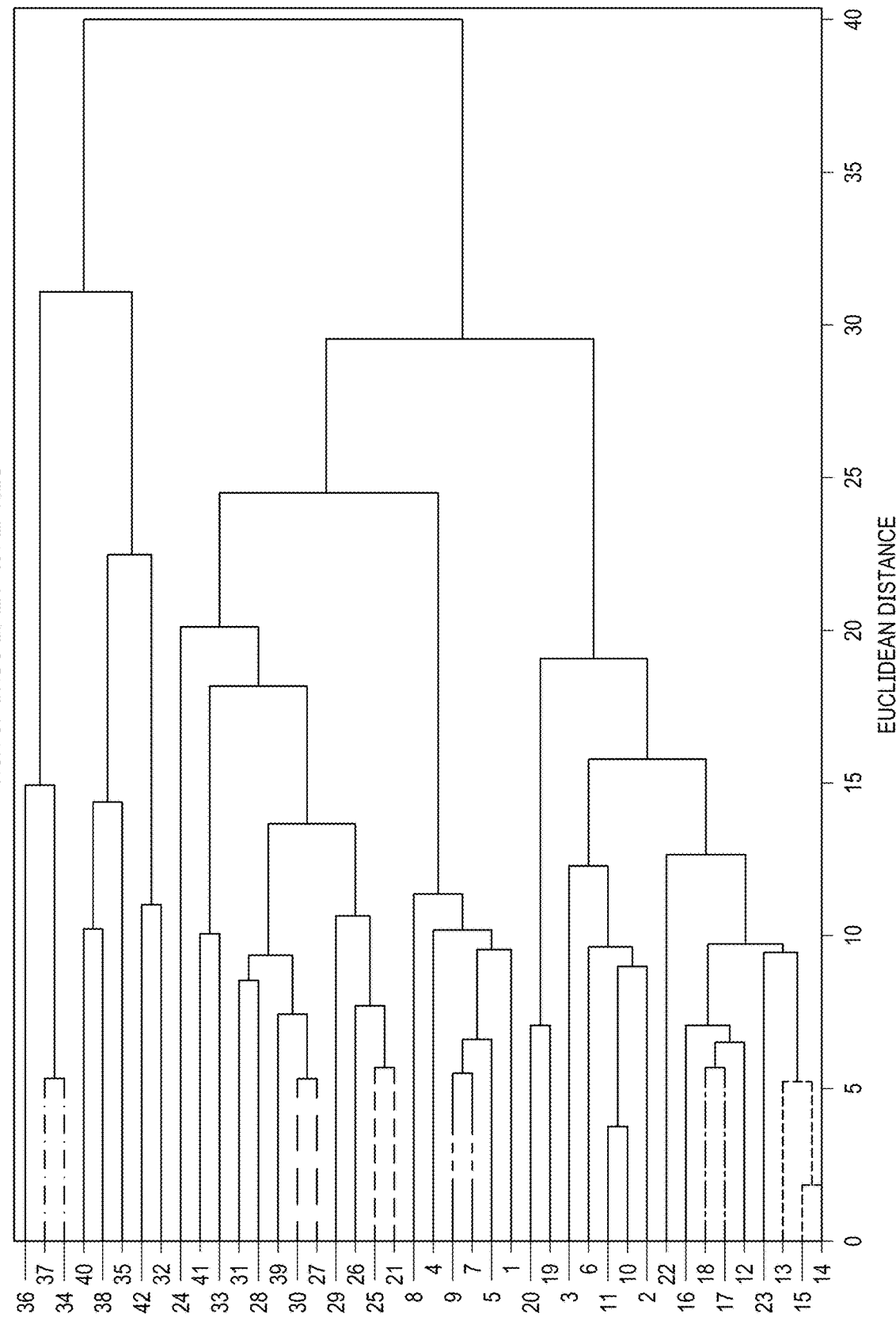

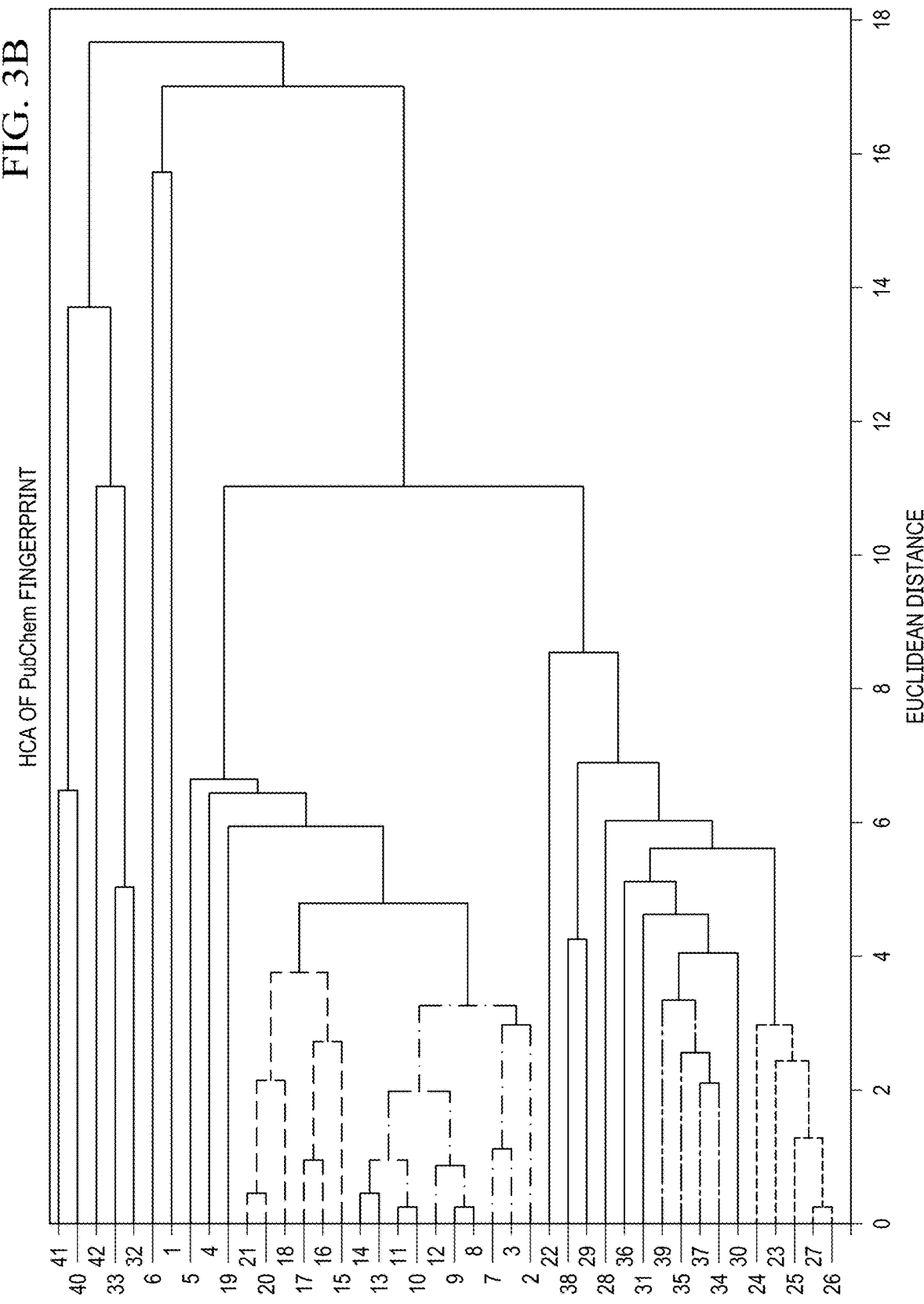

pIC$_{50}$ values and properties calculated for
42 FKBP52 inhibitors from PaDEL descriptors

FIG. 4

| Compound | Name | pIC$_{50}$ | MW | LogP | nHBAcc | nHBDon | HybRatio | nRotB | TopoPSA | LogS | PubChemFP |
|---|---|---|---|---|---|---|---|---|---|---|---|
| 2 | 1 | 5.03 | 520.16 | 2.64 | 7 | 1 | 0.44 | 13 | 128.67 | -4.98 | 0 |
| 8 | 2 | 4.00 | 675.23 | 6.04 | 9 | 1 | 0.31 | 15 | 162.83 | -5.41 | 1 |
| 9 | 3 | 4.48 | 631.16 | 6.19 | 7 | 1 | 0.36 | 14 | 137.05 | -6.16 | 1 |
| 10 | 4 | 4.49 | 654.17 | 6.15 | 8 | 1 | 0.34 | 14 | 178.18 | -5.60 | 1 |
| 11 | 5 | 4.00 | 587.18 | 5.13 | 7 | 1 | 0.38 | 14 | 150.19 | -4.62 | 1 |
| 12 | 6 | 4.00 | 655.19 | 6.52 | 7 | 1 | 0.39 | 14 | 162.35 | -6.16 | 1 |
| 13 | 7 | 4.16 | 622.20 | 4.18 | 8 | 1 | 0.36 | 14 | 160.84 | -5.50 | 1 |
| 14 | 8 | 4.00 | 643.20 | 4.87 | 7 | 2 | 0.36 | 15 | 174.35 | -5.00 | 1 |
| 15 | 9 | 4.00 | 612.21 | 5.12 | 8 | 2 | 0.36 | 14 | 163.07 | -5.26 | 1 |
| 16 | 10 | 4.00 | 689.24 | 6.53 | 9 | 1 | 0.33 | 15 | 162.83 | -5.54 | 1 |
| 17 | 11 | 4.00 | 675.23 | 6.04 | 9 | 1 | 0.31 | 15 | 162.83 | -5.39 | 1 |
| 18 | 12 | 4.07 | 615.19 | 5.67 | 7 | 1 | 0.36 | 14 | 137.05 | -5.88 | 1 |
| 19 | 13 | 4.80 | 675.11 | 6.30 | 7 | 1 | 0.36 | 14 | 137.05 | -6.00 | 1 |
| 20 | 14 | 4.85 | 665.13 | 6.84 | 7 | 1 | 0.36 | 14 | 137.05 | -6.58 | 1 |
| 21 | 15 | 4.00 | 665.13 | 6.84 | 7 | 1 | 0.36 | 14 | 137.05 | -6.58 | 1 |
| 22 | 16 | 4.00 | 657.22 | 5.55 | 7 | 1 | 0.39 | 16 | 155.51 | -5.46 | 1 |
| 23 | 17 | 4.40 | 661.17 | 6.20 | 7 | 1 | 0.38 | 15 | 146.28 | -6.01 | 1 |
| 24 | 18 | 4.00 | 633.18 | 5.81 | 7 | 1 | 0.36 | 14 | 137.05 | -5.81 | 1 |
| 25 | 19 | 4.00 | 761.21 | 7.75 | 7 | 1 | 0.43 | 18 | 137.05 | -5.47 | 1 |
| 26 | 20 | 4.00 | 757.12 | 7.40 | 7 | 1 | 0.39 | 16 | 137.05 | -6.30 | 1 |
| 27 | 21 | 4.00 | 713.21 | 3.78 | 11 | 1 | 0.37 | 18 | 189.65 | -5.73 | 1 |
| 28 | 22 | 4.69 | 681.12 | 6.55 | 7 | 2 | 0.36 | 14 | 157.28 | -5.67 | 1 |
| 29 | 23 | 4.75 | 695.14 | 6.85 | 7 | 1 | 0.38 | 15 | 146.28 | -6.33 | 1 |
| 30 | 24 | 4.69 | 812.12 | 5.96 | 11 | 3 | 0.37 | 19 | 242.25 | -6.25 | 1 |
| 31 | 25 | 4.00 | 701.21 | 3.92 | 9 | 2 | 0.38 | 17 | 192.81 | -5.03 | 1 |
| 32 | 26 | 4.36 | 685.21 | 4.80 | 7 | 2 | 0.39 | 15 | 183.58 | -4.85 | 1 |
| 33 | 27 | 4.00 | 654.22 | 5.55 | 8 | 2 | 0.39 | 14 | 172.30 | -5.10 | 1 |
| 34 | 28 | 4.58 | 668.19 | 6.09 | 8 | 1 | 0.36 | 14 | 178.18 | -5.75 | 1 |
| 35 | 29 | 4.18 | 670.17 | 5.61 | 9 | 2 | 0.34 | 14 | 191.45 | -5.23 | 1 |
| 36 | 30 | 4.00 | 652.21 | 5.63 | 9 | 2 | 0.36 | 14 | 166.15 | -5.00 | 1 |
| 37 | 31 | 4.00 | 654.19 | 4.26 | 9 | 2 | 0.34 | 14 | 175.38 | -4.88 | 1 |
| 38 | 32 | 4.00 | 517.07 | 5.43 | 5 | 0 | 0.41 | 10 | 99.75 | -5.59 | 0 |
| 39 | 33 | 4.00 | 506.12 | 4.19 | 6 | 0 | 0.39 | 10 | 140.88 | -4.22 | 0 |
| 40 | 34 | 4.30 | 720.20 | 6.59 | 7 | 0 | 0.46 | 15 | 112.22 | -6.36 | 1 |
| 41 | 35 | 4.30 | 709.25 | 5.35 | 8 | 0 | 0.44 | 15 | 153.35 | -5.44 | 1 |
| 42 | 36 | 6.15 | 736.20 | 6.29 | 7 | 1 | 0.46 | 15 | 132.45 | -5.90 | 1 |
| 43 | 37 | 4.30 | 750.21 | 6.60 | 7 | 0 | 0.47 | 16 | 121.45 | -6.30 | 1 |
| 44 | 38 | 5.47 | 725.24 | 5.35 | 9 | 1 | 0.44 | 15 | 166.62 | -5.32 | 1 |
| 45 | 39 | 5.08 | 867.20 | 5.14 | 11 | 2 | 0.46 | 20 | 217.42 | -6.22 | 1 |
| 46 | 40 | 4.00 | 680.14 | 6.12 | 7 | 3 | 0.36 | 14 | 160.08 | -5.50 | 1 |
| 47 | 41 | 4.00 | 669.18 | 5.18 | 9 | 3 | 0.34 | 14 | 194.25 | -5.22 | 1 |
| 48 | 42 | 4.82 | 607.17 | 7.00 | 8 | 0 | 0.30 | 16 | 137.06 | -4.90 | 1 |

| PARAMETER | NO FOCUS | REGION FOCUS ||||||||||
|---|---|---|---|---|---|---|---|---|---|---|---|
| | | w = 0.3 |||| w = 0.5 ||||
| | | d = 0.5 | d = 1.0 | d = 1.5 | d = 2.0 | d = 0.5 | d = 1.0 | d = 1.5 | d = 2.0 |
| $q^2_{LOO}$ | 0.542 | 0.695 | 0.669 | 0.79 | 0.705 | 0.86 | 0.807 | 0.731 | 0.548 |
| SEP | 0.148 | 0.171 | 0.276 | 0.162 | 0.158 | 0.225 | 0.28 | 0.333 | 0.137 |
| N | 6 | 5 | 6 | 2 | 6 | 4 | 6 | 4 | 5 |
| SEE | 0.193 | 0.073 | 0.065 | 0.065 | 0.084 | 0.057 | 0.075 | 0.214 | 0.37 |
| $r^2$ | 0.947 | 0.982 | 0.986 | 0.986 | 0.977 | 0.989 | 0.981 | 0.849 | 0.849 |
| S | 0.693 | 0.673 | 0.691 | 0.697 | 0.616 | 0.607 | 0.630 | 0.644 | 0.630 |
| E | 0.207 | 0.427 | 0.309 | 0.203 | 0.384 | 0.393 | 0.370 | 0.256 | 0.470 |

| PARAMETER | w = 0.7 |||| w = 0.9 ||||
|---|---|---|---|---|---|---|---|---|
| | d = 0.5 | d = 1.0 | d = 1.5 | d = 2.0 | d = 0.5 | d = 1.0 | d = 1.5 | d = 2.0 |
| $q^2_{LOO}$ | 0.89 | 0.981 | 0.88 | 0.512 | 0.789 | 0.72 | 0.575 | 0.517 |
| SEP | 0.16 | 0.195 | 0.184 | 0.102 | 0.166 | 0.419 | 0.252 | 0.139 |
| N | 5 | 5 | 4 | 5 | 6 | 6 | 2 | 6 |
| SEE | 0.255 | 0.064 | 0.192 | 0.318 | 0.213 | 0.215 | 0.371 | 0.08 |
| $r^2$ | 0.833 | 0.991 | 0.879 | 0.967 | 0.95 | 0.947 | 0.946 | 0.993 |
| S | 0.685 | 0.641 | 0.637 | 0.783 | 0.648 | 0.651 | 0.451 | 0.790 |
| E | 0.315 | 0.349 | 0.363 | 0.217 | 0.252 | 0.349 | 0.349 | 0.210 |

FIG. 6

| PARAMETER | NO FOCUS | REGION FOCUS ||||||||||
|---|---|---|---|---|---|---|---|---|---|---|---|
| | | w = 0.3 |||| w = 0.5 ||||
| | | d = 0.5 | d = 1.0 | d = 1.5 | d = 2.0 | d = 0.5 | d = 1.0 | d = 1.5 | d = 2.0 |
| $q^2_{LOO}$ | 0.506 | 0.628 | 0.721 | 0.742 | 0.676 | 0.801 | 0.883 | 0.977 | 0.726 |
| SEP | 0.276 | 0.244 | 0.211 | 0.199 | 0.251 | 0.215 | 0.183 | 0.182 | 0.344 |
| N | 5 | 6 | 6 | 5 | 4 | 5 | 5 | 4 | 4 |
| $r^2$ | 0.948 | 0.965 | 0.967 | 0.966 | 0.91 | 0.954 | 0.963 | 0.936 | 0.406 |
| SEE | 0.091 | 0.075 | 0.073 | 0.074 | 0.12 | 0.085 | 0.077 | 0.101 | 0.308 |
| S | 0.565 | 0.541 | 0.549 | 0.645 | 0.532 | 0.449 | 0.576 | 0.632 | 0.566 |
| A | 0.835 | 0.759 | 0.751 | 0.755 | 0.768 | 0.751 | 0.724 | 0.668 | 0.734 |

| PARAMETER | w = 0.7 |||| w = 0.9 ||||
|---|---|---|---|---|---|---|---|---|
| | d = 0.5 | d = 1.0 | d = 1.5 | d = 2.0 | d = 0.5 | d = 1.0 | d = 1.5 | d = 2.0 |
| $q^2_{LOO}$ | 0.879 | 0.984 | 0.799 | 0.666 | 0.759 | 0.884 | 0.759 | 0.626 |
| SEP | 0.259 | 0.179 | 0.354 | 0.397 | 0.259 | 0.199 | 0.364 | 0.377 |
| N | 6 | 4 | 3 | 2 | 6 | 4 | 3 | 2 |
| $r^2$ | 0.928 | 0.994 | 0.708 | 0.23 | 0.928 | 0.994 | 0.708 | 0.23 |
| SEE | 0.108 | 0.105 | 0.216 | 0.351 | 0.108 | 0.105 | 0.216 | 0.351 |
| S | 0.520 | 0.556 | 0.422 | 0.572 | 0.620 | 0.526 | 0.422 | 0.372 |
| A | 0.78 | 0.774 | 0.678 | 0.428 | 0.78 | 0.774 | 0.678 | 0.428 |

FIG. 7

| FOCUS | | | | | | | | FIELD CONTRIBUTION | |
|---|---|---|---|---|---|---|---|---|---|
| d | w | $q^2$ | SEV | $r^2$ | SEE | N | $dq^2/dr^2yy'$ | S | E |
| NO FOCUS | | 0.542 | 0.148 | 0.947 | 0.126 | 6 | - | 0.693 | 0.207 |
| 1.0 | 07 | 0.981 | 0.195 | 0.991 | 0.064 | 5 | 0.855 | 0.641 | 0.349 |

FIG. 8

| | FOCUS | | | | | | | FIELD CONTRIBUTION | |
|---|---|---|---|---|---|---|---|---|---|
| FIELDS | d | w | $q^2$ | SEV | $r^2$ | SEE | N | $dq^2/dr^2yy'$ | S | A |
| S/A | NO FOCUS | | 0.706 | 0.276 | 0.948 | 0.091 | 5 | - | 0.565 | 0.835 |
| S/A | 1.0 | 07 | 0.984 | 0.179 | 0.994 | 0.101 | 4 | 1.231 | 0.556 | 0.774 |

FIG. 9

| MODEL | $q^2$ | $r^2_{pred}$ | RMSEP | $r^2_m$ | $Q^2_{F2}$ | $Q^2_{F3}$ |
|---|---|---|---|---|---|---|
| CoMFA | 0.981 | 0.759 | 0.30 | 0.632 | 0.758 | 0.977 |
| CoMSIA | 0.984 | 0.852 | 0.24 | 0.711 | 0.986 | 0.986 |

FIG. 10

| CoMSIA | | | | |
|---|---|---|---|---|
| COMPOUND | EXPERIMENTAL $IC_{50}$ | EXPERIMENTAL $pIC_{50}$ | PREDICTED $pIC_{50}$ | RESIDUAL |
| 1 | 2.44 | 5.61 | 5.98 | -0.37 |
| 2 | 2.88 | 5.54 | 5.42 | 0.12 |
| 3 | 4.20 | 5.38 | 4.99 | 0.38 |
| 4 | 3.50 | 5.46 | 5.07 | 0.39 |
| 5 | 6.20 | 5.21 | 5.16 | 0.04 |
| 6 | 2.20 | 5.66 | 5.44 | 0.22 |
| 7 | 2.64 | 5.58 | 5.34 | 0.24 |
| 8 | 9.53 | 5.02 | 4.99 | 0.04 |
| 9 | 11.60 | 4.94 | 4.57 | 0.37 |
| 10 | 1.71 | 5.77 | 5.50 | 0.27 |
| 11 | 5.60 | 5.25 | 5.16 | 0.10 |
| 12 | 9.77 | 5.01 | 5.00 | 0.01 |
| 13 | 100.00 | 4.00 | 3.99 | 0.01 |
| 14 | 11.70 | 4.93 | 4.84 | 0.10 |
| 15 | 100.00 | 4.00 | 3.90 | 0.10 |
| 16 | 41.60 | 4.38 | 4.34 | 0.04 |
| 17 | 49.20 | 4.31 | 4.33 | -0.02 |
| 18 | 46.20 | 4.34 | 4.13 | 0.21 |
| 19 | 100.00 | 4.00 | 3.99 | 0.01 |
| 20 | 100.00 | 4.00 | 3.90 | 0.10 |
| 21 | 100.00 | 4.00 | 3.79 | 0.21 |
| 22 | 0.89 | 6.05 | 5.99 | 0.06 |

FIG. 15

|         | CoMFA | | | CoMSIA | |
|---|---|---|---|---|---|
| COMPOUND | EXPERIMENTAL $pIC_{50}$ | PREDICTED $pIC_{50}$ | RESIDUAL | PREDICTED $pIC_{50}$ | RESIDUAL |
| 2 | 4.00 | 3.99 | 0.01 | 4.32 | -0.32 |
| 4 | 4.49 | 4.42 | 0.07 | 4.33 | 0.16 |
| 7 | 4.16 | 3.93 | 0.23 | 4.14 | 0.02 |
| 11 | 4.00 | 4.00 | 0.00 | 3.98 | 0.02 |
| 22 | 4.69 | 4.20 | 0.49 | 4.53 | 0.16 |
| 34 | 4.30 | 4.33 | -0.03 | 4.25 | 0.05 |
| 39 | 5.08 | 5.03 | 0.05 | 5.13 | -0.05 |
| 42 | 4.82 | 4.62 | 0.20 | 4.79 | 0.02 |

FIG. 16

| nCV | CoMSIA - CROSS-VALIDATION (CV) | | | | |
|---|---|---|---|---|---|
| | $q^2_1$ | $q^2_2$ | $q^2_3$ | AVERAGE | STANDARD DEVIATION |
| 5 | 0.899 | 0.900 | 0.900 | 0.900 | 0.001 |
| 10 | 0.901 | 0.902 | 0.904 | 0.902 | 0.002 |
| 15 | 0.904 | 0.905 | 0.907 | 0.905 | 0.002 |
| 20 | 0.908 | 0.907 | 0.909 | 0.908 | 0.001 |
| 25 | 0.967 | 0.965 | 0.968 | 0.967 | 0.002 |
| 30 | 0.977 | 0.968 | 0.978 | 0.977 | 0.006 |
| 35 | 0.979 | 0.976 | 0.980 | 0.979 | 0.002 |
| 40 | 0.98 | 0.982 | 0.981 | 0.981 | 0.001 |
| 45 | 0.984 | 0.984 | 0.984 | 0.984 | 0 |
| 50 | 0.984 | 0.984 | 0.984 | 0.984 | 0 |

NEXT GENERATION FKBP52 TARGETING DRUGS FOR THE TREATMENT OF PROSTATE AND BREAST CANCER

CROSS-REFERENCE TO RELATED APPLICATION

This application is a utility conversion and claims priority to U.S. Ser. No. 62/963,873, filed Jan. 21, 2020, the contents of which are incorporated herein by reference in their entirety for all purposes.

This invention was made with government support under W81XWH-17-1-0435 awarded by the Medical Research and Development Command. The government has certain rights in the invention.

BACKGROUND INFORMATION

1. Field

The present invention relates generally to the field of medicine and disease treatment. More particularly, it concerns methods of inhibiting hormone receptor activation and treating cancer.

2. Background

Androgens are a major stimulator of prostate tumor growth and all current therapies act as classic antagonists by competing with androgens for binding the AR (androgen receptor) hormone binding pocket. This mechanism of action exploits the dependence of AR for hormone activation and current treatment options are essentially ineffective once androgen-dependence is lost. Thus, drugs that target novel surfaces on AR and/or novel AR regulatory mechanisms are promising additions for the treatment of hormone refractory prostate cancer. Both FKBP52 and β-catenin have emerged in recent years as attractive therapeutic targets. Applicant's previous patents describe MJC13, which represents a first-in-class drug for targeting the regulation of AR by FKBP52. Through binding a recently identified regulatory surface on AR (BF3), MJC13 prevents the FKBP52-receptor complex from dissociating resulting in the retention of AR in the cytoplasm. MJC13 was shown to effectively block AR signaling and AR-dependent cancer cell proliferation in a variety of human prostate cancer cell lines, and preliminary preclinical studies demonstrate impressive effects on tumor growth in a prostate cancer xenograft model.

Applicants previously described MJC13 as an inhibitor of FKBP52-regulated AR activity (De Leon et. al. 2011. *PNAS.* 108(29): 11878-83) by targeting the AR BF3 surface. Applicants have also generated a large amount of preliminary data describing a novel mechanism by which FKBP52 and β-catenin interact to co-regulate AR activity in prostate cancer cells. In addition, Applicants have preliminary data demonstrating that MJC13 targeting to the AR BF3 surface abrogates β-catenin interaction with AR (manuscript in preparation). Our data show that the FKBP52 proline-rich loop is critical for FKBP5243-catenin co-regulation of AR activity, and that drugs that disrupt interactions at the proline-rich loop would effectively block FKBP5243-catenin/AR interactions. Applicants propose that specific small molecules docked within the PPIase pocket can affect proline-rich loop conformation and interactions. Precedence exists for this as FK506-binding to the FKBP12 PPIase pocket leads to a reorientation of the FKBP12 proline-rich loop. Thus, Applicants elected to perform structure-based drug design to identify small molecules predicted to target the FKBP52 PPIase pocket. Our previous, smaller scale in silico screens identified GMC1 as a hit molecule that displayed specific inhibition of AR, GR and PR activity and Applicants patented this molecule for use in treating prostate and breast cancer. In the meantime, Applicants have performed a broader scale in silico screen to identify the next generation of direct FKBP52 targeting drugs that represent new chemotypes independent of GMC1. That broader in silico screening process and the new hit molecules identified are detailed below.

Prostate cancer is the most common cancer among men in several countries, which have presented 1.3 million new cases in 2018 alone[1]. The chaperon proteins of the cancer patients facilitate both the dynamic protein folding, unfolding, organization, and degradation through ATP-dependent cycles of binding and releasing for the protein's function.[2-3] One family of such chaperones are FK506-binding proteins (FKBPs); FKBPs and cyclophilins (CyP) belong to the immunophilin family that are cellular receptors for immunosuppressant drugs such as FK506, rapamicyn and cyclosporine A (CsA).[2-3] FKBPs exhibit peptidyl prolyl isomerase (PPIase) activity and catalyze the cis/trans isomerization in protein folding process in the cytoplasm, and have important roles of protein stability, protein trafficking, receptor signaling and others.[2-3]

FKBP52 (also known as FKBP59/HSP56) is an immunophilin belonging to the FKBP family and is an important member of the inactive steroid receptor/heat-shock protein 90 heterocomplex (HSP90) complex. FKBP52 is a positive regulator for binding of hormones to steroid hormone receptors, which has been presented in studies[4-6] by reporter gene assays in yeast and mammalian cells.[2-3] In hormone-dependent prostate cancers, the level of FKBP52 expression is highly up-regulated compared to the normal tissue.[2-3] In addition, the immunophilin enhances the androgen receptor actions of those therapies based on androgen excision[3, 7]. Therefore, even though the androgen levels in the plasma are greatly reduced, the androgen can generate a response via AR-HSP90 complexes.[4] Studies of human prostate biopsies revealed that FKBP52 is in fact a useful and reliable biomarker of prostate cancer.[3, 7]

The biological and physiological function of FKBP52 rendered it as a potential drug target for prostate cancer treatment.[2-3, 7-9]

However, no computational investigation of FKBP52 has been reported.[3-5, 7] Virtual screening (VS) has been extensively reviewed in the literature[10-15], which refers to the application of computational algorithms and models for the identification of novel bioactive compounds. For billion compounds of virtual screening libraries, VS provides a complementary strategy to the conventional HTS[15-19] in pharmaceutical industry.[20] Although the HTS technology was employed for the development of many drug candidates, the VS approach is particularly valuable and practical for hit and lead discovery in academic organizations or small biotechnology companies, because the large scale HTS is not encouraged due to the demanding cost of resources and time.[13-14]. In particular, docking and pharmacophore-based searching technologies have advanced considerably and have become essential tools in lead discovery and lead optimization of drug discovery[13, 21-23] The scope of VS can be divided into Ligand-Based Virtual Screening (LBVS) and Structure-Based Virtual Screening (SBVS)[24-25] both LBVS and SBVS technologies may accelerate the process of drug discovery.[22]

LBVS is based on the fact that similar compounds should have similar properties. The similarity of compounds to an active query compound against a particular target is evaluated by the desired properties of the query compound.[26] Pharmacophore modelling[27], similarity search[26], fingerprint search[28], 3D-shape similarity search[29] are important techniques in LBVS.

Pharmacophore modelling is to identify the common features of a set of known active compounds of a biological target, which can be used as a filter to shrink down the large virtual compound libraries for further hit selection.[30] Recent development of structure-based pharmacophore model can also be created by overlapping the predicted binding poses of small molecules docked to a biological target[24], the common binding interactions between the docked ligands and residues of the binding site can be easily identified and visualized.[31]

Similarity search characterizes objects as feature vectors in high-dimensional spaces.[26] Essentially, the query compound is submitted to a search engine and the search returns compounds similar to the query.[22, 26] It has recently gained considerable interest because of its high performance in screening large compound databases.[22, 26] The similarity between two compounds is measured by distance function between their feature vectors, and the similarity search outputs the compounds that are nearest to the query compound in high-dimensional spaces.[26]

Fingerprint search finds similar molecules by comparison of the fingerprint bits[28, 32] to a query compound. Fingerprint is simply a sequence of bits, each of which represents a specific piece of the compound.[28, 32] The bits of a compound's fingerprint are based on sub-structure keys, topological or path, circular, pharmacophore, or SMILES[28, 32], which are quantifiable to evaluate molecular similarity.[28, 32]

Besides the above LBVS methods, quantitative structure-activity relationship (QSAR) approach is an important methodology[33] in medicinal chemistry. CoMFA and CoMSIA methodology[34-36] is an attractive technology in 3D-QSAR approach that operates on 3D descriptors and PLS. CoMFA and CoMSIA techniques are commonly used in drug discovery by evaluating common features that are important for ligand binding to a drug target.[37-38] CoMSIA is an extension of the CoMFA on the assumption that changes in binding affinities of ligands correlate to the changes in molecular properties represented by fields.[38] They differ only in the implementation of the fields.[39-40]

In CoMFA and CoMSIA, a group of structurally aligned molecules are represented by their molecular property fields that are evaluated between a probe atom and each molecule at regularly spaced intervals on a grid. CoMFA calculates steric fields using Lennard-Jones potential and electrostatic fields using a Coulomb potential, while CoMSIA calculates fields of steric, electrostatic, hydrophobic, hydrogen bond donor and hydrogen bond acceptor to account for the major contributions to ligand binding.[39-41] CoMFA and CoMSIA do the systematic sampling of those field differences to produce molecular descriptors well-suited for QSAR.[38, 40, 42]

Normally, the relevant activity data can be retrieved for developing ligand-based QSAR model, which can be applied for VS hit selection or for lead optimization.[24] A large number of known inhibitors are curated in public accessible databases such as ChEMBL[43], BindingDB[44], Reaxys[45] or PubChem[46]. However, beside the availability of chemical data in literature[40, 47], the quality of the primary activity data affects the performances of QSAR models the most.[33]

In SBVS, docking is the core technology, which is commonly used from screening large chemical libraries of millions of compounds.[16] The aim of docking is to predict the correct binding poses of compounds in the binding site of a target protein and to rank the binding affinities precisely.[48] The binding poses of a compound in an active site are generated by the docking algorithms and ranked by the score functions, by which the resulting docking score should theoretically correlate to its affinity of the receptor site.[15, 44, 49-51] Docking needs 3-dimensional protein structure to predict how the compounds should bind to the active site.[52] The hit selection after docking can be assisted by employing a structure-based pharmacophore model as a filter, by which compounds without required binding features in the active site are rejected.[52] The quality of virtual screening may simply be measured by enrichment factor[52] using the confirmed number of VS hits in the screening assays.[41, 49]

All the above methodologies are very applicable and contribute to the drug discovery tremendously.[13, 15-16, 26, 43, 53] And new ligand-based and structure-based computational technologies for drug design and development are emerging from many research groups across the world.[10, 22, 49, 54-55] The LBVS methods are generally very fast and computationally much cheaper than the docking method of SBVS[32, 52] and can make hit selection from large compound databases rational and efficient.[52]

One of the big challenges in SBVS is to rank the binding affinity of ligands accurately.[31, 52] Docking uses scoring functions to the rank docking poses of small molecules in protein active site; however, the quality of scoring function is empirical and still unsatisfactory in terms of ranking binding affinity of different ligands.[33, 56-61] Thus, many potential compounds would be lost just because the chosen score function cannot rank the ligands properly.[61-63] Hence, computational drug design is still focusing on improvement of docking programs, score functions[56], and data fusion.[4, 64] In this regards, CoMFA and CoMSIA and others methodologies of QSAR[10, 24, 33, 63] may provide a good ranking solution by training a model from available experimental data. Several VS studies have reported that consensus docking, pharmacophore filter and 3D-QSAR, such as CoMFA and CoMSIA, are good approaches for hit selection.[10, 24, 33, 63, 65-66]

SUMMARY

An overall goal of embodiments of the present disclosure is to develop drugs that target the FKBP52 PPIase pocket for the disruption of proline-rich loop interactions with AR for the treatment of prostate and breast cancer. Embodiments of the present disclosure include methods that use identified three molecules PC257 (ZINC3424402) Formula I, PC892 (ZINC457474880) Formula II, and PC615 (ZINC161085867) Formula III. All 3 molecules are readily commercially available from Enamine, (located at 1 Distribution Way, Monmouth Jct., N.J. 08852, USA).

PC257: ZINC3424402; CC1=CC(C(=O)COC(=O) CC2=NNC(=O)C=3C=CC=CC23)=C(C) N1CC4COC=5C=C C=CC5O4; [2-[1-[[(3S)-2,3-Dihydro-1,4-benzodioxin-3-yl]methyl]-2,5-dimethylpyrrol-3-yl]-2-oxoethyl] 2-(4-oxo-3H-phthalazin-1-yl)acetate; C27H25N3O6; "Formula I".

PC615: ZINC161085867; CCC1=NNC(=N1) C=2C=CC=CC2NC(=O)C(C)OC=3C=CC(C#N)= CC3; 2-(4-cyanophenoxy)-N-[2-(3-ethyl-1H-1,2,4-triazol-5-yl)phenyl]propenamide; C20H19N5O2; "Formula II".

PC892: ZINC457474880; CC(C)C1=NNC(=N1)C=2C=CC=CC2NC(=O)C(C)CC=3C=NN(C)C3; 2-methyl-3-(1-methyl-1H-pyrazol-4-yl)-N-{2-[3-(propan-2-yl)-1H-1.2.4-triazol-5-yl]phenyl}propenamide; C19H24N6O; "Formula III".

An illustrative embodiment of the present disclosure provides a method of inhibiting hormone receptor activation, comprising administering to a subject in need of hormone receptor inhibition a compound having a chemical structure of Formula I Formula I

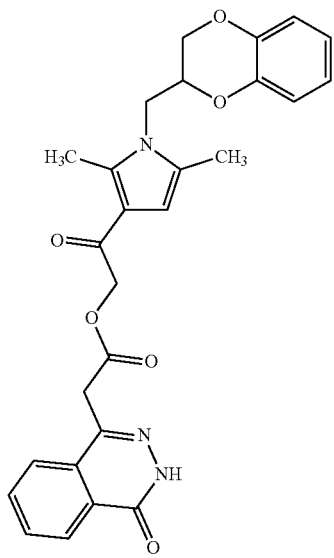

An illustrative embodiment of the present disclosure provides a method of treating prostate cancer or breast cancer comprising administering to a subject having prostate cancer or breast cancer a compound having a chemical structure of Formula I Formula I

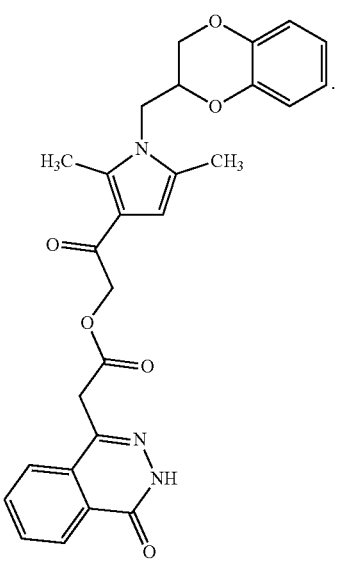

An illustrative embodiment of the present disclosure provides a method of inhibiting hormone receptor activation, comprising administering to a subject in need of hormone receptor inhibition a compound having a chemical structure of Formula II Formula II

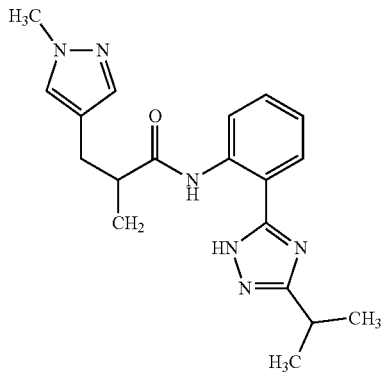

An illustrative embodiment of the present disclosure provides a method of treating prostate cancer or breast cancer comprising administering to a subject having prostate cancer or breast cancer a compound having a chemical structure of Formula II Formula II

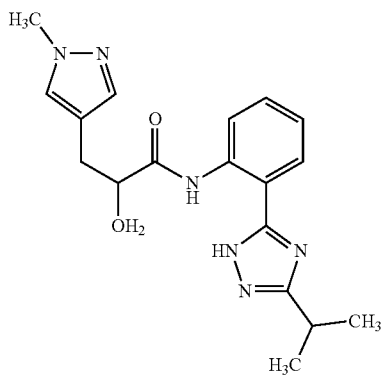

An illustrative embodiment of the present disclosure provides a method of inhibiting hormone receptor activation, comprising administering to a subject in need of hormone receptor inhibition a compound having a chemical structure of Formula III Formula III

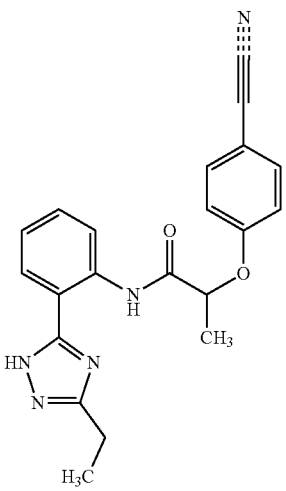

An illustrative embodiment of the present disclosure provides a method of treating prostate cancer or breast cancer comprising administering to a subject having prostate cancer or breast cancer a compound having a chemical structure of Formula III

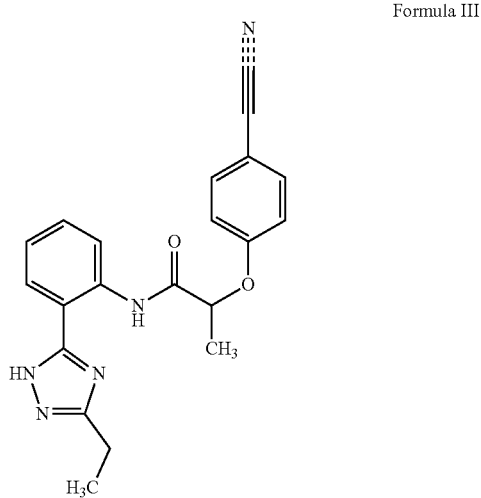

Formula III

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-3C depict dendograms generated with HCA using each set of descriptors in accordance with an illustrative embodiment. (FIG. 3A) Druglike properties. (FIG. 3B) molecular PubChem fingerprint. (FIG. 3C) Distribution of compounds among training and test sets according to their different chemical representative calculated drug-like properties, PubChem fingerprint clusters as representative of structural diversity and the $pIC_{50}$ range representing the biological activity.

FIG. 4 presents $pIC_{50}$ values and properties calculated for 42 FKBP52 inhibitors from PaDEL descriptors in accordance with an illustrative embodiment.

(FIG. 5A) ligand from the crystal structure of FKBP52 (PDB ID: 4LAY) used as a template for the alignment. (FIG. 5B) Final alignment of data set. Compound: From literature cited in manuscript; $IC_{50}$: Half maximal inhibitory concentration; $pIC_{50}$: $-\log IC_{50}$; MW: Molecular weight; Log P: Partition coefficient of a molecule between an aqueous and lipophilic phases, normally octanol and water; nHBAcc: Number of hydrogen bond acceptor; nHBDon: Number of hydrogen bond donor; HybRatio: Characterizes molecular complexity in terms of carbon hybridization states; nRotB: number of rotatable bonds; TopoPSA: Topological polar surface area; Log S: Aqueous solubility; PubChemFP: PubChem fingerprint.

FIG. 6 presents statistical results for all CoMFA models obtained from the region focusing technique in accordance with an illustrative embodiment. $q^2_{LOO}$: Validation coefficient using (leave-one-out); SEP: standard error of prediction; N: number of main components obtained from the PLS technique; $r^2$: regression coefficient without validation; SEE: standard non-cross validation error; S: steric contribution; E: electrostatic contribution. w=weight; d (Å)=distance between the grid points.

FIG. 7 presents statistical results for all CoMSIA models obtained from the region focusing technique in accordance with an illustrative embodiment. $q^2_{LOO}$: Validation coefficient using (leave-one-out); SEP: standard error of prediction; N: number of main components obtained from the PLS technique; $r^2$: regression coefficient without validation; SEE: standard non-cross validation error; A: H-bond acceptor contribution; w=weight; d (Å)=distance between the grid points.

FIG. 8 presents statistical data of the best constructed CoMFA models for FKBP52 inhibitors in accordance with an illustrative embodiment. d, distance factor; w, standard deviation weight factor; $q^2$, LOO cross-validation correlation coefficient; SEV, standard error of validation; N, optimal number of components; $r^2$, non-cross-validation correlation coefficient; SEE, standard error of estimation; $dq^2/dr^{2yy'}$, sensitivity index from the scrambling test. Field contribution: S, steric; E, electrostatic.

FIG. 9 presents statistical data of the best constructed CoMSIA models for FKBP52 inhibitors in accordance with an illustrative embodiment. d, distance factor; w, standard deviation weight factor; $q^2$, LOO cross-validation correlation coefficient; SEV, standard error of validation; N, optimal number of components; $r^2$, non-cross-validation correlation coefficient; SEE, standard error of estimation; $dq^2/dr^{2yy'}$, sensitivity index from the scrambling test. Field contribution: S, steric; A, Hydrogen acceptor.

FIG. 10 presents validation of the COMFA and CoMSIA models in accordance with an illustrative embodiment. $q^2$: LOO cross-validation correlation coefficient; $r_{pred}^2$: external predictive potential of the model; RMSEP: Root-mean-square error of prediction; $r_m^2$: external predictive potential of the model modified

(FIG. 14A) CoMFA model, (FIG. 14B) CoMSIA model and (FIG. 14C) predicted by CoMSIA; black dots represent training set and grey dots represents test set.

FIG. 15 presents experimental and predicted $pIC_{50}$ for test compounds 1-22 in accordance with an illustrative embodiment.

FIG. 16 presents experimental and predicted $pIC_{50}$ for test compounds 2, 4, 7, 11, 22, 34, 39 and 42 in accordance with an illustrative embodiment.

(FIG. 20A) An in silico screen lead to 107 lead molecules for functional screening that lead to an initial hit molecule PC257 (ZINC3424402). (FIG. 20B) MDA-kb2 cells expressing a stably AR- and GR-response luciferase reporter was treated with 200 pM DHT with a range of PC257 (ZINC3424402) concentrations (0, 0.01, 0.1, 1, 10, 25, 50, and 100 uM) for 16-18 hours in order to test for AR-dependent activity. The graphs represent an average of 4 independent receptor mediated luciferase receptor experiments. (FIG. 20C) MDA-kb2 cells expressing a stably AR- and GR-responsive luciferase reporter was treated with 50 nM DEX with a range of PC257 (ZINC3424402) concentrations (0, 0.01, 0.1, 1, 10, 25, 50, and 100 uM) for 16-18 hours in order to test for GR-dependent activity. The graphs represent an average of 4 independent receptor mediated luciferase receptor experiments. (FIG. 20D) T47D-KBluc cells express ERα and ERβ, cells were treated with 10 pM E2 with a single high dose of 100 uM PC257 (ZINC3424402) and vehicle control for 16-18 hours in order to test for effects on ER-regulated activity.

DETAILED DESCRIPTION

Broader Scale Screen in Silico Screen for Fkbp52 Inhibitors

While the targeting of the FKBP52 regulatory surface on AR is a promising therapeutic strategy that allows for AR-specific targeting, direct targeting of FKBP52 offers a number of advantages over MJC13 that would lead to a more potent and effective drug. First, the AR BF3 surface represents a less than ideal drug binding site, and, as a result, Applicants have only been able to achieve effective drug concentrations in the low micromolar range. In contrast, the FKBP52 PPIase pocket not only represents an ideal hydrophobic drug binding pocket, but the FKBP PPIase pocket is a known 'druggable target' as the immunosuppressive drug Tacrolimus is already FDA approved for use in the clinic. Also, given the conservation within the FKBP PPIase pocket, drugs targeting the FKBP52 PPIase pocket would likely target FKBP52 and the closely related FKBP51 protein simultaneously. While FKBP52, but not FKBP51, is largely considered the relevant steroid hormone receptor regulator, more recent evidence suggests that both FKBP51 and FKBP52 are positive regulators of AR in prostate cancer cells. In addition, FKBP52 is a known positive regulator of AR, GR and PR, and the direct targeting of FKBP52 would target the activity of all three receptors simultaneously. Increasing evidence suggests that many factors (e.g. growth factors, cytokines, and angiogenic factors) implicated in prostate cancer progression are targets of the GR signaling pathway. In addition, recent evidence suggests that GR signaling confers resistance to current antiandrogen treatments. While very little work has been done to characterize a role for PR in prostate cancer, data suggests that PR expression is elevated in metastatic disease, and that PR antagonist are potential treatments for prostate cancer. Finally, based on preliminary data discussed below, targeting FKBP52 proline-rich loop interactions will abrogate β-catenin interaction with AR. Thus, the direct targeting of FKBP52 with small molecules will lead to a more potent drug with the potential to simultaneously hit a variety of targets known to have, or suspected of having, a role in prostate cancer.

Figure 1:
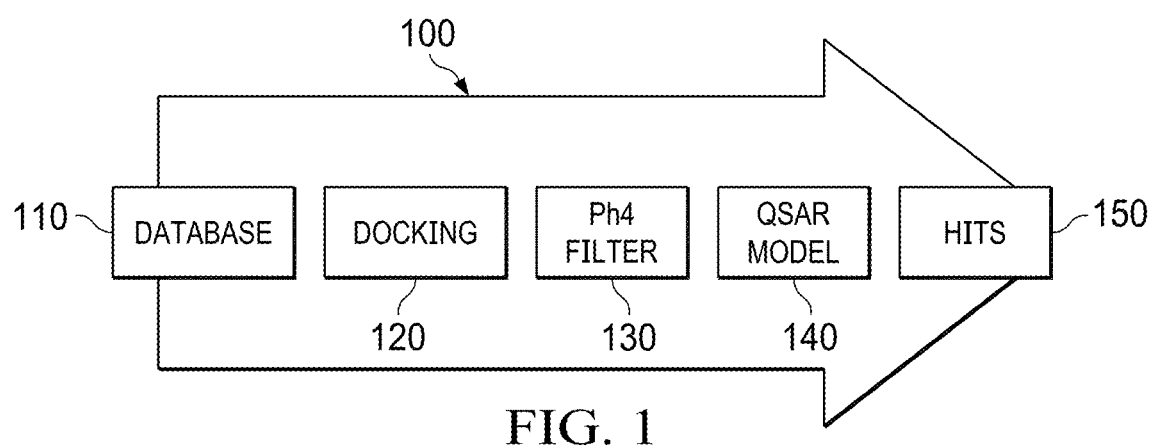
FIG. 1 depicts a workflow of an FKBP52 virtual screening pipeline in accordance with an illustrative embodiment.
Figure 2A:
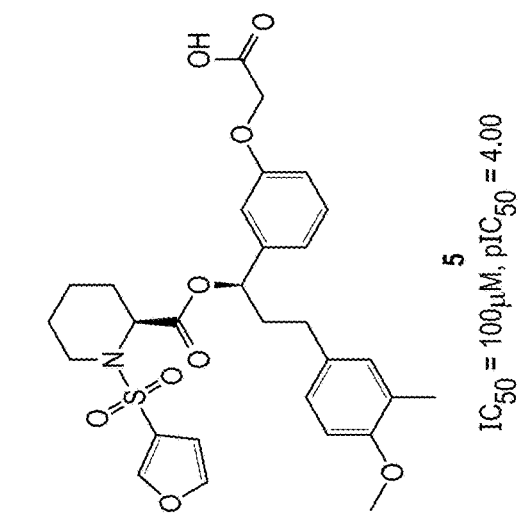
FIGS. 2A-2J present structures and $pIC_{50}$ values for FKBP52 inhibitors in accordance with an illustrative embodiment.
Figure 2A:
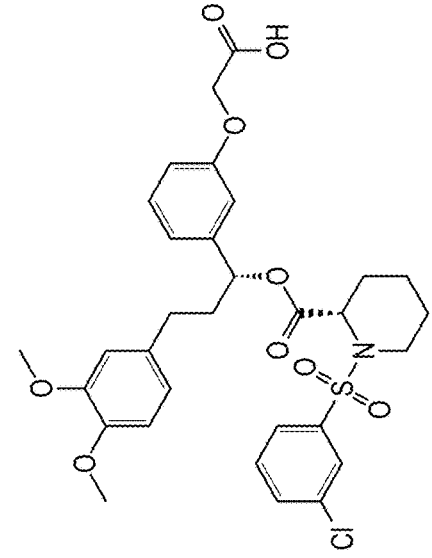
Figure 2A:
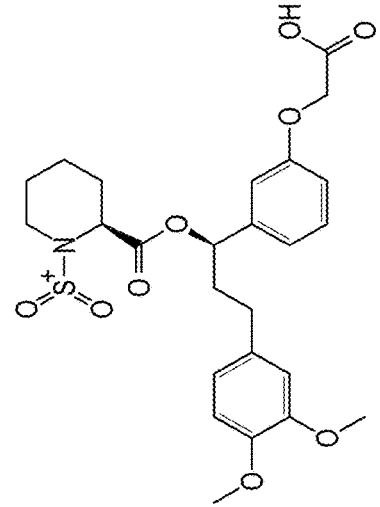
Figure 2A:
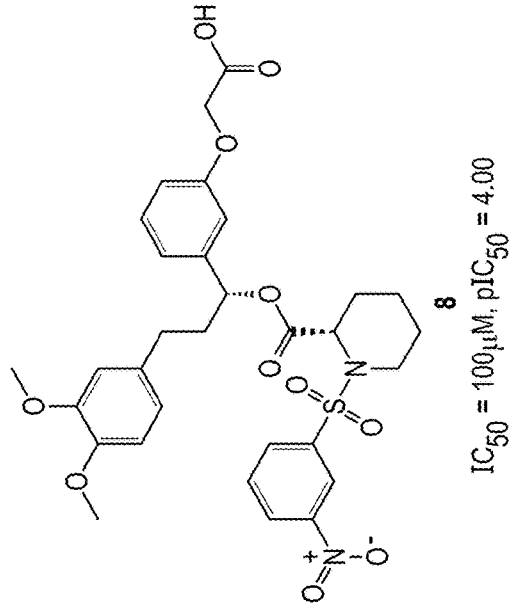
Figure 2A:
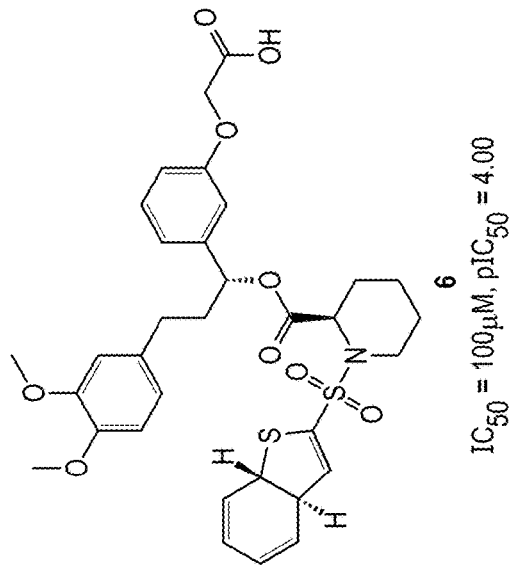
Figure 2B:
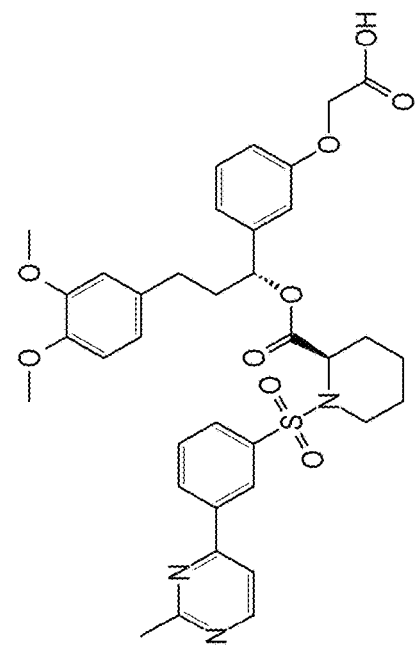
Figure 2B:
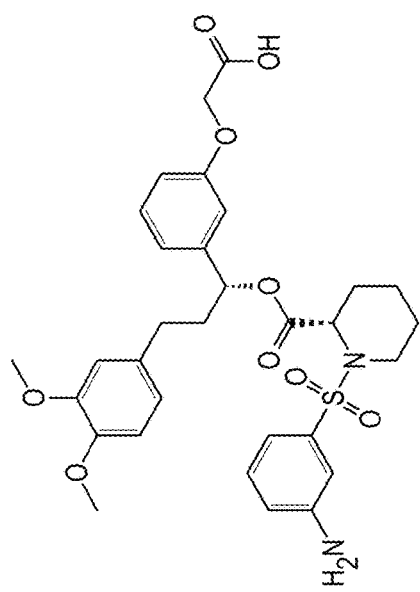
Figure 2B:
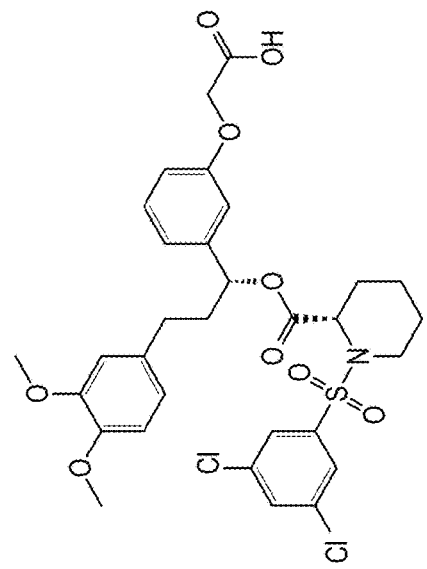
Figure 2B:
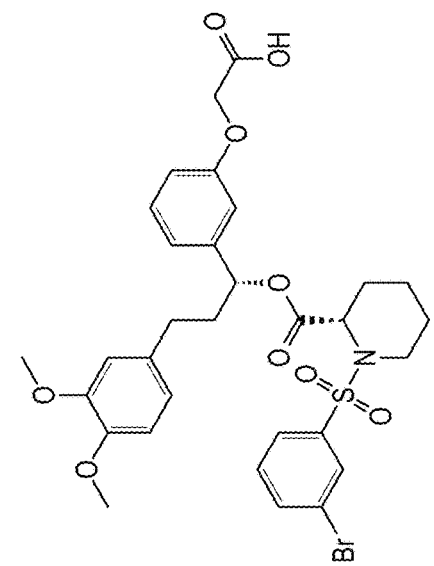
Figure 2B:
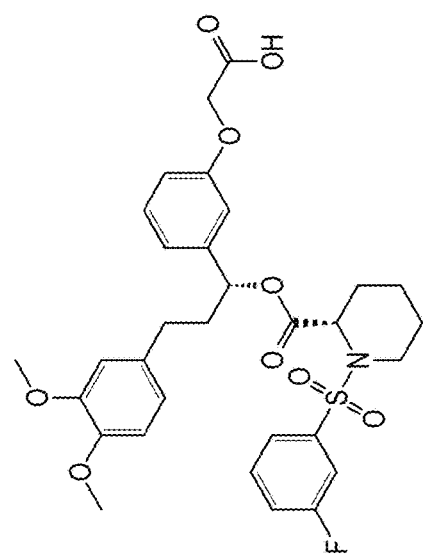
Figure 2C:
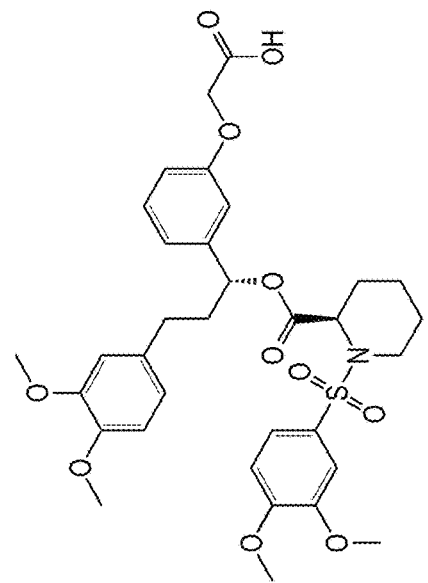
Figure 2C:
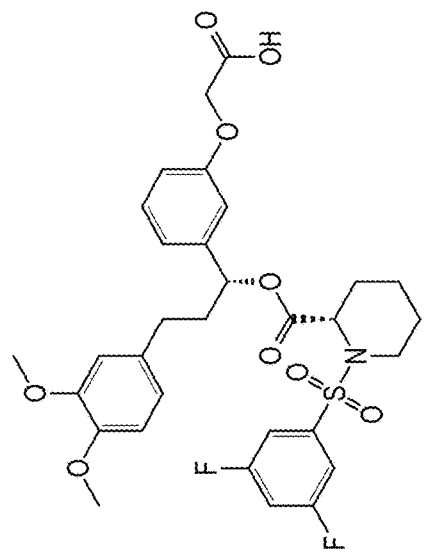
Figure 2C:
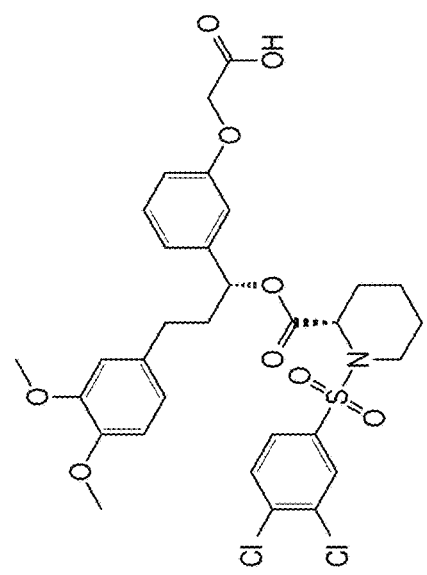
Figure 2C:
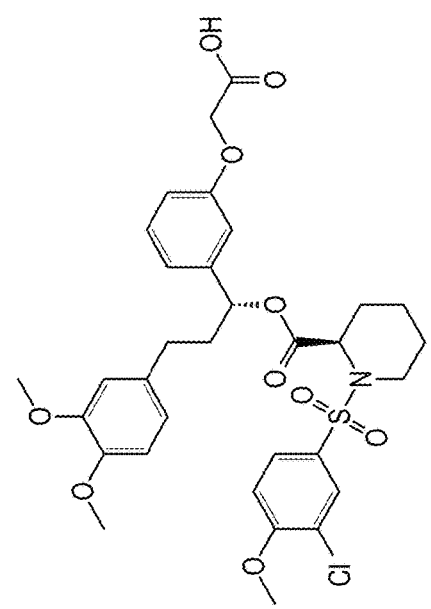
Figure 2D:
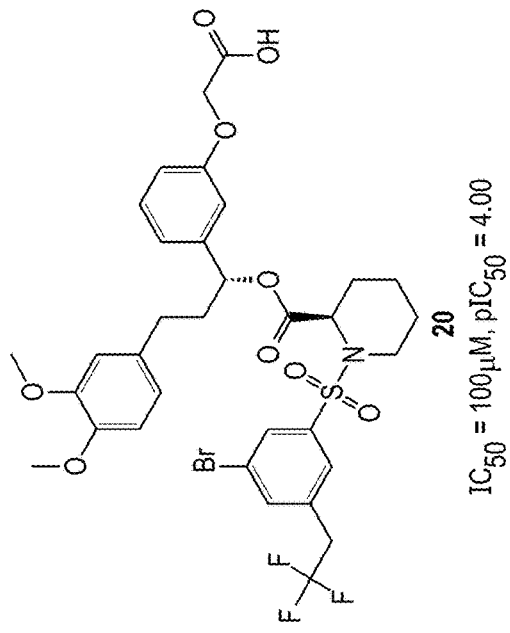
Figure 2D:
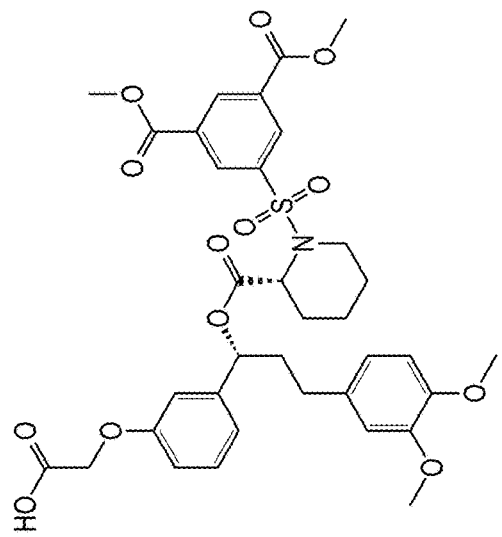
Figure 2D:
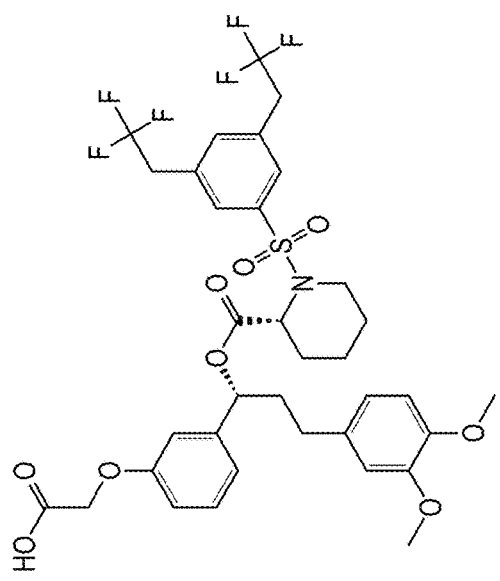
Figure 2E:
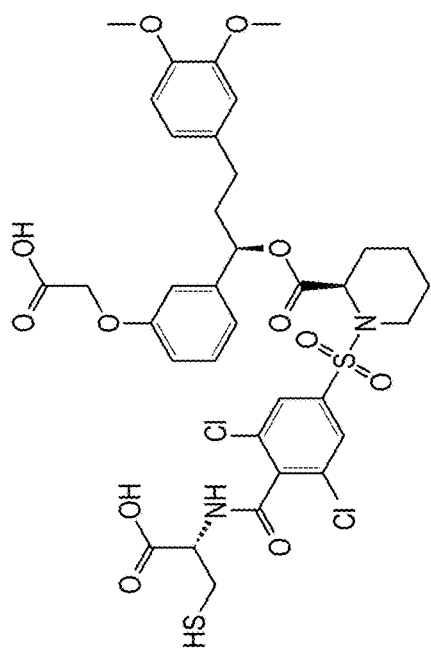
Figure 2E:
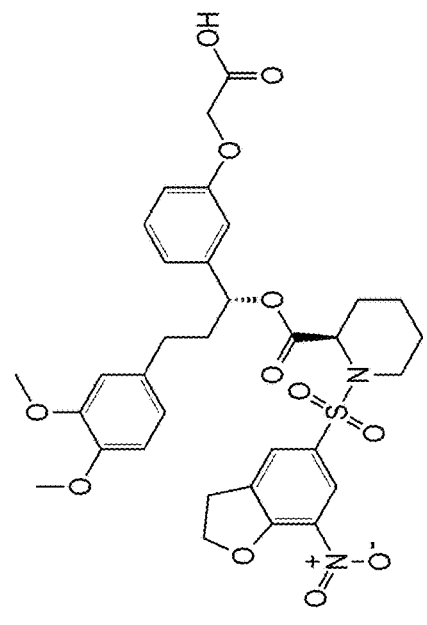
Figure 2E:
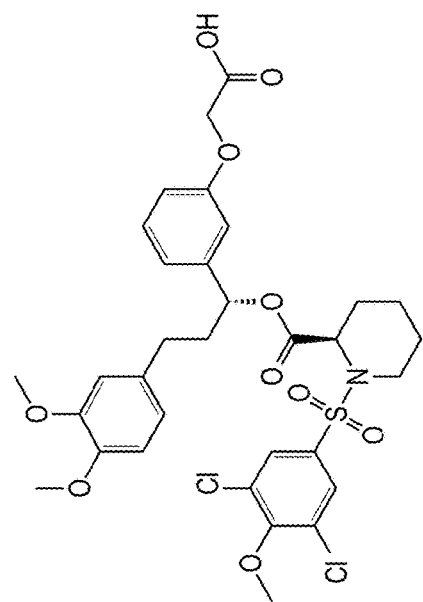
Figure 2E:
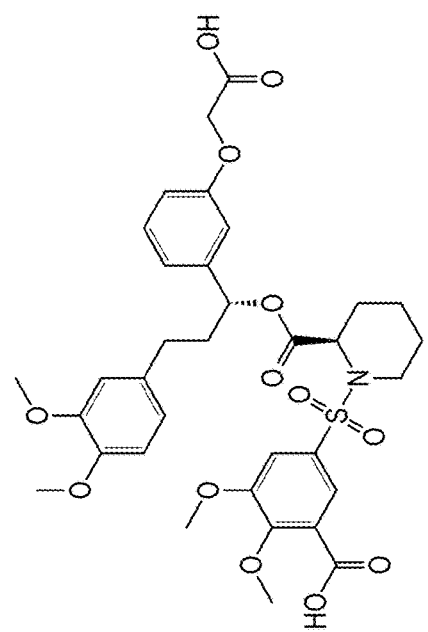
Figure 2F:
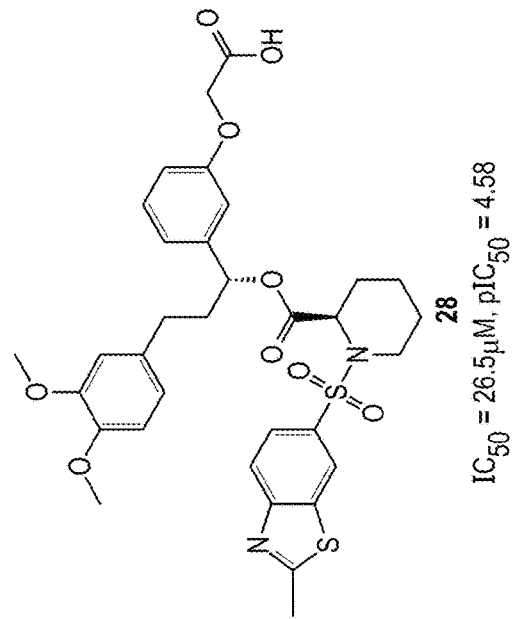
Figure 2F:
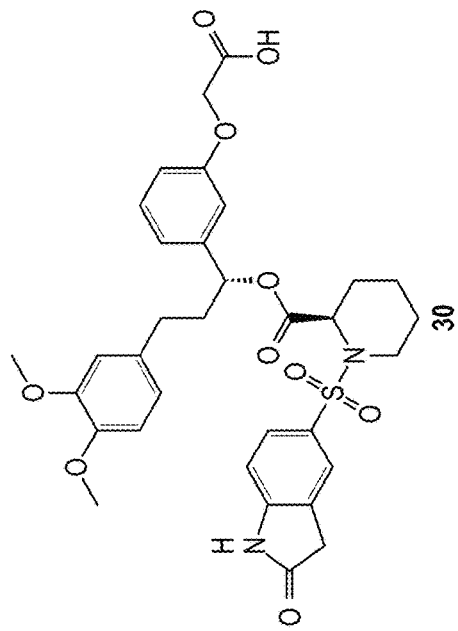
Figure 2F:
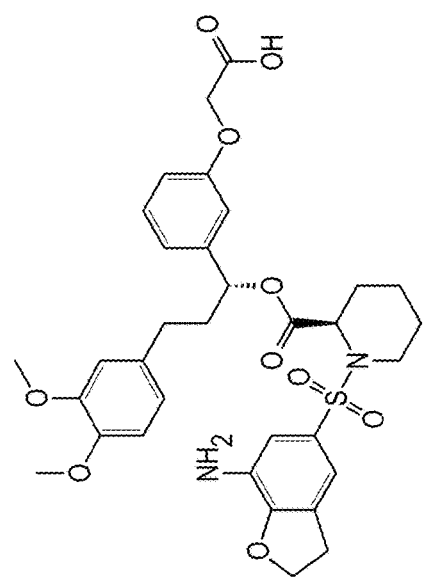
Figure 2F:
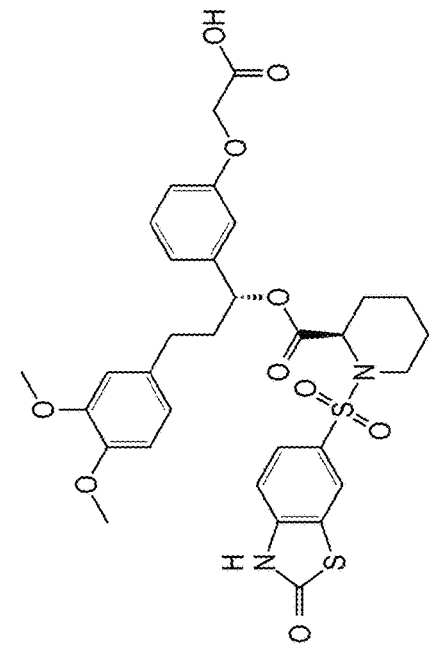
Figure 2G:
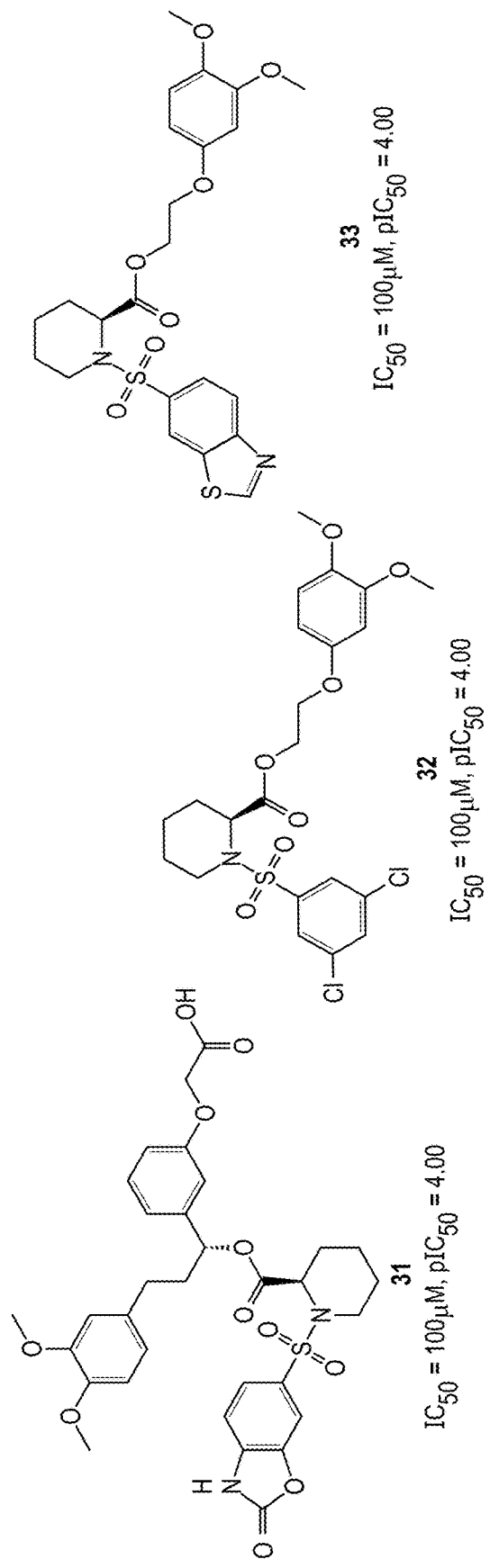
Figure 2G:
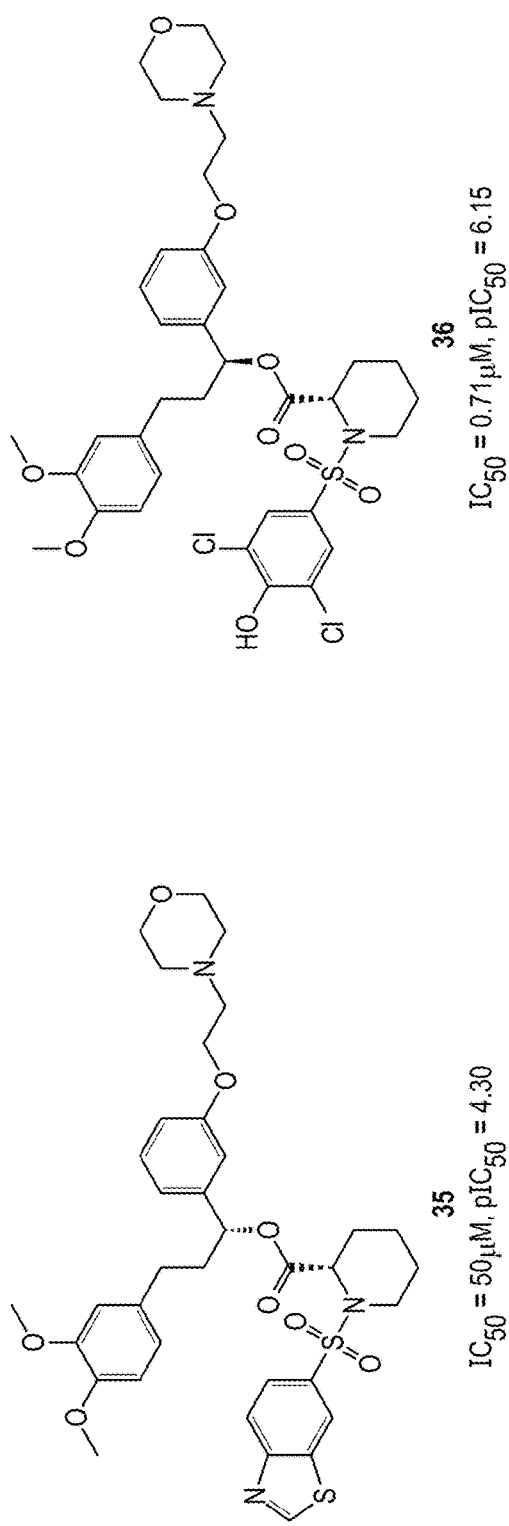
Figure 2H:
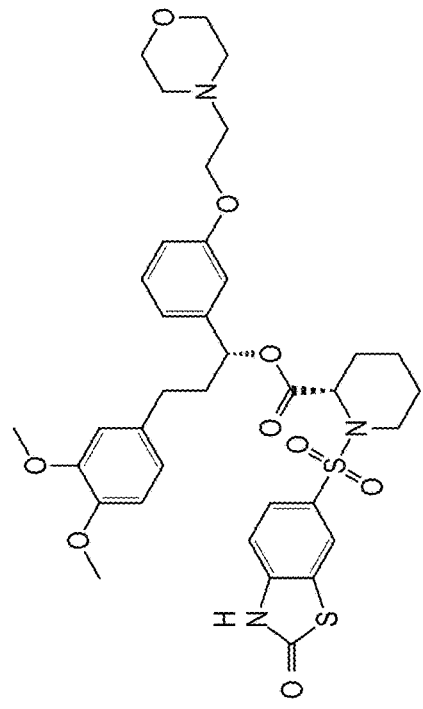
Figure 2H:
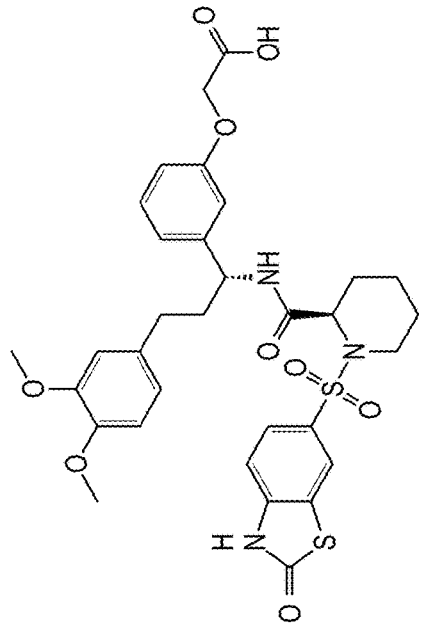
Figure 2H:
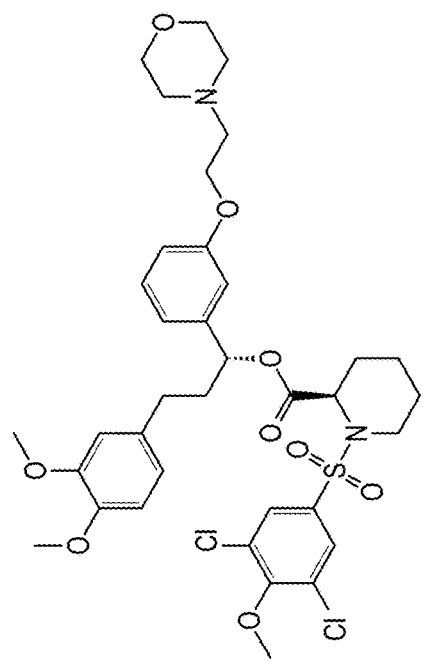
Figure 2H:
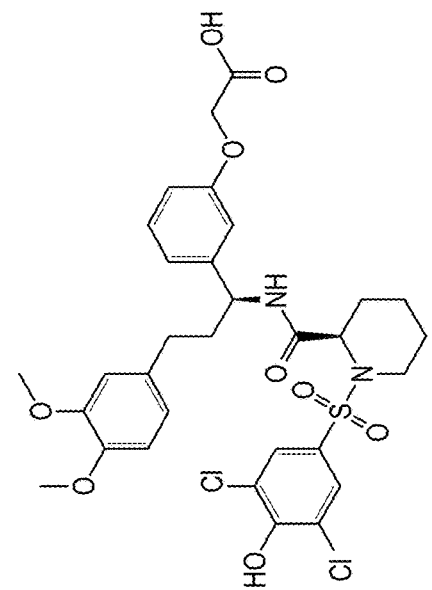
Figure 2I:
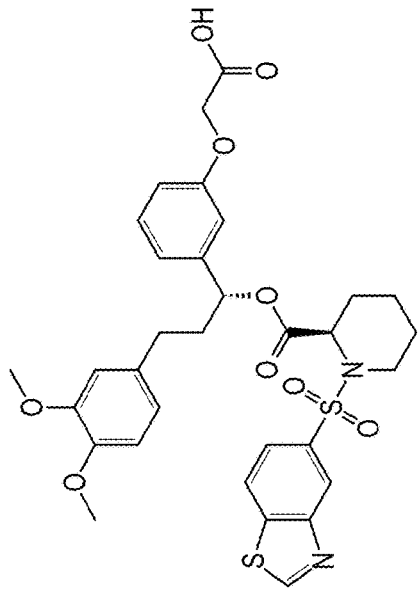
Figure 2I:
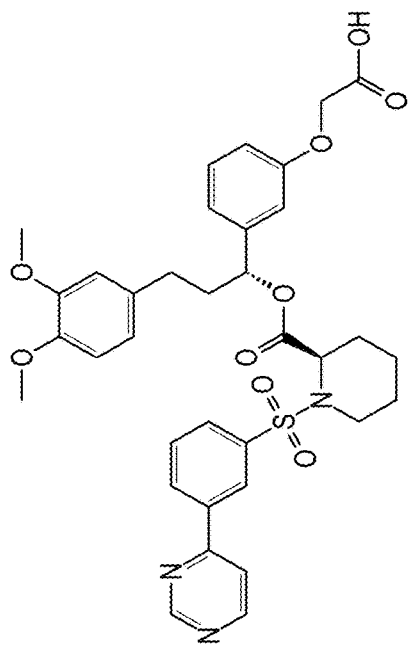
Figure 2I:
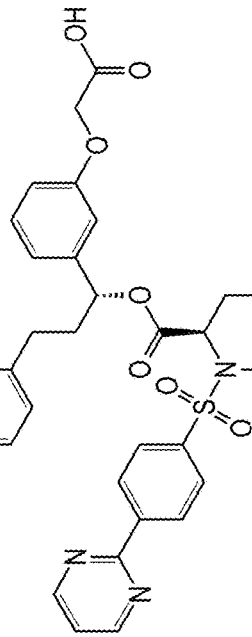
Figure 2I:
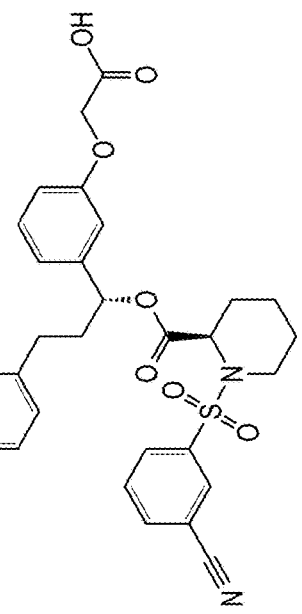
Figure 2J:
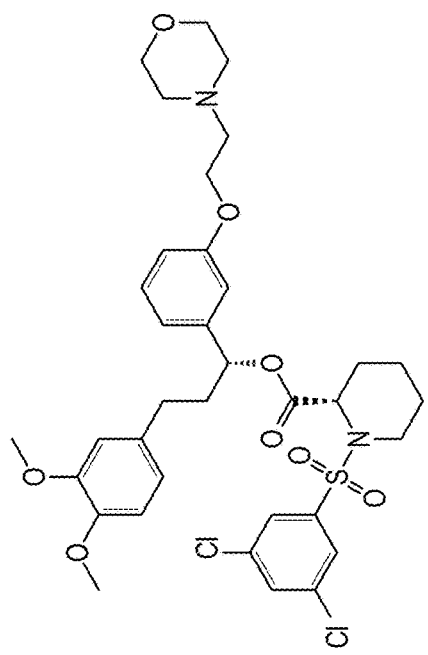
Figure 2J:
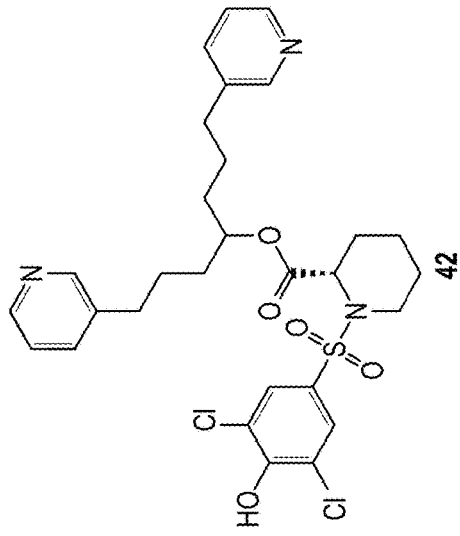
Figure 2J:
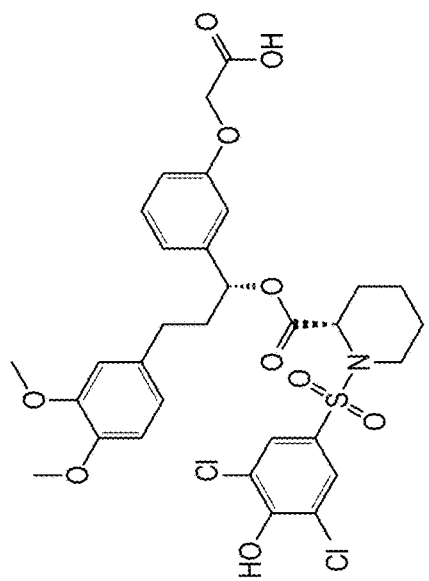
Figure 2J:
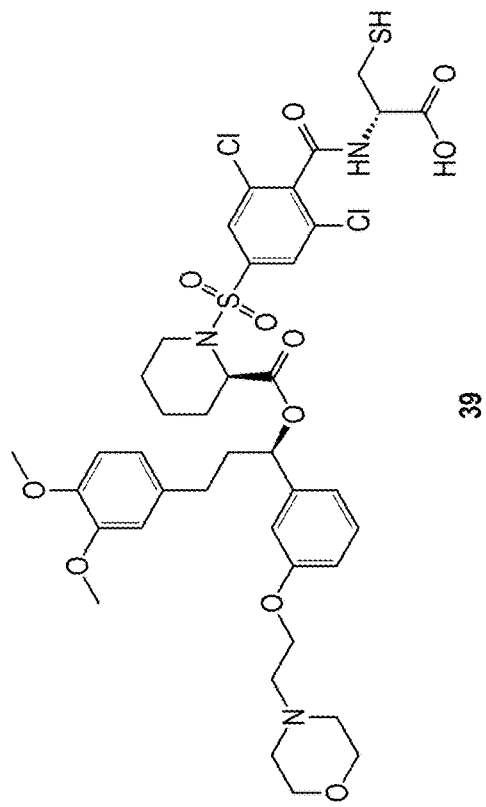

Applicants have conducted a large scale virtual screening using the crystal structure of FKBP52 for the novel hit discovery. A FKBP52 virtual screening pipeline is shown in FIG. 1. A workflow begins with database 110 and proceeds to docking analysis 120. This is followed with a Ph4 filter 130 and then QSAR model 140 analysis resulting in hits 150. However, a high quality ranking tool is needed for good hit selection. Here, Applicants are reporting CoMFA and CoMSIA models for ranking compounds of a FKBP52 virtual screening. In addition, Applicants are reporting the three hit molecules identified in the screen. In addition, Applicants show that the most potent hit, PC257, selectively inhibits the steroid hormone receptors regulated by FKBP52.

CoMFA and CoMSIA Models of FKBP52

Dataset collection: Forty-two inhibitors of pipecolate sulfonamides of the FKBP52 dataset were selected to generate CoMFA and CoMSIA models (FIGS. 2A-2J). Biological activity data were converted into $pIC_{50}$ ($-\log IC_{50}$) values, where the $IC_{50}$ of FKBP52 inhibition is represented as molar values (FIGS. 2A-2J).

Figure 3C:
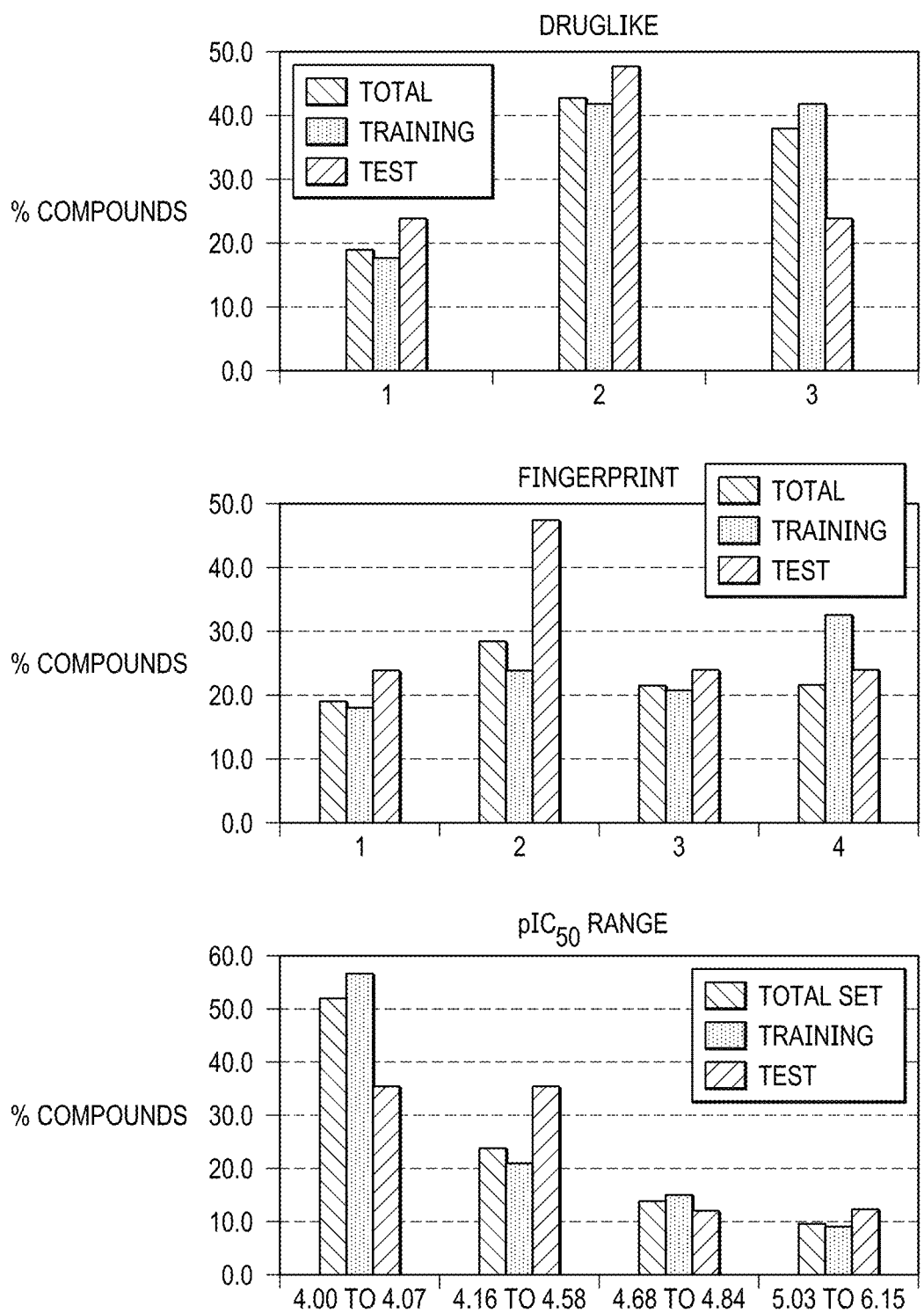

Compounds were grouped according to molecular structural diversity, drug-like properties and range of biological activity. Molecular structural diversity and drug-like properties were clustered using hierarchical cluster analysis (HCA) with the complete linkage method and Euclidian distance implemented in Chemoface. Compounds were separated into different groups according to their biological activity range in log unit (FIGS. 3A-3C). Molecular structural information was encoded from PubChem fingerprints (PF), while drug-like properties include descriptors of Log P, number of H-bond acceptors (HBA) and donors (HBD), topological surface area (TPSA), number of rotatable bonds (nRot) and molecular weight (MW) (FIG. 4). PF and descriptors were determined using PaDel descriptors and all data were normalized before HCA.

The FKBP52 dataset compounds were randomly separated into a training set of 34 compounds and a test set of 8 compounds respectively, which can represent each cluster in the total set as shown in FIGS. 3A-3C. The protonation, ionization and minimization, and flexible alignment of the compound structures were subsequently processed using MOE suite of programs.

Generating the FKBP52 CoMFA and CoMSIA Models

Figure 5A:
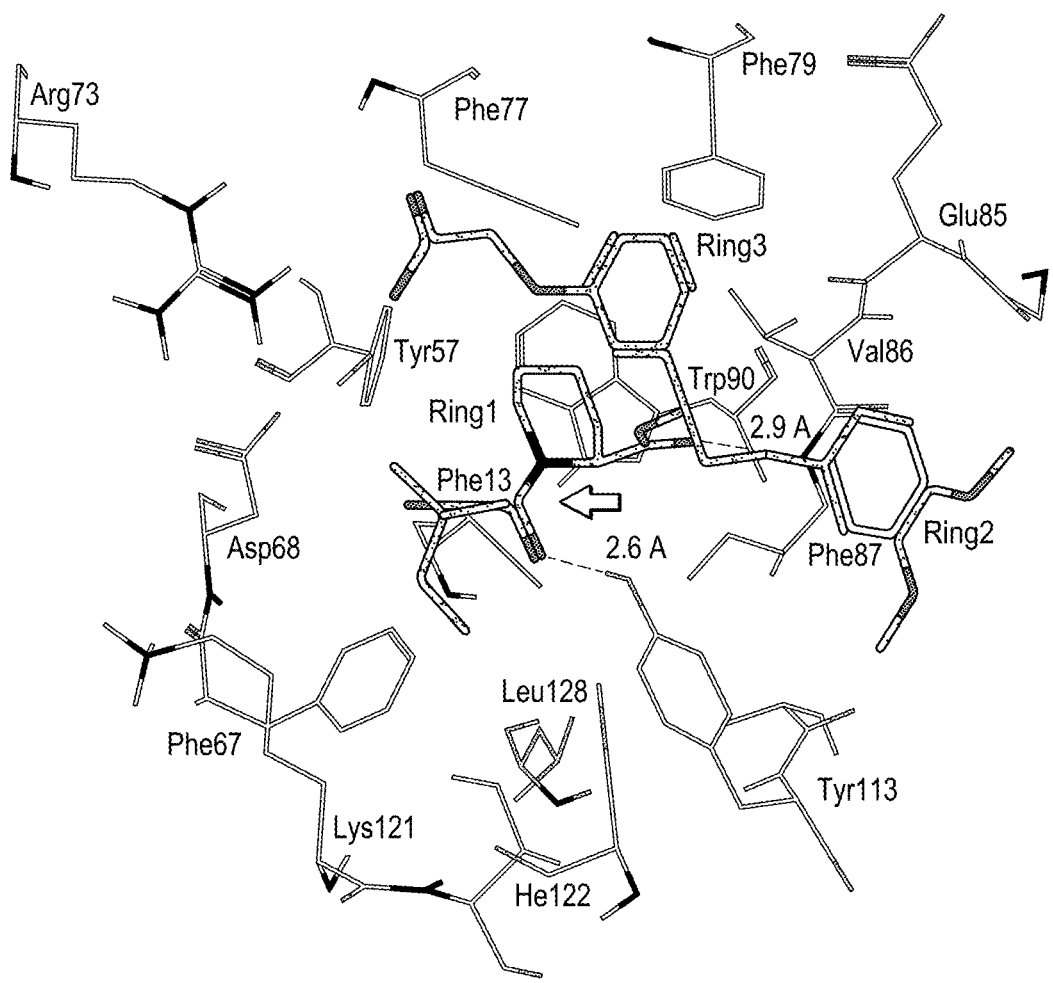
FIGS. 5A-5B depict an overview of the FKBP52 inhibitors in accordance with an illustrative embodiment.
Figure 5B:
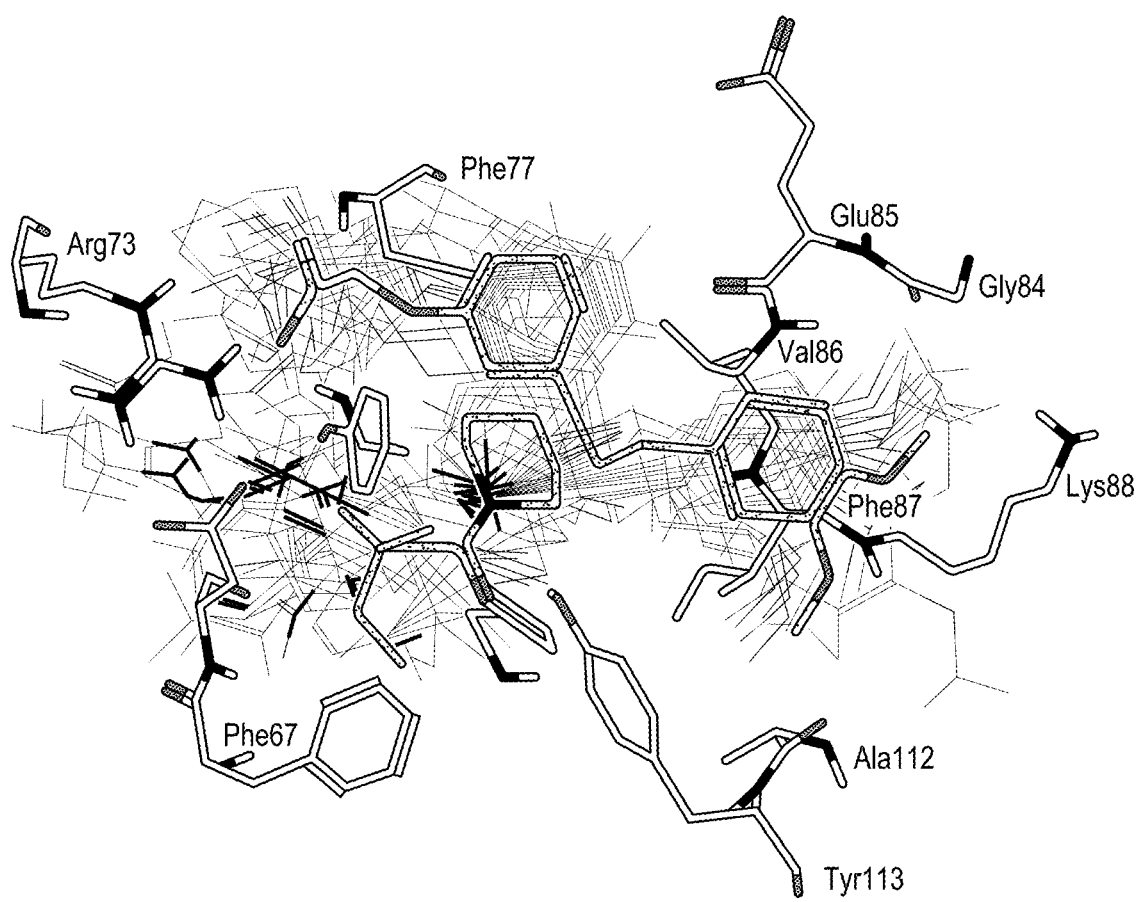
Figure 11A:
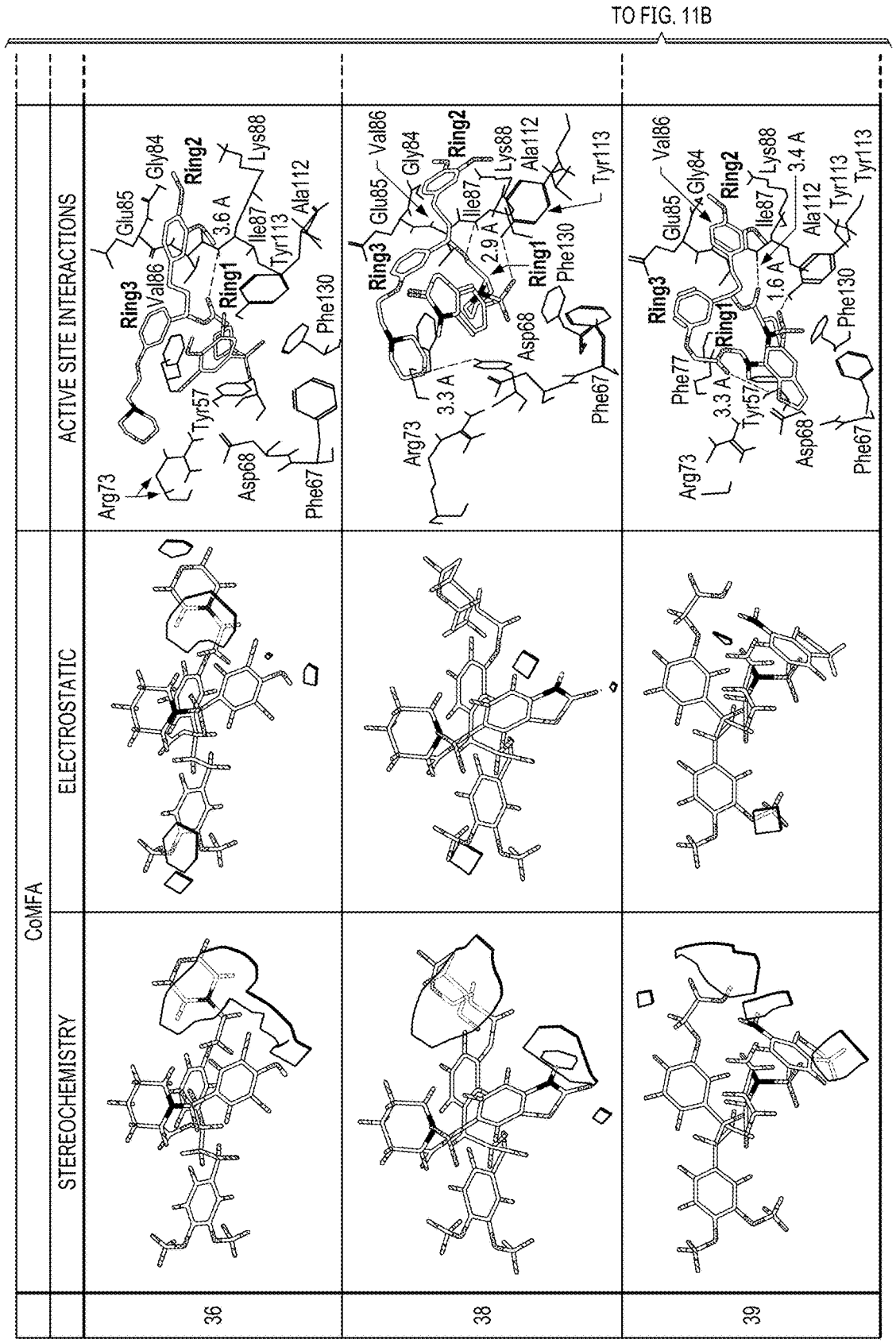
FIGS. 11A-11B and FIGS. 12A-12B present CoMFA contour maps, for steric and electrostatic terms, and CoMSIA contribution maps, highlighting the acceptor and steric contributions in accordance with an illustrative embodiment. Contour maps showed around the compounds 36, 38 and 39. Green contours represent regions where bulky groups increase biological activity while yellow contours indicate areas where bulky groups decrease biological activity. Favorable electrostatic contributions represented in blue, while unfavorable contributions to the biological activity represented in red. Favorable acceptor contributions are highlighted in pink, while unfavorable in grey. Contour maps showed around the compounds less active (6, 32 and 40) and most active (36, 38 and 39). Green contours represent regions where bulky groups increase biological activity while yellow contours indicate areas where bulky groups decrease biological activity in steric contribution.
Figure 11B:
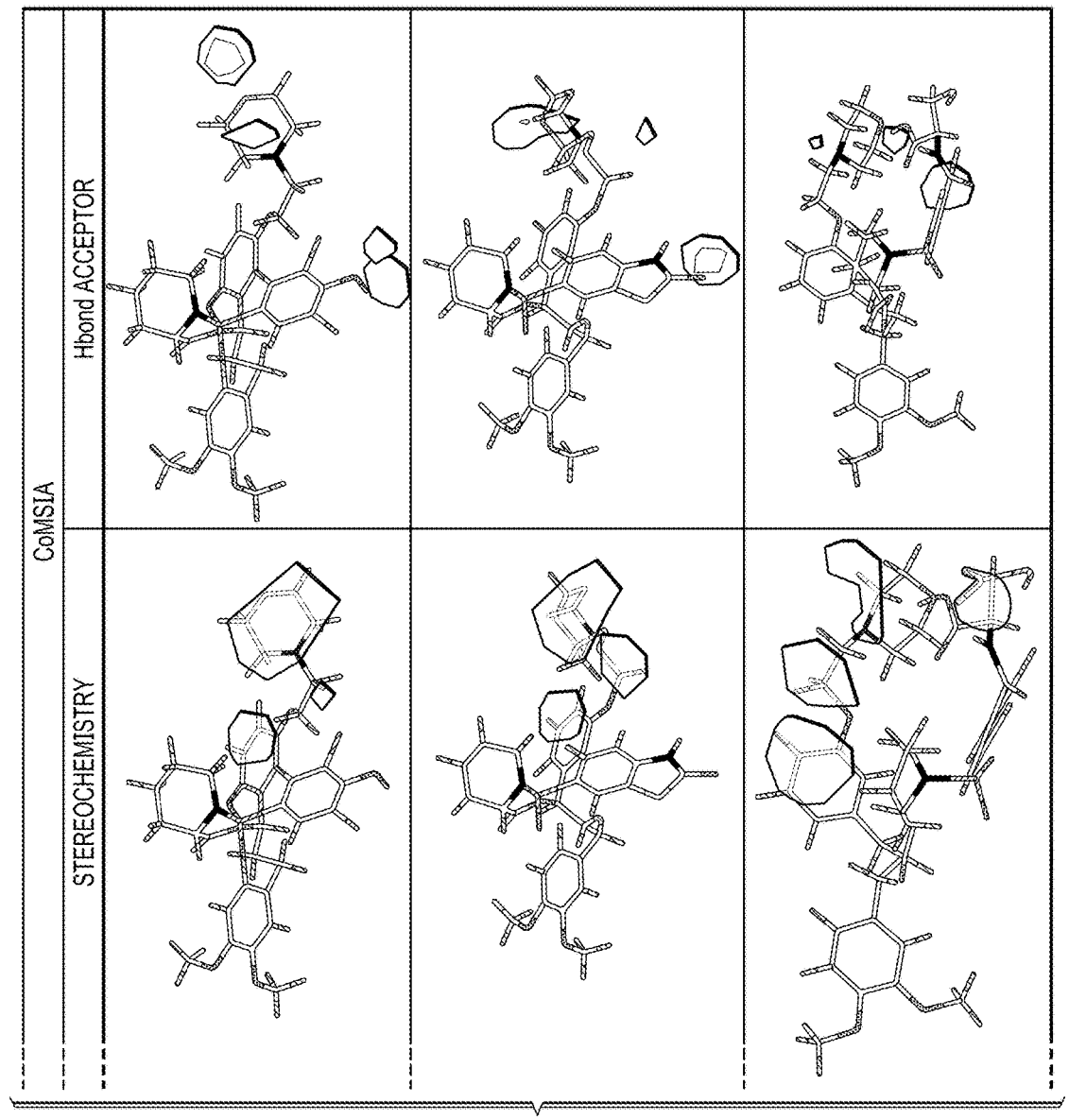
Figure 12A:
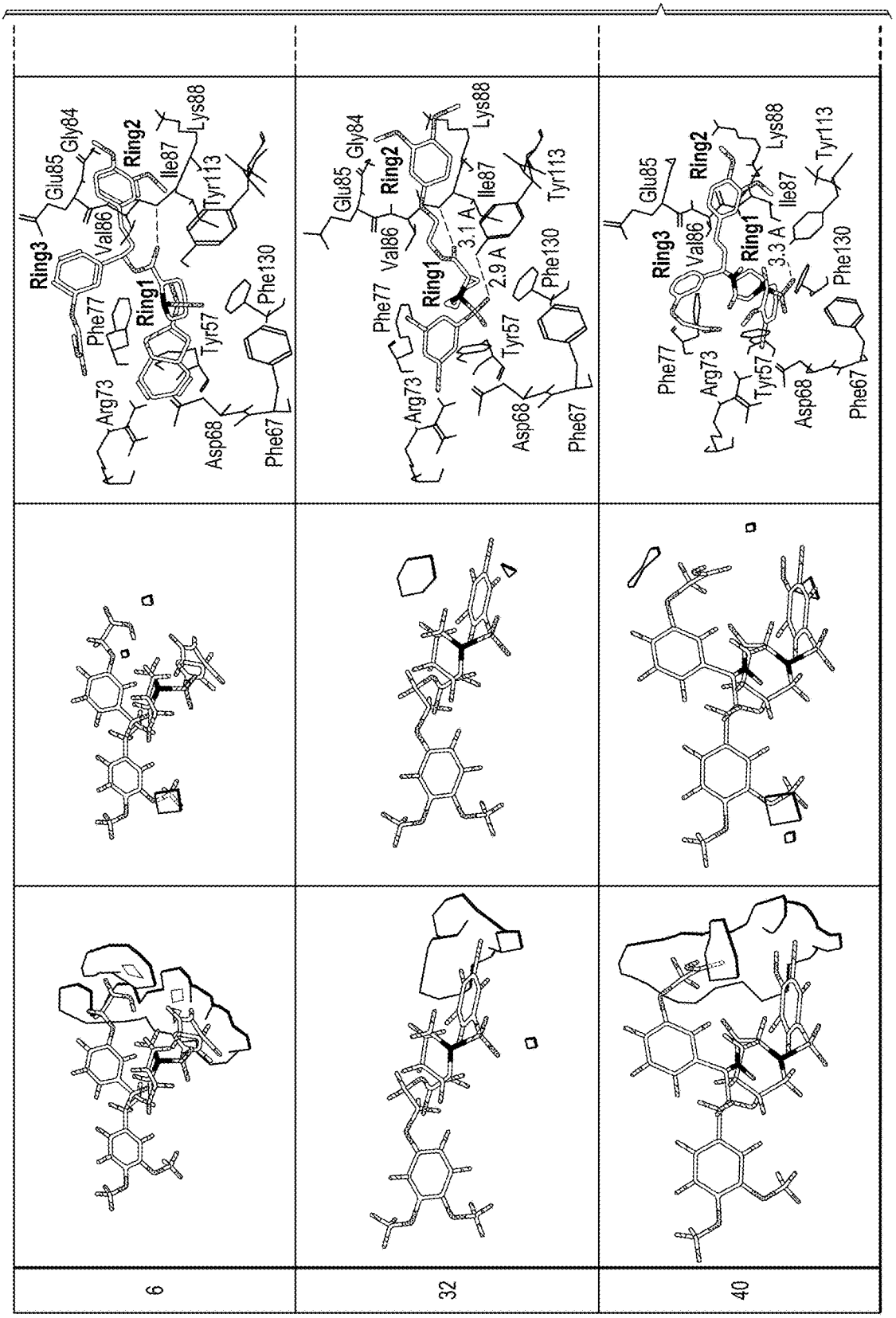
Figure 12B:
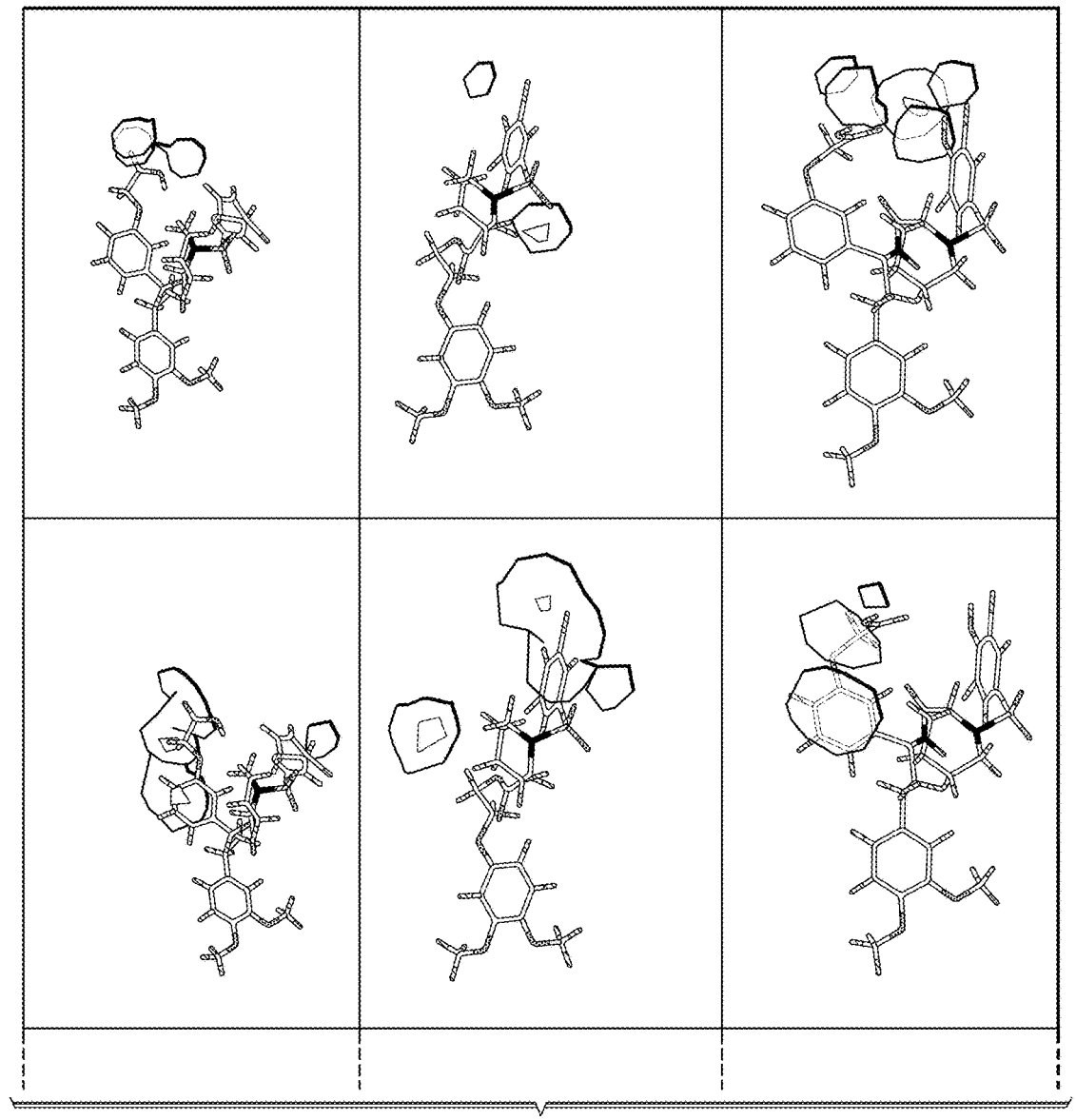

Dataset and alignment: Molecular alignment is the critical step of CoMFA and CoMSIA modelling because the three-dimensional descriptors are evaluated based on a lattice grid. The alignment of the inhibitors of the FKBP52 dataset indicates the importance of the three important rings (FIG. 5A). Ring 1 is a part of pipecolate group with a system of two H-bond donor and three H-bond acceptor which in the dataset the carbon atom between oxygen (orange arrow) was substituted by a sulfur atom (FIG. 5B). The other two aromatic ring are important for hydrophobic contacts (FIG. 5B) in the FKBP52 active site.

Models were generated using comparative molecular fields' analysis (CoMFA) and comparative molecular similarity indices analysis (CoMSIA) after alignment, respectively, using the partial least-squares (PLS) regression method implemented in Sybyl8.1 from the training set. Seventeen models of CoMFA (FIG. 6) and CoMSIA (FIG. 7) respectively were inferred by varying the standard parameter settings.

Normally, the quality of the models can be evaluated by correlation coefficients: ($q^2$ and cross-validation: $r^2$), number of principal components (PC) and others parameters such as standard error estimate (SEE) and contribution of force fields. The optimal CoMFA and CoMSIA models are the ones with minimal PC determined by cross-validation PLS regression, which are used to generate the contour maps. The intermediate models were inferred by varying the standard parameter settings as weight (0.3 to 1.5) and distance (1 to 4 Å) between the grid points. A positively charged spa carbon was used as the probe atom to calculate molecular interaction fields (CoMFA), and a positively charged spa hybridized carbon probe atom to calculate a range of different similarity indices (CoMSIA); and the molecular alignment of training set molecules with an initial grid spacing of 2 Å and an energy cut-off of 30 kcal/mol was used to generate the CoMFA and CoMSIA models. The molecular interaction field was calculated using the probe atom, and the steric and electrostatic interactions with training set compounds were calculated using Lennard-Jones and Coulomb energy terms of the CoMFA model. The different combinations of similarity indices of steric, electrostatic, hydrophobic, H-bond donor and H-bond acceptor were calculated in the CoMSIA model, and the best combination for the best model was determined when the highest $q_{LOO}^2$ among the pairs of indices was further optimized using focus approach that changes either the grid spacing from 1 to 4 Å by a step of 0.5 multiplied by the original distance or the weight factor from 0.3 to 1.5 by a step of 0.2 multiplied by the standard deviation (SD) of the original model.

Varied combinations of weight factor and grid spacing were employed to generate the intermediate models which were ranked by $Q_{LOO}^2$ values to obtain the best model. The maximum number of principal components (PCs) used in both the CoMFA and the CoMSIA models respected the size of the dataset (42 compounds) that each intermediate model takes the least number of PCs sufficient to explain the variability of the system (FIGS. 6 and 7).

Figure 13A:
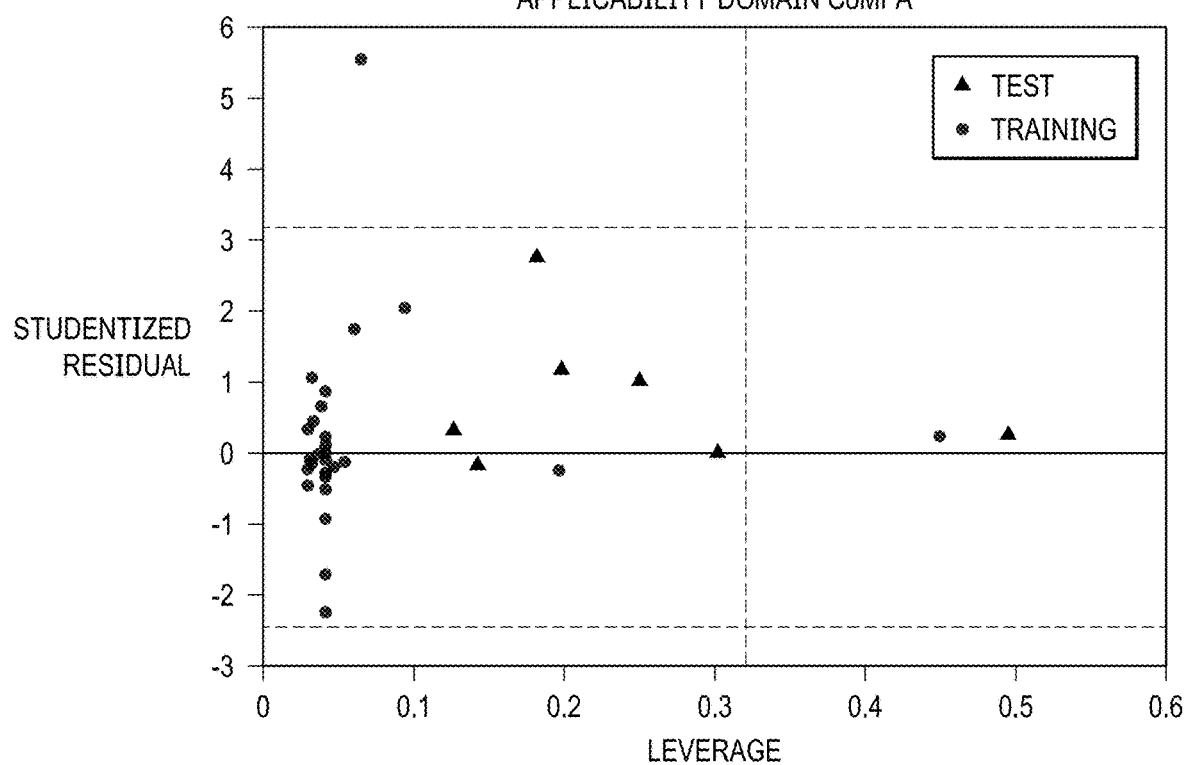
FIGS. 13A-13B depict plots of leverage versus studentized residuals for (FIG. 13A) CoMFA and (FIG. 13B) CoMSIA: black dots represent training set and black triangles represent test set in accordance with an illustrative embodiment.
Figure 13B:
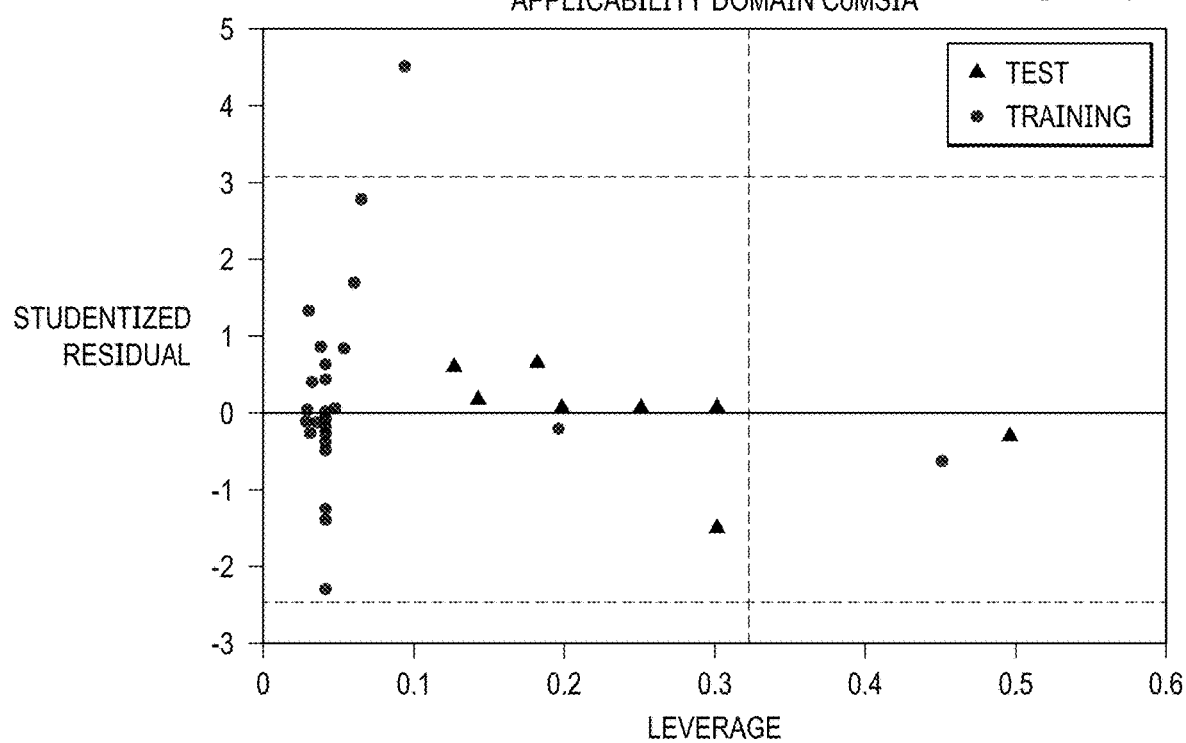

The best models of CoMFA and CoMSIA respectively were selected by the internal robustness ($q_{LOO}^2>0.6$) and external robustness ($Q_{F2}^2$ and $Q_{F3}^2>0.7$), which were used to generate contribution and contour maps for the most and least active and selective compounds. Additional external validation metrics of $r_m^2$, which compares the correlation coefficients in the prediction of the test set when passing through the origin ($r_0^2$) were evaluated to assess the model's predictability. Detailed description of these metrics can be found in a comprehensive review. The sensitivity index ($dq^2/dr^{2yy'}$) was generated by 50 runs of progressive scrambling CoMFA and CoMSIA, the values of what should be between 0.8 and 1.2 (FIGS. 8 and 9). Applicability domain in FIGS. 13A-13B showed that 93% of the training and test set compounds are inside the predictability domain of the left-bottom dashed-lined quadrant of leverage and studentized residual.

Validation of Models

The selected CoMFA and CoMSIA models need to be cross-validated for the activity prediction of new compounds such as filter in virtual screening. CoMFA have steric (S) and electrostatic (E) fields while CoMSIA presents additional contributions of hydrogen bonds (donor (D) and acceptor (A)) and hydrophobic (H) fields, which provide more information about structural modification. In relation to force fields calculated by CoMFA and CoMSIA and to the combination of CoMFA and CoMSIA, the CoMFA model and CoMSIA model should be built by partial least square (PLS) and validated by cross validation.

Normally, the optimal models are determined by the internal correlation coefficients of $q^2$ and cross-validation $r^2$ and the number of principle components (NP). Other parameters of a model can be calculated, such as standard error estimate (SEE) and contribution of force fields. Thus, the best models are constructed with optimal NP by cross-validation PLS regression, which are used to generate the contour maps.

After that, the contour maps of the models are analyzed and the biological activities of the training and test sets are predicted. In addition, the Y-randomization is applied to ensure the robustness of the models to repeat the model training procedure several times by randomly shuffling the activities in the training set. The lowest $q^2$ and $r^2$ values built with randomized activities indicate that the constructed models are acceptable and reliable.

It has been shown that CoMFA and CoMSIA have been used to investigate the SAR. Therefore, Applicants have constructed CoMFA and CoMSIA models of FKBP52, and generated the counter maps of CoMFA and CoMSIA that can be used for hit selection of FKBP52 VS after docking.

External Validation and Model Selection

Figure 14A:
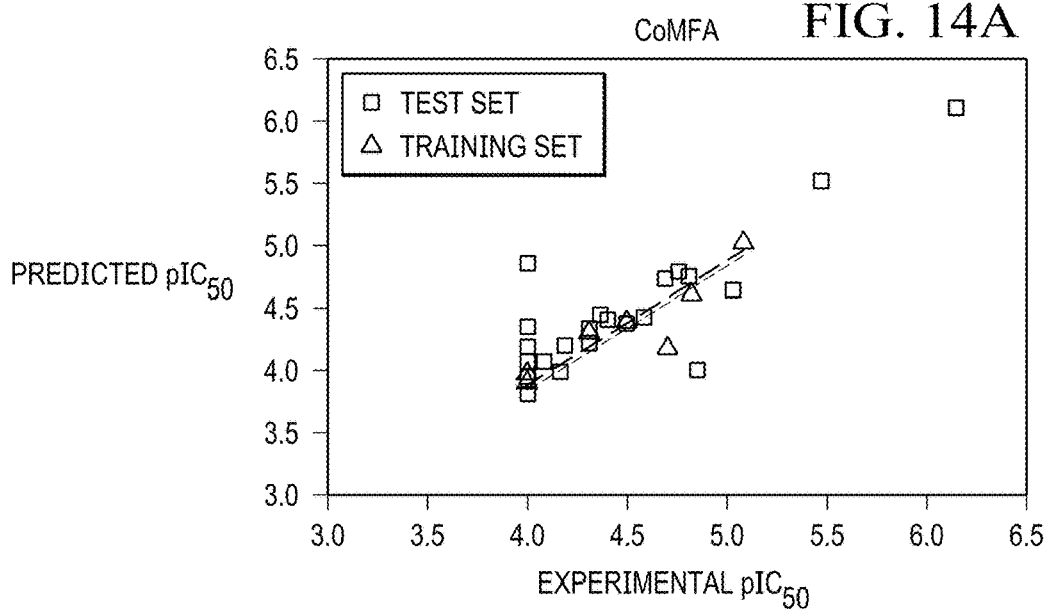
FIGS. 14A-14C depict experimental and predicted values of $pIC_{50}$ for the training and test sets in accordance with an illustrative embodiment.
Figure 14B:
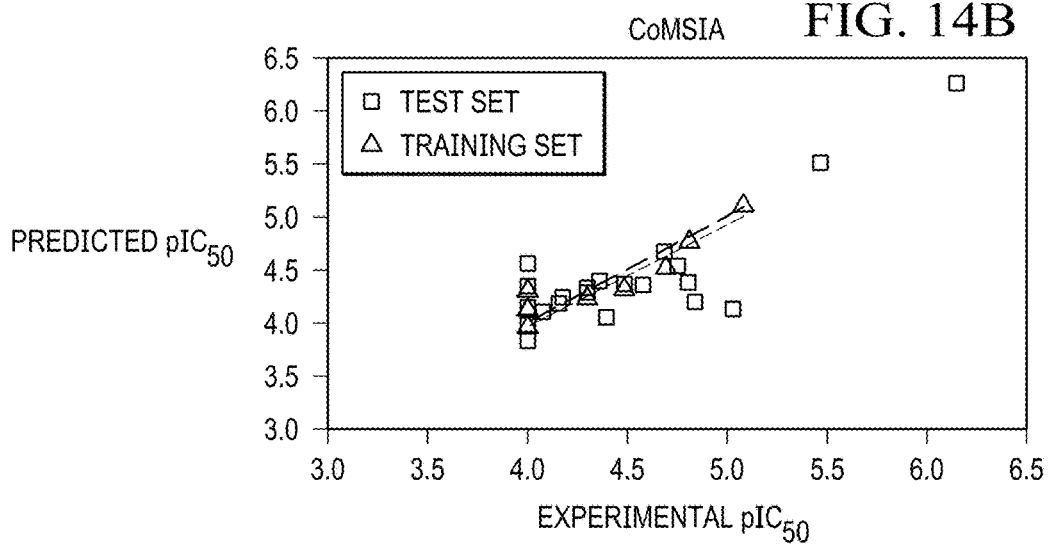
Figure 14C:
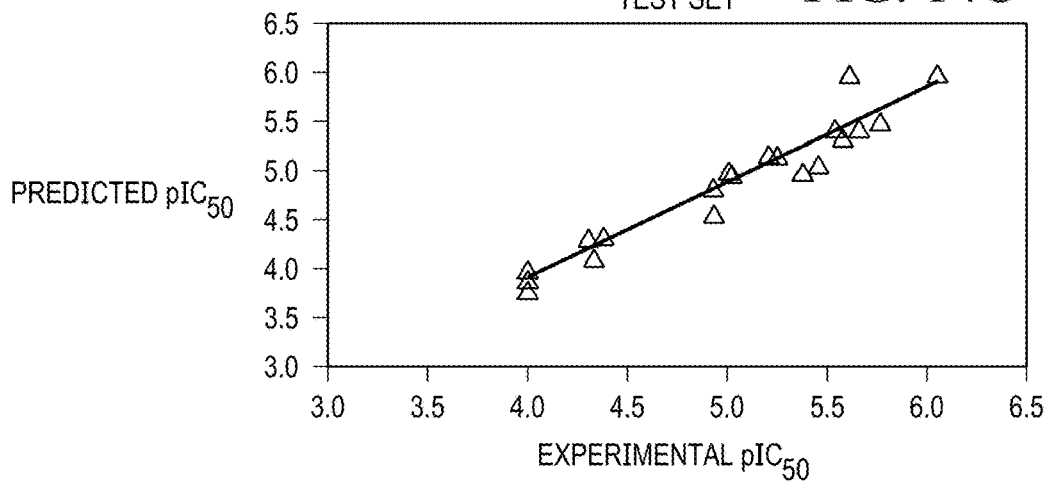

The CoMFA and CoMSIA models were satisfactory with values within the specifications and according to OECD guidelines. The models are good as indicated by their $r_{pred}^2$ values of >0.7 (FIGS. 14A and 14B, as a graphical representation) and low root-mean-square error of prediction (RMSEP) rates (FIG. 10). Thus another external test set of 22 compounds of pipecolate derivatives were curated and their activities were predicted by CoMSIA model (FIG. 14C and FIG. 15).

The high $Q_{F2}^2$ and $Q_{F3}^2$ values suggest that the CoMSIA model has high predictability of FKBP52 inhibition. Additionally, the small discrepancy between predicted and observed activity can be demonstrated by $r_m^2$, which is also bigger than 0.60. Residuals were always smaller than 1 and showed no correlation with predicted values (FIG. 16).

Figure 17:
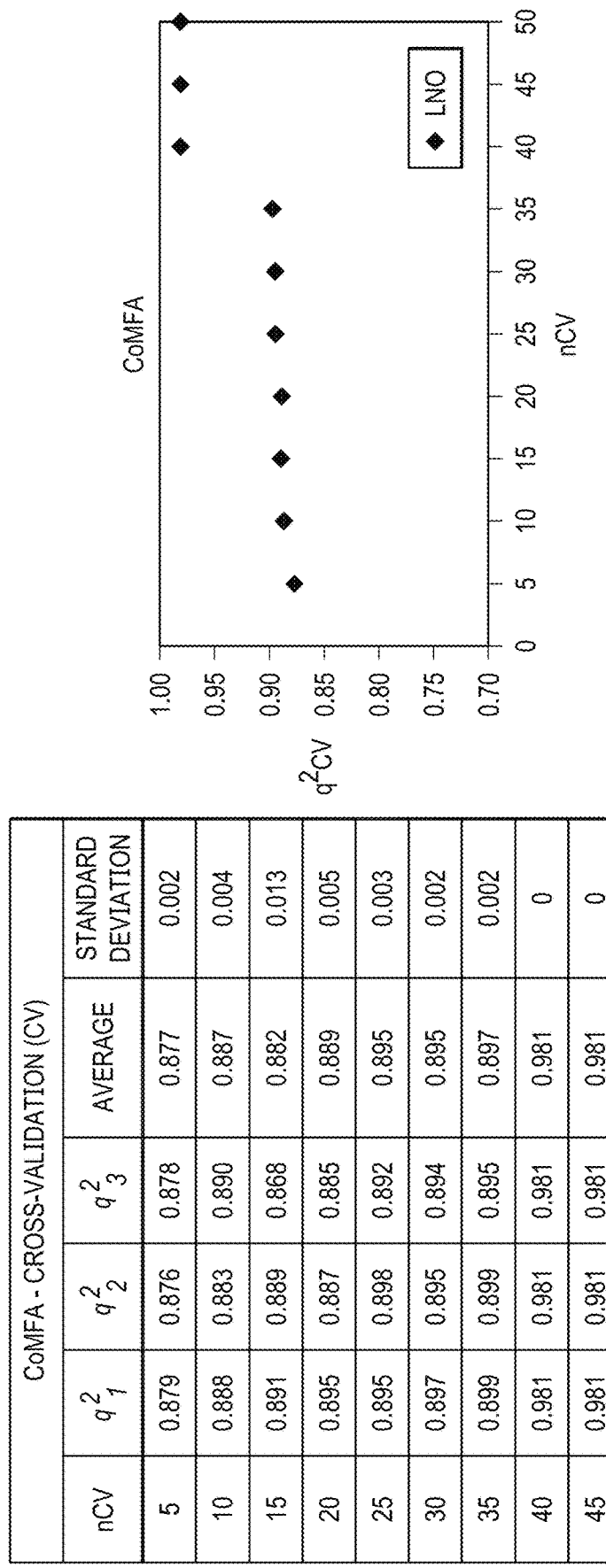
FIG. 17 presents results from the cross-validation (LNO) for the CoMFA model and a plot obtained from robustness test-cross-validated results (LNO). $n_{CV}$=number of groups; $q^2_{CV}$=average of cross-validated $q^2$ in accordance with an illustrative embodiment.
Figure 18:
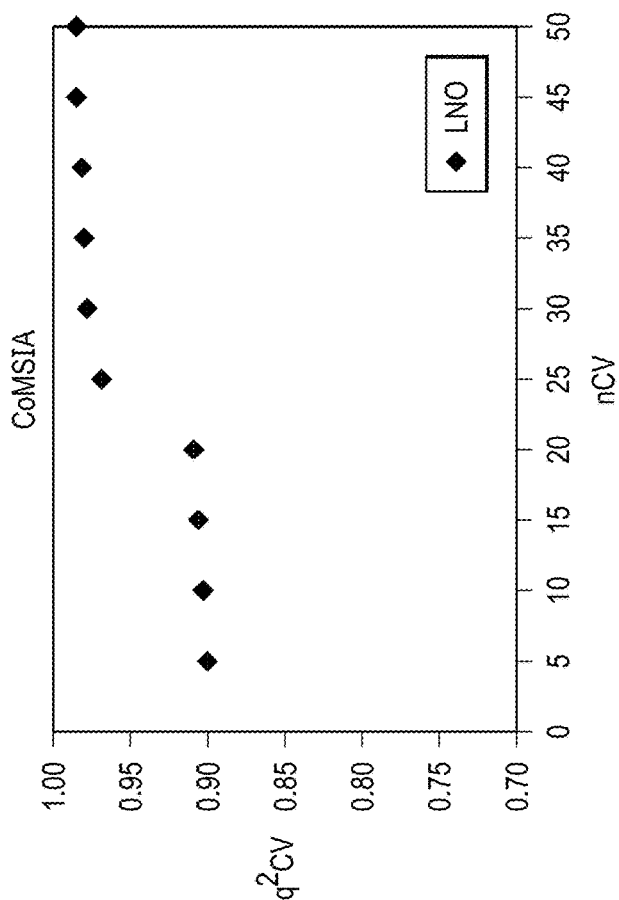
FIG. 18 presents results from the cross-validation (LNO) of the CoMSIA model and a plot obtained from robustness test-cross-validated results (LNO) in accordance with an illustrative embodiment. $n_{CV}$=number of groups; $q^2_{CV}$=average of cross-validated $q^2$

In order to test the robustness and stability of the models against variation of the training set composition, Applicants also performed a leave-N-out (LNO) validation (FIGS. 17 and 18), with cross-validation group numbers varying from 5 to 50 and the average $q^2$ values are bigger than 0.8 indicating a great internal consistency.

Physicochemical Interpretation of Models

Although CoMFA and COMSIA models complement each other, CoMSIA often behaves better than CoMFA, because CoMSIA model is trained with a lot more chemical information of the training dataset. To evaluate the quality of CoMFA and CoMSIA models, it is necessary to perform both internal and external validation. In particular, if hydrophobic, acceptor and donor contributions are important for the dataset, it is more likely that CoMSIA performs better than CoMFA which only considers two descriptors of electrostatic and steric.

The internal and external validation results in FIG. 10 of FKBP52 showed that CoMSIA is more predictive than the CoMFA, because acceptor of the data set (FIG. 9) is a strong contribution. Thus, the CoMSIA contour map in FIGS. 11A-11B and 12A-12B should be used to evaluate different chemical cores and substitutions to optimize or select FKBP52 inhibitors.

The hydrogen acceptor maps in FIGS. 11A-11B and 12A-12B show that the bottom small purple volume of the carboxylic acid of compound 36 and of the dichlorophenol of compounds 38 and 39 reinforces the importance of the hydrogen acceptor that interacts with the active site. In contrast, the large green maps around the morpholine group of compounds 36, 38 and 39 reveal the importance of the bulky hydrophobic groups; and the purple maps highlight the favorable hydrogen acceptor contributions to the potential hydrogen acceptors of the binding site.

The yellow maps of the phenoxyacetic acid in compound 40 and of the phenoxyacetic acid and benzothiophene of compound 6 in FIGS. 11A-11B and 12A-12B suggest unfavorable steric clash with the binding site. The yellow maps of the pyrrolidine group of compound 32 also suggests that the mitigation of the steric clash is critical to boost the biological activity.

By the CoMFA model (FIGS. 11A-11B and 12A-12B), only small blue contour maps present in all compounds, which suggest just favorable contributions of the electrostatic contributions which can be explained by a low number electrostatic contribution E of 0.207 in FIG. 8. From a complementary CoMSIA field analysis, substitutions of hydrogen-bond acceptor in the blue map regions should enhance biological activity.

Since the FKBP52 CoMSIA model is highly predictive, Applicants have applied the model to rank the docking-predicted FKBP52 binding poses of ZINC15 compounds. 106 hits were selected from the VS by the FKBP52 CoMSIA ranking and visual check. Seven active compounds have been confirmed. The most active compound found has a $IC_{50}$ of approximately 1 µM, which is a magnitude better than the co-crystalized ligand ($IC_{50}$=10.5 µM)[9].

The CoMFA and CoMSIA results showed that CoMSIA model is more predictive than CoMFA, which provides a good ranking tool to select FKBP52 VS hits.

Figure 19A:
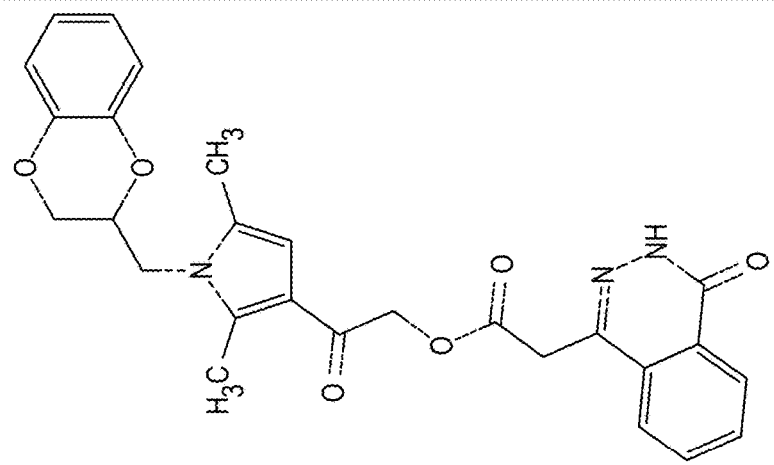
FIGS. 19A-19B depict identification of novel FKBP52-specific hit compounds in accordance with an illustrative embodiment. Structure-based drug design methodology and in silico library screening was used to identify 107 molecules targeting the FKBP52 PPIase pocket. Molecules were assessed for the ability to inhibit AR-mediated luciferase expression at a single high concentration (25 μM) in MDA-kb2 cells. Molecules that showed inhibition at 25 μM were assessed in full dose response curves to determine the IC50. MDA-kb2 cells were treated with 200 pM DHT with a range of derivative concentrations. Molecules in the low μM range will be tested in GR-, PR- and ER-Mediated luciferase assays in order to assess GR-dependent activity, PR-dependent activity and to test the effects of ER-regulated activity. A detailed evaluation of all candidate molecules will be tested in multiple cellular and animal models of prostate cancer.
Figure 19B:
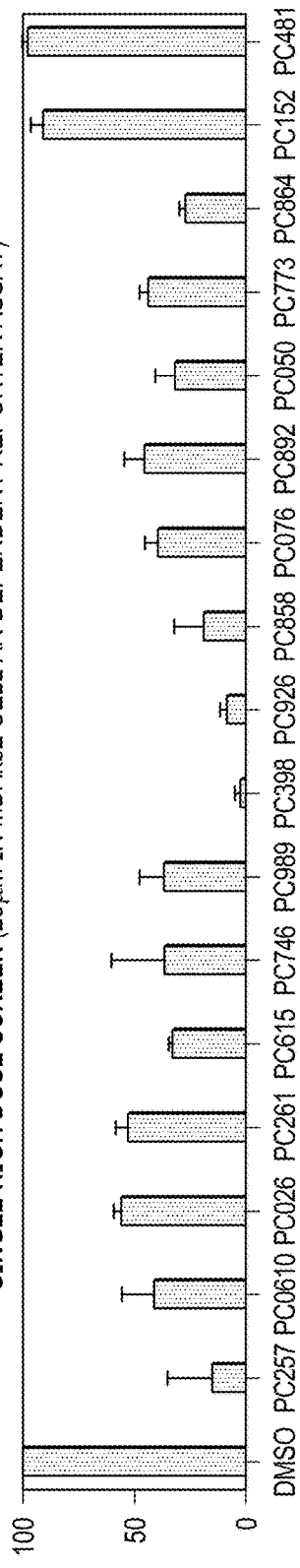
Figure 19B:
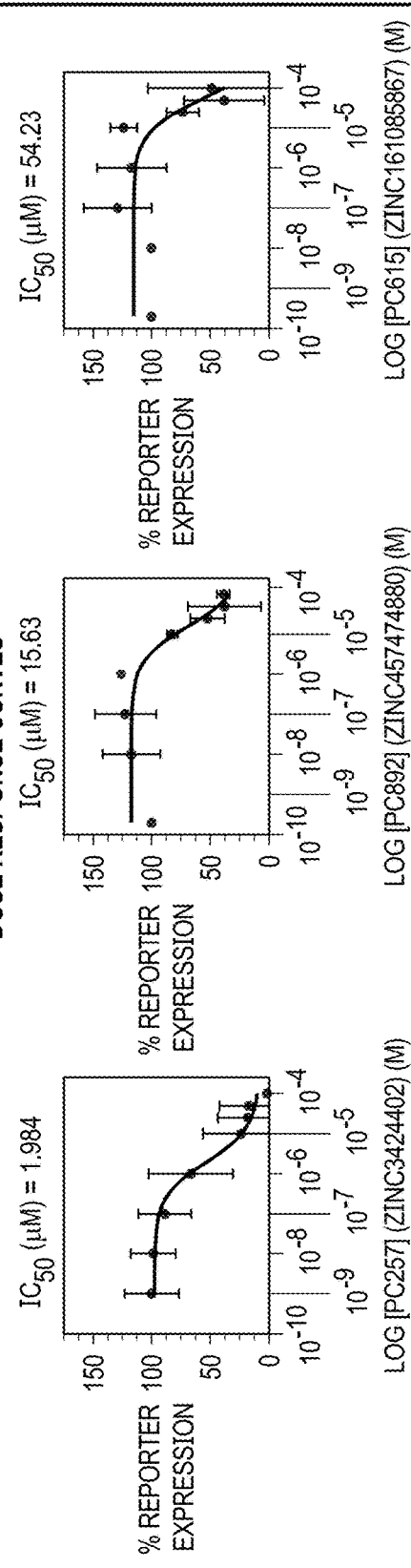
Figure 20C:
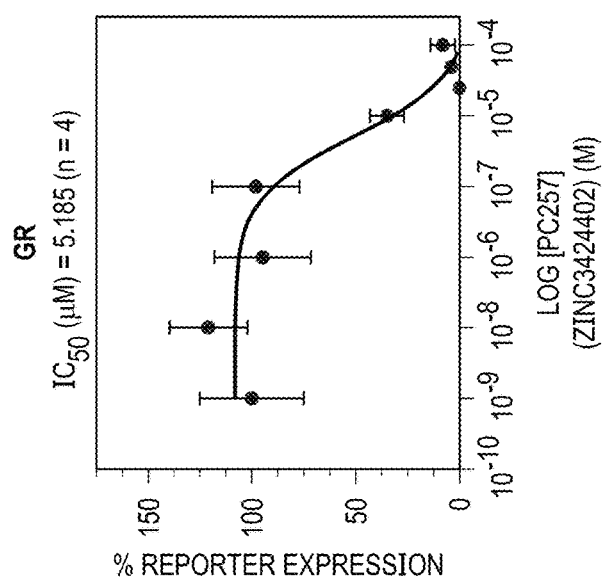
FIGS. 20A-20D depict PC257 (ZINC3424402) which inhibits FKBP52-Specific AR, GR and ER-Mediated Activity in accordance with an illustrative embodiment.
Figure 20D:
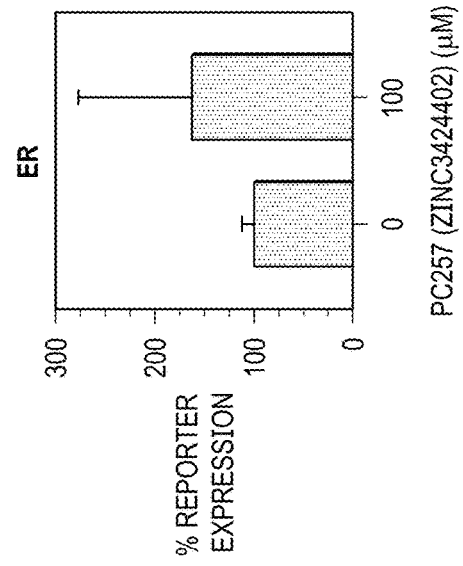
Figure 20B:
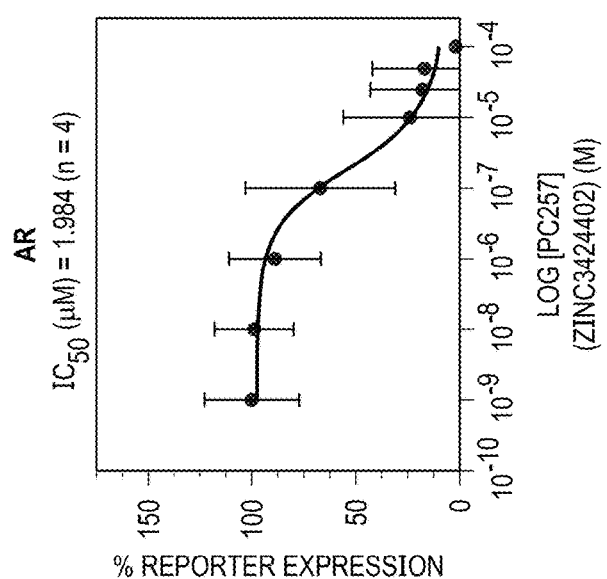
Figure 20A:
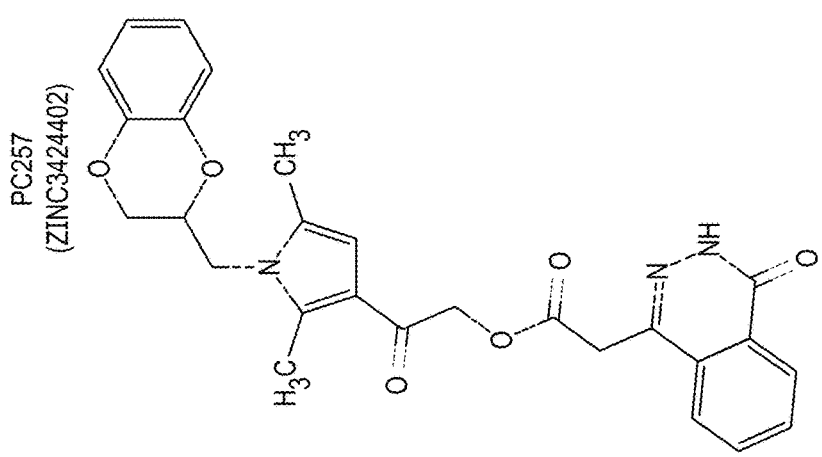

Functional Screening of Virtual Hits: Identification PC257, 615, and 892 as Next Generation FKBP52 Inhibitors An in silico structure-based drug design identified 107 hits for functional screening. As detailed in FIGS. 19A-19B, Applicants first screened these molecules at a single high dose (25 µM) for inhibition of AR activity in MDA-kb2 cell reporter assays. Any analogs that inhibited AR activity by 75% or more were then screened on full dose response curves to determine the IC50. From these data, Applicants identified 3 hits that displayed inhibition of AR activity in the low micromolar range, with PC257 (ZINC3424402) being the most potent with an IC50 of 2 µM. As previously mentioned FKBP52 functionally potentiates AR, GR and PR activities but does not potentiate ER. This is the result of the cochaperones proline-rich loop overhanging the PPIase catalytic pocket in the FK1 domain which is responsible for the regulation of receptor activity.

As detailed in FIGS. 20A-20D, Applicants predict that PC257 (ZINC3424402) binds to the FKBP52 pocket resulting in a conformational change of the proline-rich loop disrupting its interaction with receptors, in which case displaying FKBP52-specific inhibition of AR, GR and PR but not ER activity. Applicants previously demonstrated that PC257 (ZINC3424402) displayed inhibition of AR activity in the low micromolar range. As a result, Applicants wanted to show that PC257 (ZINC3424402) displayed inhibition of GR activity but does not show inhibition of ER activity. Further testing will be conducted in order to show that PC257 (ZINC3424402) inhibits PR activity. The other two hits PC892 (ZINC457474880) and PC615 (ZINC161085867) will go through the same process as PC257.

Figure 21:
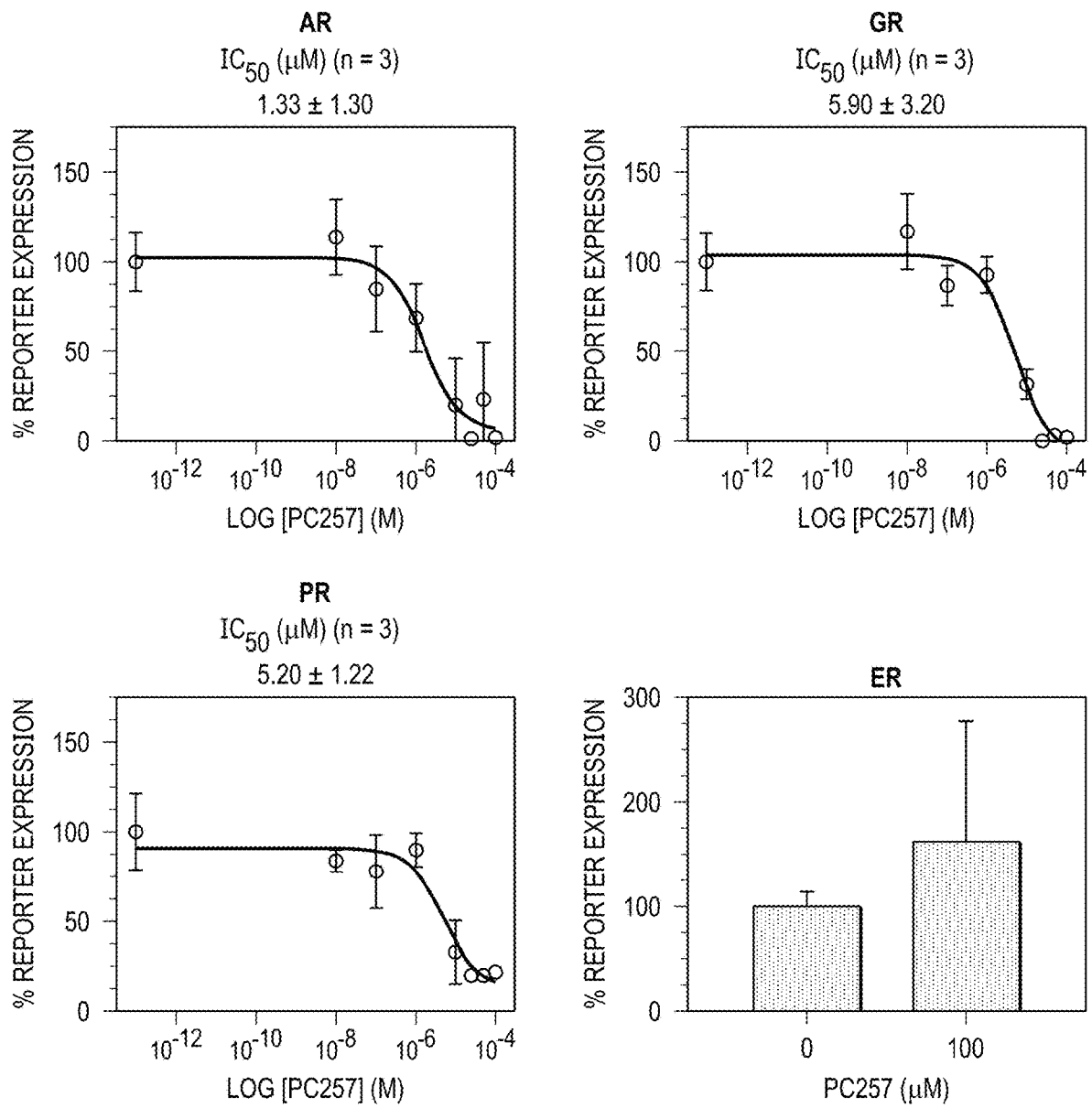
FIG. 21 depicts that PC257 specifically abrogates AR, GR and PR-dependent reporter gene expression in accordance with an illustrative embodiment.

Referring to FIG. 21, hormone-induced, receptor-dependent luciferase reporter gene expression was assessed in the presence of a range of PC257 concentrations for androgen receptor (AR) and glucocorticoid receptor (GR) in MDAkb2 cells, and for progesterone receptor (PR) and estrogen receptor (ER) in T47D cells. The IC50 values for AR, GR and PR inhibition are shown. These data indicate that PC257 specifically abrogates AR, GR and PR activity, which are known to be regulated by FKBP52, but has no inhibitory activity on ER; a receptor that is not regulated by FKBP52. This strongly suggests that PC257 directly targets the FKBP52 protein.

Figure 22:
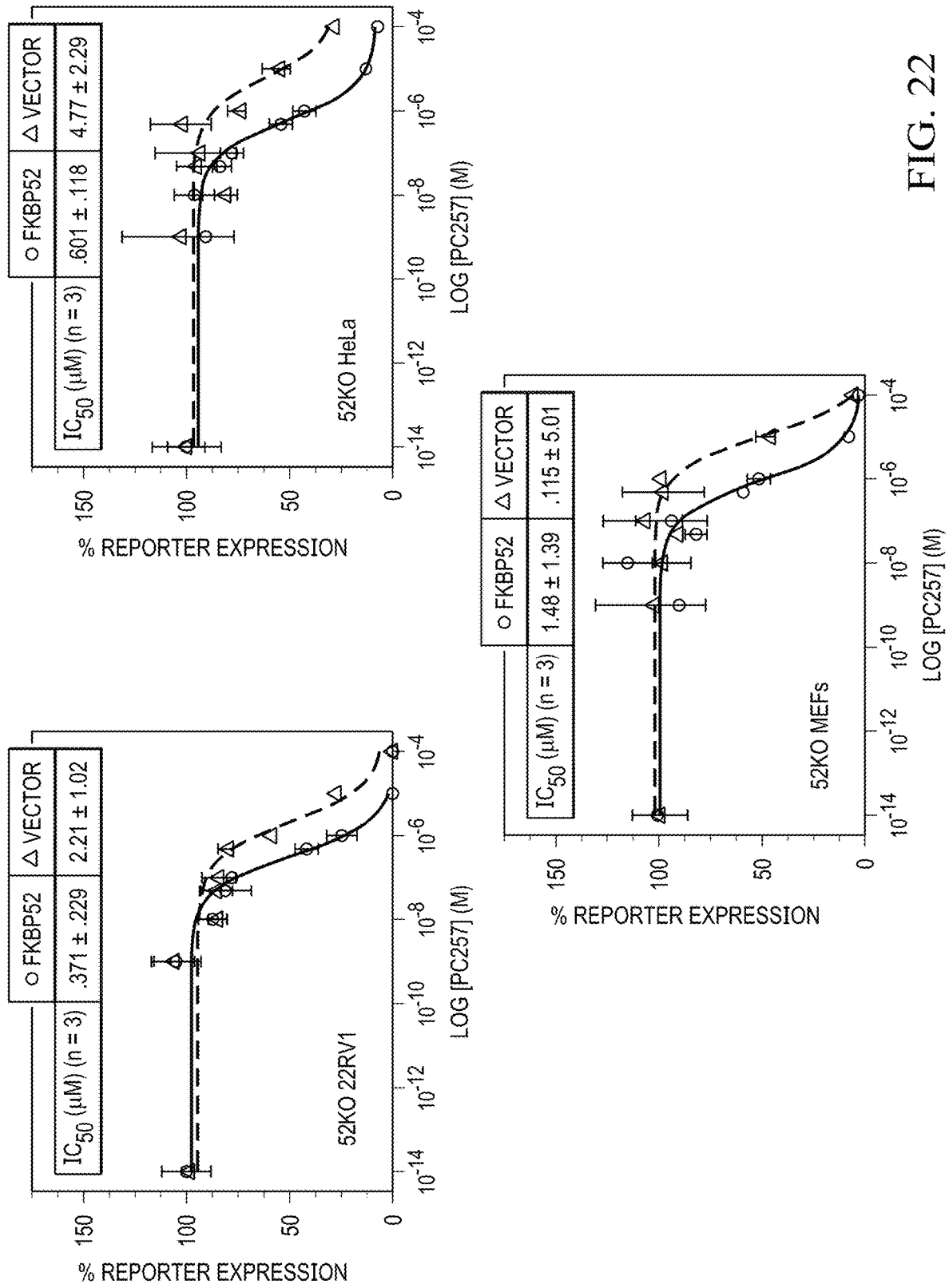
FIG. 22 depicts that PC257 preferentially targets FKBP52-regulated receptor activity in accordance with an illustrative embodiment.

Referring to FIG. 22, dihydrotestosterone (DHT)-induced, androgen receptor-dependent luciferase reporter gene expression was assessed in the presence of a range of PC257 concentrations in the presence or absence of exogenous FKBP52 expression in fkbp52-deficient 22Rv1, HeLa, and mouse embryonic fibroblast cells. The IC50 values are indicated. These data indicate that PC257 preferentially targets FKBP52-regulated AR activity with increased potency. PC257 is anticipated to target the PPIase pocket, a highly conserved enzymatic pocket among the FKBP family of proteins. Thus, it is likely that PC257 targets a variety of family members including FKBP51 (FKBPS), which has also been shown to regulate AR activity in some prostate cancer cell lines.

Figure 23A:
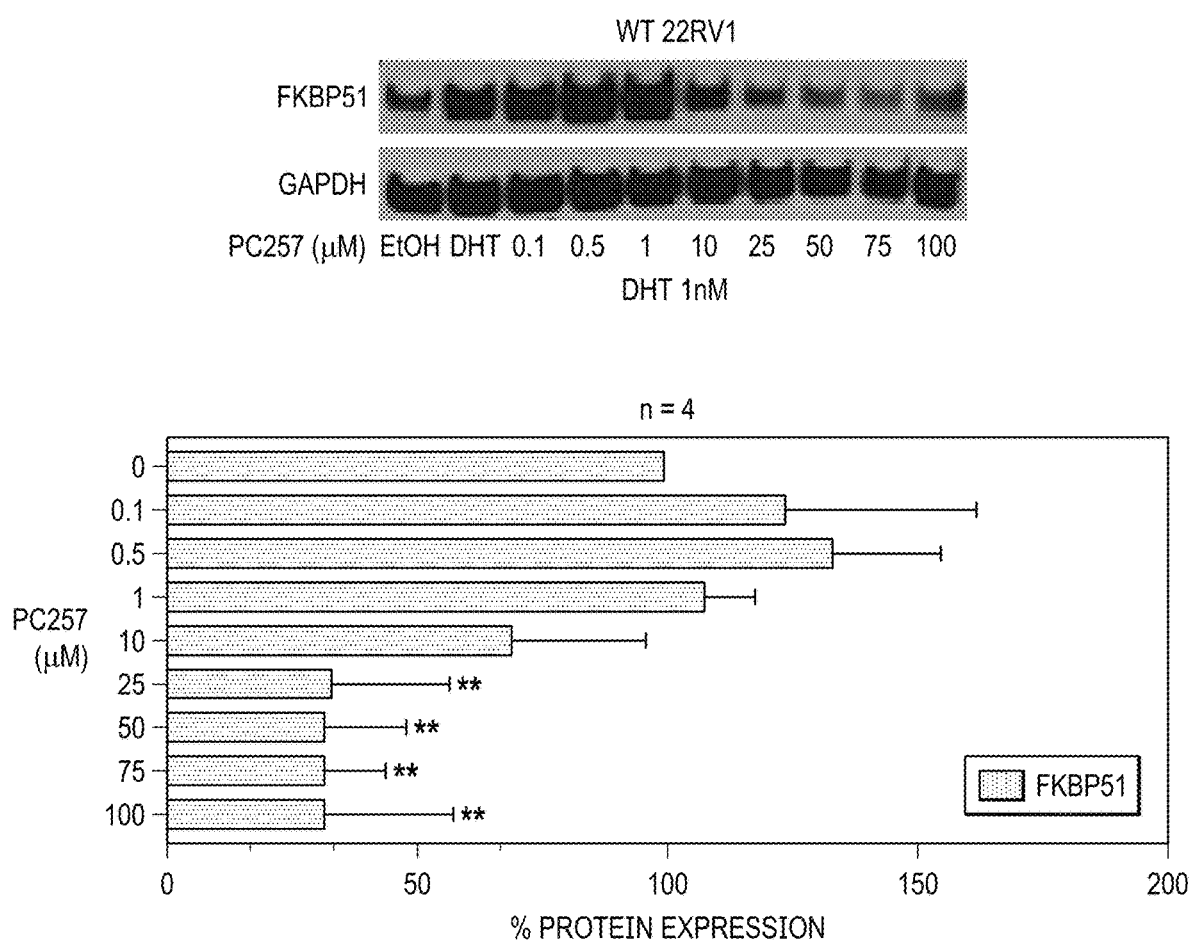
FIGS. 23A-23C depict that PC257 abrogates endogenous AR-dependent gene expression in accordance with an illustrative embodiment.
Figure 23B:
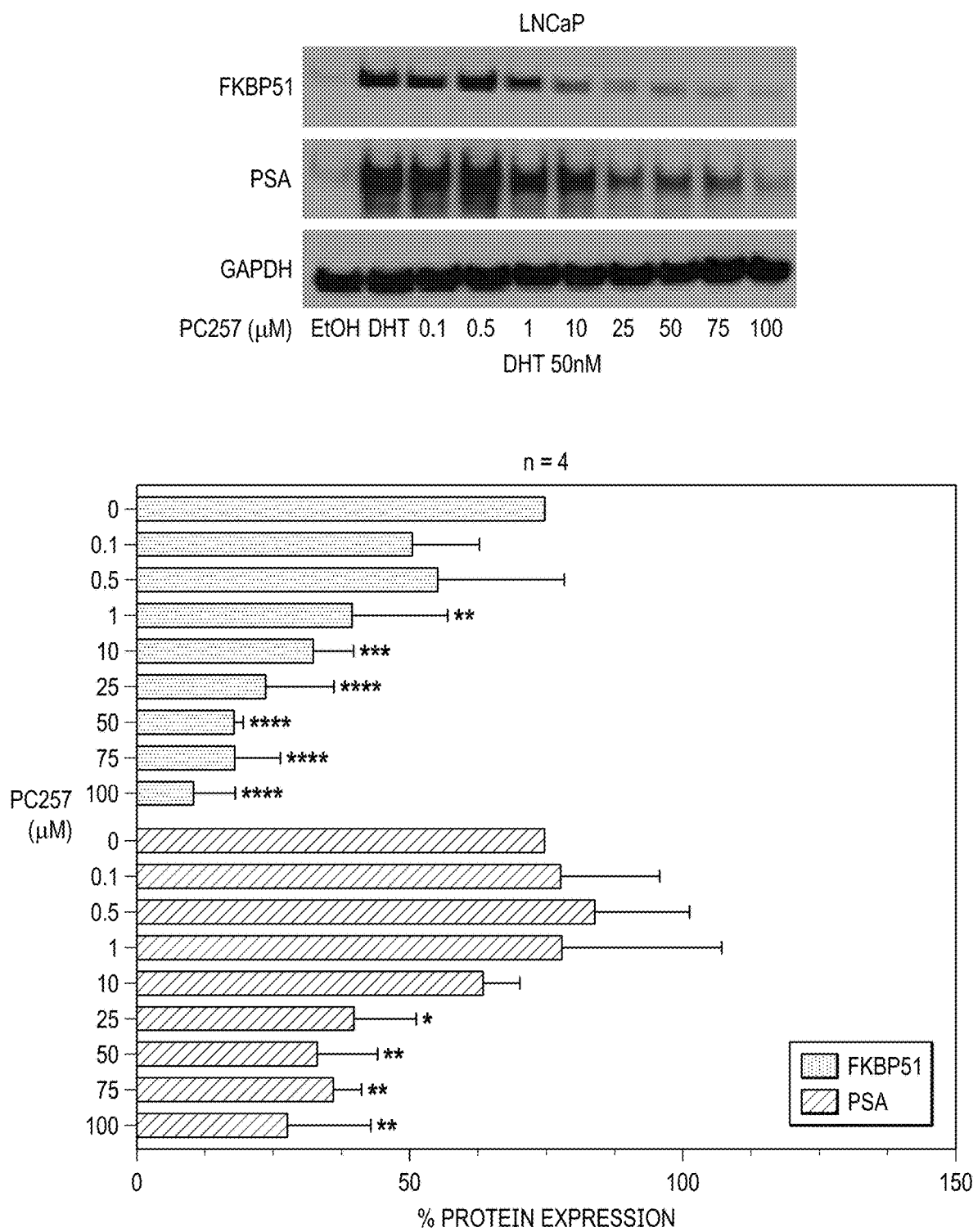
Figure 23C:
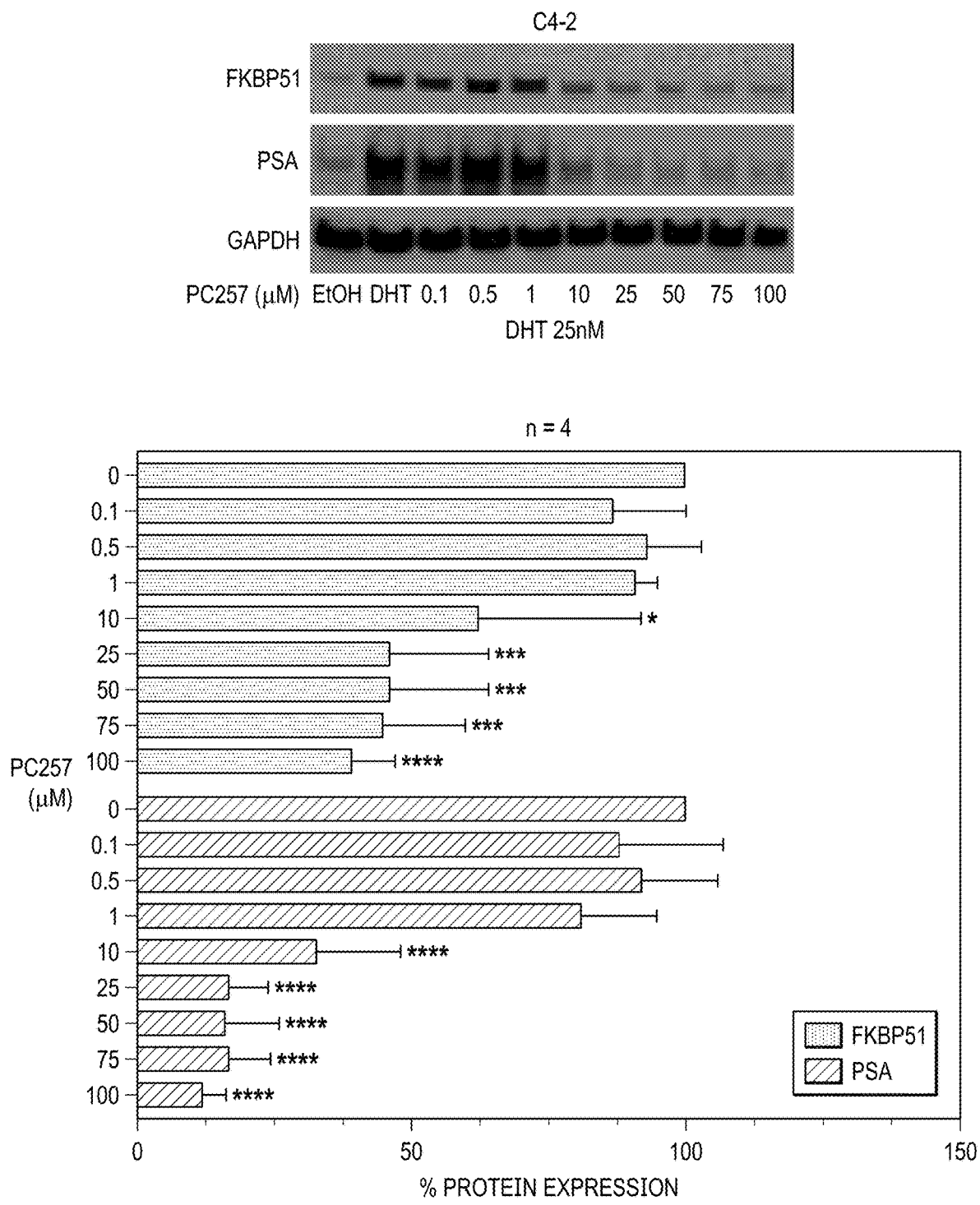

Referring to FIG. 23, hormone-dependent FKBP51 and/or PSA protein levels were assessed by Western blot and densitometry in the indicated cell lines in the presence of a range of PC257 concentrations. GAPDH was used as a loading control and the densitometry data were normalized to GAPDH.

Figure 24:
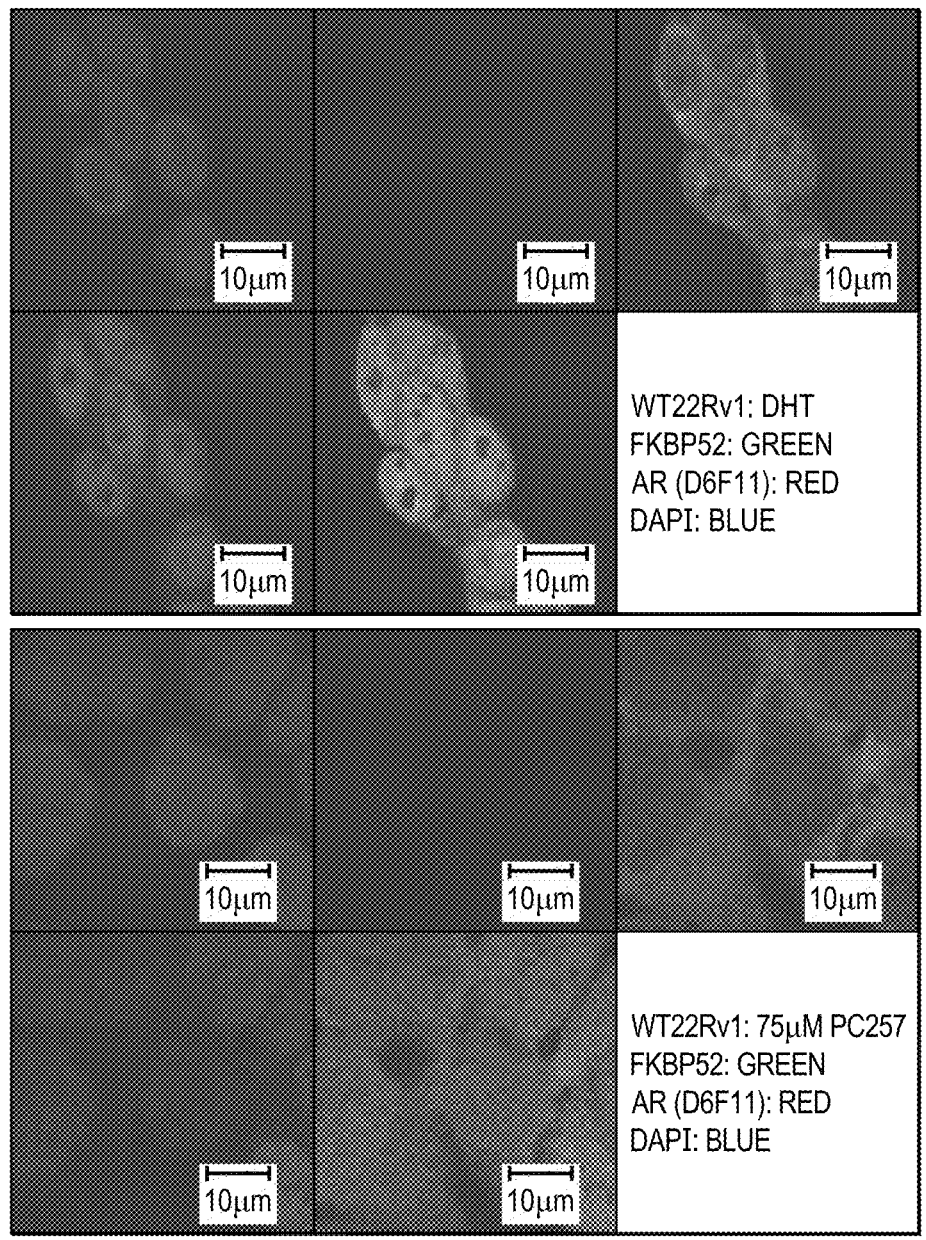
FIG. 24 depicts that PC257 Blocks Androgen-Dependent AR Nuclear Translocation in accordance with an illustrative embodiment.

Referring to FIG. 24, 22Rv1 prostate cancer cells were treated with or without 75 µM in the presence of hormone and AR and FKBP52 cellular localization was assessed by fluorescence microscopy. These data indicate that PC257 significantly inhibits AR nuclear translocation.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

1. World Health Organization (WHO). Cancer Mortality and Morbidity.
2. Gaali, S.; Kirschner, A.; Cuboni, S.; Hartmann, J.; Kozany, C.; Balsevich, G.; Namendorf, C.; Fernandez-Vizarra, P.; Sippel, C.; Zannas, A. S.; Draenert, R.; Binder, E. B.; Almeida, O. F. X.; Ruhter, G.; Uhr, M.; Schmidt, M. V.; Touma, C.; Bracher, A.; Hausch, F., Selective inhibitors of the FK506-binding protein 51 by induced fit. *Nature Chemical Biology* 2015, 11 (1), 33-+.
3. Hong, C. Q.; Li, T.; Zhang, F.; Wu, X.; Chen, X. P.; Cui, X. J.; Zhang, G. J.; Cui, Y. K., Elevated FKBP52 expression indicates a poor outcome in patients with breast cancer. *Oncology Letters* 2017, 14 (5), 5379-5385.
4. De Leon, J. T.; Iwai, A.; Feau, C.; Garcia, Y.; Balsiger, H. A.; Storer, C. L.; Suro, R. M.; Garza, K. M.; Lee, S.; Kim, Y. S.; Chen, Y.; Ning, Y. M.; Riggs, D. L.; Fletterick, R. J.; Guy, R. K.; Trepel, J. B.; Neckers, L. M.; Cox, M. B., Targeting the regulation of androgen receptor signaling by the heat shock protein 90 cochaperone FKBP52 in prostate cancer cells. *Proceedings of the National Academy of Sciences of the United States of America* 2011, 108 (29), 11878-11883.
5. Cox, M. B.; Storer, C. L.; Suh, J. H.; Chattopadhyay, A.; Fletterick, R.; Strom, A. M.; Webb, P., FKBP52 and beta-Catenin Directly Interact to Regulate Androgen Receptor Activity in Prostate Cancer Cells. *Endocrine Reviews* 2014, 35 (3).
6. Stope, M. B.; Burchardt, M., Re: Targeting the Regulation of Androgen Receptor Signaling by the Heat Shock Protein 90 Cochaperone FKBP52 in Prostate Cancer Cells. *European Urology* 2012, 62 (5), 931-932.
7. Xie, H.; Ekpenyong, O., Early development of GMC1, a novel molecule targeting FKBP52 for the treatment of hormone-refractory prostate cancer. *Cancer Research* 2017, 77.
8. Li, P. Y.; Ding, Y.; Wu, B. L.; Shu, C. L.; Shen, B. F.; Rao, Z. H., Structure of the N-terminal domain of human FKBP52. *Acta Crystallographica Section D-Biological Crystallography* 2003, 59, 16-22.
9. Bracher, A.; Kozany, C; Hahle, A.; Wild, P.; Zacharias, M.; Hausch, F., Crystal Structures of the Free and Ligand-Bound FK1-FK2 Domain Segment of FKBP52 Reveal a Flexible Inter-Domain Hinge. *Journal of Molecular Biology* 2013, 425 (22), 4134-4144.
10. Langer, T.; Hoffmann, R., Virtual screening an effective tool for lead structure discovery. *Current pharmaceutical design* 2001, 7 (7), 509-527.
11. Dey, S.; Ye, Q.; Sampalli, S., A machine learning based intrusion detection scheme for data fusion in mobile clouds involving heterogeneous client networks. *Information Fusion* 2019, 49, 205-215.
12. Guo, H. Q.; Wang, Y. X.; He, Q. X.; Zhang, Y. P.; Hu, Y.; Wang, Y. Q.; Lin, Z. H., In silico rational design and virtual screening of antioxidant tripeptides based on 3D-QSAR modeling. *Journal of Molecular Structure* 2019, 1193, 223-230.
13. Cavasotto, C. N.; Adler, N. S.; Aucar, M. G., Quantum Chemical Approaches in Structure-Based Virtual Screening and Lead Optimization. *Frontiers in Chemistry* 2018, 6.
14. Chatterjee, D.; Kaur, G.; Muradia, S.; Singh, B.; Agrewala, J. N., ImmtorLig_DB: repertoire of virtually screened small molecules against immune receptors to bolster host immunity. *Scientific Reports* 2019, 9.
15. Shahbaaz, M.; Nkaule, A.; Christoffels, A., Designing novel possible kinase inhibitor derivatives as therapeutics against *Mycobacterium tuberculosis*: An in silico study. *Scientific Reports* 2019, 9.
16. Zhou, W. F.; Duan, M. J.; Fu, W. T.; Pang, J. P.; Tang, Q.; Sun, H. Y.; Xu, L.; Chang, S.; Li, D.; Hou, T. J., Discovery of Novel Androgen Receptor Ligands by Structure-based Virtual Screening and Bioassays. *Genomics Proteomics & Bioinformatics* 2019, 16 (6), 416-427.
17. Spena, C. R.; De Stefano, L.; Poli, G.; Granchi, C.; El Boustani, M.; Ecca, F.; Grassi, G.; Grassi, M.; Canzonieri, V.; Giordano, A.; Tuccinardi, T.; Caligiuri, I.; Rizzolio, F., Virtual screening identifies a PIN1 inhibitor with possible antiovarian cancer effects. *Journal of Cellular Physiology* 2019, 234 (9), 15708-15716.
18. Li, H. F.; Ban, F. Q.; Dalal, K.; Leblanc, E.; Frewin, K.; Ma, D.; Adomat, H.; Rennie, P. S.; Cherkasov, A., Discovery of Small-Molecule Inhibitors Selectively Targeting the DNA-Binding Domain of the Human Androgen Receptor. *J Med Chem* 2014, 57 (15), 6458-6467.
19. Li, H.; Hassona, M. D. H.; Lack, N. A.; Axerio-Cilies, P.; Leblanc, E.; Tavassoli, P.; Kanaan, N.; Frewin, K.; Singh, K.; Adomat, H.; Boehm, K. J.; Prinz, H.; Guns, E. T.; Rennie, P. S.; Cherkasov, A., Characterization of a New Class of Androgen Receptor Antagonists with Potential Therapeutic Application in Advanced Prostate Cancer. *Molecular Cancer Therapeutics* 2013, 12 (11), 2425-2435.
20. Irwin, J. J.; Sterling, T.; Mysinger, M. M.; Bolstad, E. S.; Coleman, R. G., ZINC: A Free Tool to Discover Chemistry for Biology. *Journal of Chemical Information and Modeling* 2012, 52 (7), 1757-1768.

21. Zhang, J.; Chai, H. T., Recent In Silico Research in High-Throughput Drug Discovery and Molecular Biochemistry. *Current Topics in Medicinal Chemistry* 2019, 19 (2), 103-104.
22. Kumar, A.; Rathi, E.; Kini, S. G., E-pharmacophore modelling, virtual screening, molecular dynamics simulations and in-silico ADME analysis for identification of potential E6 inhibitors against cervical cancer. *Journal of Molecular Structure* 2019, 1189, 299-306.
23. Feng, K. R.; Ren, Y. J.; Li, R., Combined pharmacophore-guided 3D-QSAR, molecular docking and molecular dynamics studies for evodiamine analogs as DNA topoisomerase I inhibitors. *Journal of the Taiwan Institute of Chemical Engineers* 2017, 78, 81-95.
24. Lionta, E.; Spyrou, G.; Vassilatis, D. K.; Cournia, Z., Structure-Based Virtual Screening for Drug Discovery: Principles, Applications and Recent Advances. *Current Topics in Medicinal Chemistry* 2014, 14 (16), 1923-1938.
25. Kaushik, A. C.; Kumar, A.; Bharadwaj, S.; Chaudhary, R.; Sahi, S., Ligand-Based Approach for In-silico Drug Designing. *Bioinformatics Techniques for Drug Discovery: Applications for Complex Diseases* 2018, 11-19.
26. Mandi, M.; Ahmad, R.; Ismail, R.; Ieee In *Similarity Search Techniques in Exploratory Search: A Review*, IEEE-Region-10 Conference (IEEE TENCON), IEEE Reg 10, SOUTH KOREA, October 28-31; Ieee: IEEE Reg 10, SOUTH KOREA, 2018; pp 2193-2198.
27. Li, S. R.; Fan, J. L.; Peng, C. K.; Chang, Y. Q.; Guo, L. X.; Hou, J. S.; Huang, M. Q.; Wu, B. Y.; Zheng, J. X.; Lin, L. X.; Xiao, G. K.; Chen, W. M.; Liao, G. C.; Guo, J. L.; Sun, P. H., New molecular insights into the tyrosyl-tRNA synthase inhibitors: CoMFA, CoMSIA analyses and molecular docking studies. *Scientific Reports* 2017, 7.
28. Capecchi, A.; Awale, M.; Probst, D.; Reymond, J. L., PubChem and ChEMBL beyond Lipinski. *Molecular Informatics* 2019, 38 (5).
29. Nandy, A.; Roy, K.; Saha, A., Exploring molecular fingerprints of selective PPAR delta agonists through comparative and validated chemometric techniques. *Sar and Qsar in Environmental Research* 2015, 26 (5), 363-382.
30. Xie, H. D.; Qiu, K. X.; Xie, X. G., Pharmacophore modeling, virtual screening, and 3D-QSAR studies on a series of non-steroidal aromatase inhibitors. *Medicinal Chemistry Research* 2015, 24 (5), 1901-1915.
31. Kumar, V.; Krishna, S.; Siddiqi, M. I., Virtual screening strategies: Recent advances in the identification and design of anti-cancer agents. *Methods* 2015, 71, 64-70.
32. Awale, M.; Visini, R.; Probst, D.; Arus-Pous, J.; Reymond, J. L., Chemical Space: Big Data Challenge for Molecular Diversity. *Chimia* 2017, 71 (10), 661-666.
33. Cherkasov, A.; Muratov, E. N.; Fourches, D.; Varnek, A.; Baskin, II; Cronin, M.; Dearden, J.; Gramatica, P.; Martin, Y. C.; Todeschini, R.; Consonni, V.; Kuz'min, V. E.; Cramer, R.; Benigni, R.; Yang, C. H.; Rathman, J.; Terfloth, L.; Gasteiger, J.; Richard, A.; Tropsha, A., QSAR Modeling: Where Have You Been? Where Are You Going To? *Journal of Medicinal Chemistry* 2014, 57 (12), 4977-5010.
34. Araujo, S. C.; Maltarollo, V. G.; Honorio, K. M., Computational studies of TGF-beta RI (ALK-5) inhibitors: Analysis of the binding interactions between ligand-receptor using 2D and 3D techniques. *European Journal of Pharmaceutical Sciences* 2013, 49 (4), 542-549.
35. Maltarollo, V. G.; Silva, D. C.; Honorio, K. M., Advanced QSAR Studies on PPAR delta Ligands Related to Metabolic Diseases. *Journal of the Brazilian Chemical Society* 2012, 23 (1), 85-U421.
36. de Angelo, R.; Almeida, M.; de Paula, H.; Honorio, K., Studies on the Dual Activity of EGFR and HER-2 Inhibitors Using Structure-Based Drug Design Techniques. *International journal of molecular sciences* 2018, 19 (12), 3728.
37. Cramer, R. D.; Patterson, D. E.; Bunce, J. D., Comparative molecular field analysis (CoMFA). 1. Effect of shape on binding of steroids to carrier proteins. *Journal of the American Chemical Society* 1988, 110 (18), 5959-5967.
38. Kubinyi, H.; Folkers, G.; Martin, Y. C., *3D QSAR in Drug Design: Volume 2: Ligand-Protein Interactions and Molecular Similarity*. Springer: 1998; Vol. 2.
39. Llanos, E.; Leal, W.; Restrepo, G.; Stadler, P., Computational approach to the history of chemical reactivity: Exploring Reaxys database. *Abstracts of Papers of the American Chemical Society* 2017, 254.
40. O'Boyle, N.; Sayle, R.; Bolton, E., PubChem as a biologics database. *Abstracts of Papers of the American Chemical Society* 2017, 254.
41. Saikia, S.; Bordoloi, M., Molecular Docking: Challenges, Advances and its Use in Drug Discovery Perspective. *Current Drug Targets* 2019, 20 (5), 501-521.
42. Leal, F. D.; da Silva Lima, C. H.; de Alencastro, R. B.; Castro, H. C.; Rodrigues, C. R.; Albuquerque, M. G., Hologram QSAR Models of a Series of 6-Arylquinazolin-4-Amine Inhibitors of a New Alzheimer's Disease Target: Dual Specificity Tyrosine-Phosphorylation-Regulated Kinase-1A Enzyme. *International Journal of Molecular Sciences* 2015, 16 (3), 5235-5253.
43. Zhang, G. M.; Ren, Y. J., Molecular Modeling and Design Studies of Purine Derivatives as Novel CDK2 Inhibitors. *Molecules* 2018, 23 (11).
44. Alam, S.; Khan, F., 3D-QSAR, Docking, ADME/Tox studies on Flavone analogs reveal anticancer activity through Tankyrase inhibition. *Scientific Reports* 2019, 9.
45. Anderson, A. C., The process of structure-based drug design. *Chemistry & biology* 2003, 10 (9), 787-797.
46. Salum, L. B.; Polikarpov, I.; Andricopulo, A. D., Structure-Based Approach for the Study of Estrogen Receptor Binding Affinity and Subtype Selectivity. *Journal of Chemical Information and Modeling* 2008, 48 (11), 2243-2253.
47. Kubinyi, H., QSAR and 3D QSAR in drug design Part 2: applications and problems. *Drug Discovery Today* 1997, 2 (12), 538-546.
48. Ou-Yang, S. S.; Lu, J. Y.; Kong, X. Q.; Liang, Z. J.; Luo, C.; Jiang, H. L., Computational drug discovery. *Acta Pharmacologica Sinica* 2012, 33 (9), 1131-1140.
49. Cheng, T. J.; Li, Q. L.; Zhou, Z. G.; Wang, Y. L.; Bryant, S. H., Structure-Based Virtual Screening for Drug Discovery: a Problem-Centric Review. *Aaps Journal* 2012, 14 (1), 133-141.
50. O'Boyle, N. M.; Liebeschuetz, J. W.; Cole, J. C., Testing Assumptions and Hypotheses for Rescoring Success in Protein-Ligand Docking. *Journal of Chemical Information and Modeling* 2009, 49 (8), 1871-1878.
51. Svensson, F.; Karlen, A.; Skold, C., Virtual Screening Data Fusion Using Both Structure- and Ligand-Based Methods. *Journal of Chemical Information and Modeling* 2012, 52 (1), 225-232.
52. Warren, G. L.; Do, T. D.; Kelley, B. P.; Nicholls, A.; Warren, S. D., Essential considerations for using protein-ligand structures in drug discovery. *Drug Discovery Today* 2012, 17 (23-24), 1270-1281.

53. Gopalakrishnan, R.; Kozany, C.; Wang, Y. S.; Schneider, S.; Hoogeland, B.; Bracher, A.; Hausch, F., Exploration of Pipecolate Sulfonamides as Binders of the FK506-Binding Proteins 51 and 52. *Journal of Medicinal Chemistry* 2012, 55 (9), 4123-4131.

54. Bonomo, S.; Hansen, C. H.; Petrunak, E. M.; Scott, E. E.; Styrishave, B.; Jorgensen, F. S.; Olsen, L., Promising Tools in Prostate Cancer Research: Selective Non-Steroidal Cytochrome P450 17A1 Inhibitors. *Scientific Reports* 2016, 6.

55. Nunes, C. A.; Freitas, M. P.; Pinheiro, A. C. M.; Bastos, S. C., Chemoface: a Novel Free User-Friendly Interface for Chemometrics. *Journal of the Brazilian Chemical Society* 2012, 23 (11), 2003-2010.

56. Vora, J.; Patel, S.; Sinha, S.; Sharma, S.; Srivastava, A.; Chhabria, M.; Shrivastava, N., Structure based virtual screening, 3D-QSAR, molecular dynamics and ADMET studies for selection of natural inhibitors against structural and non-structural targets of Chikungunya. *Journal of Biomolecular Structure & Dynamics* 2019, 37 (12), 3150-3161.

57. Gaudio, A. C.; Zandonade, E., Proposition, validation and analysis of QSAR models. *Quìmica Nova* 2001, 24 (5), 658-671.

58. Chirico, N.; Gramatica, P., Real External Predictivity of QSAR Models: How To Evaluate It? Comparison of Different Validation Criteria and Proposal of Using the Concordance Correlation Coefficient. *Journal of Chemical Information and Modeling* 2011, 51 (9), 2320-2335.

59. Caballero, J., 3D-QSAR (CoMFA and CoMSIA) and pharmacophore (GALAHAD) studies on the differential inhibition of aldose reductase by flavonoid compounds. *Journal of Molecular Graphics & Modelling* 2010, 29 (3), 363-371.

60. Gramatica, P., Principles of QSAR models validation: internal and external. *QSAR & combinatorial science* 2007, 26 (5), 694-701.

61. Netzeva, T. I.; Worth, A. P.; Aldenberg, T.; Benigni, R.; Cronin, M. T. D.; Gramatica, P.; Jaworska, J. S.; Kahn, S.; Klopman, G.; Marchant, C. A.; Myatt, G.; Nikolova-Jeliazkova, N.; Patlewicz, G. Y.; Perkins, R.; Roberts, D. W.; Schultz, T. W.; Stanton, D. T.; van de Sandt, J. J. M.; Tong, W. D.; Veith, G.; Yang, C. H., Current status of methods for defining the applicability domain of (quantitative) structure-activity relationships—The report and recommendations of ECVAM Workshop 52. *Atla-Alternatives to Laboratory Animals* 2005, 33 (2), 155-173.

62. Pick, A.; Muller, H.; Mayer, R.; Haenisch, B.; Pajeva, I. K.; Weigt, M.; Bonisch, H.; Muller, C. E.; Wiese, M., Structure-activity relationships of flavonoids as inhibitors of breast cancer resistance protein (BCRP). *Bioorg. Med. Chem.* 2011, 19 (6), 2090-2102.

63. Fang, Y. J.; Lu, Y. L.; Zang, X. X.; Wu, T.; Qi, X. J.; Pan, S. Y.; Xu, X. Y., 3D-QSAR and docking studies of flavonoids as potent *Escherichia coli* inhibitors. *Scientific Reports* 2016, 6.

64. Zhu, X. X.; Li, Y.; Zhang, X. R.; Yuan, L.; Luo, P. H.; Gao, X.; Tan, Z. S., Identifying Potential Dual Inhibitory Candidates for Non-Small Cell Lung Cancer through Molecular Docking, 3D-QSAR Pharmacophore-based Virtual Screening, Comparative Molecular Field and Similarity Indices Analysis Modeling. *Journal of Pharmaceutical Research International* 2018, 24 (3).

65. Tan, Z.; Chen, L.; Zhang, S. X., Comprehensive Modeling and Discovery of Mebendazole as a Novel TRAF2- and NCK-interacting Kinase Inhibitor. *Scientific Reports* 2016, 6.

66. De Benedetti, P. G.; Fanelli, F., Computational quantum chemistry and adaptive ligand modeling in mechanistic QSAR. *Drug Discovery Today* 2010, 15 (19-20), 859-866.

67. Yap, C. W., PaDEL-Descriptor: An Open Source Software to Calculate Molecular Descriptors and Fingerprints. *Journal of Computational Chemistry* 2011, 32 (7), 1466-1474.

68. Sybyl 8.1, Tripos Inc.

69. Yao, K.; Liu, P. Y.; Liu, H. P.; Wei, Q. Y.; Yang, J.; Cao, P.; Lai, Y. S., 3D-QSAR, molecular docking and molecular dynamics simulations study of 3-pyrimidin-4-yl-oxazolidin-2-one derivatives to explore the structure requirements of mutant IDH1 inhibitors. *Journal of Molecular Structure* 2019, 1189, 187-202.

70. Zhang, C. Z.; Zhang, H. J.; Huang, L. N. S.; Zhu, S. Y.; Xu, Y.; Zhang, X. Q.; Schooley, R. T.; Yang, X. H.; Huang, Z. W.; An, J., Virtual Screening, Biological Evaluation, and 3D-QSAR Studies of New HIV-1 Entry Inhibitors That Function via the CD4 Primary Receptor. *Molecules* 2018, 23 (11).

71. Tong, J.; Jiang, G.; Li, L.; Li, Y., Molecular Virtual Screening Studies of Herbicidal Sulfonylurea Analogues Using Molecular Docking and Topomer CoMFA Research. *Journal of Structural Chemistry* 2019, 60 (2), 210-218.

72. Huang, L.; Zhang, X. R.; Luo, P. H.; Yuan, L.; Zhou, X. Z.; Gao, X.; Li, L. S., QSAR Pharmacophore-based Virtual Screening, CoMFA and CoMSIA Modeling and Molecular Docking towards Identifying Lead Compounds for Breast Cancer Protease Inhibitors. *British Journal of Pharmaceutical Research* 2017, 20 (1).

What is claimed is:

1. A method of inhibiting hormone receptor activation, comprising administering to a subject in need of hormone receptor inhibition a compound having a chemical structure of Formula I

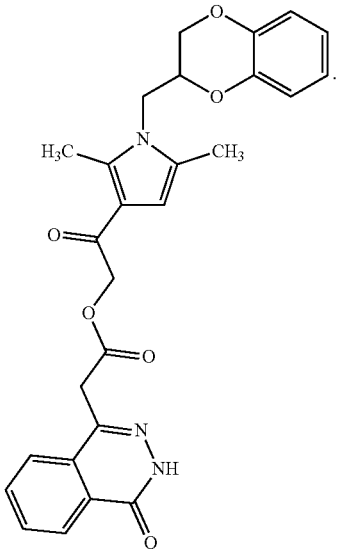

Formula I

2. The method of claim 1, wherein the hormone receptor is the androgen receptor.

3. The method of claim 1, wherein the subject has hyperplasia or neoplasia.

4. The method of claim 1, wherein the subject has prostate cancer or breast cancer.

5. The method of claim 1, further comprising administering chemotherapy or radiation treatments.

6. A method of treating prostate cancer or breast cancer comprising administering to a subject having prostate cancer or breast cancer a compound having a chemical structure of Formula I

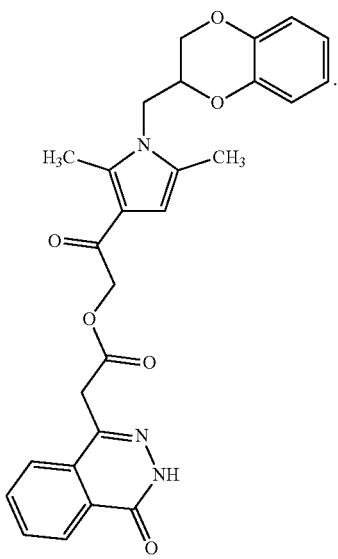

Formula I

7. The method of claim 5, further comprising administering chemotherapy or radiation treatments.

8. A method of inhibiting hormone receptor activation, comprising
administering to a subject in need of hormone receptor inhibition a compound having a chemical structure of Formula I

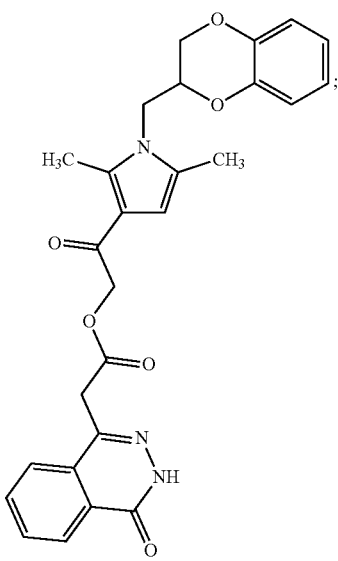

Formula I and
administering chemotherapy treatment.

9. The method of claim 8, wherein the hormone receptor is the androgen receptor.

10. The method of claim 8, wherein the subject has hyperplasia.

11. The method of claim 8, wherein the subject has neoplasia.

12. The method of claim 8, wherein the subject has prostate cancer.

13. The method of claim 8, wherein the subject has breast cancer.

14. A method of inhibiting hormone receptor activation, comprising
administering to a subject in need of hormone receptor inhibition a compound having a chemical structure of Formula I

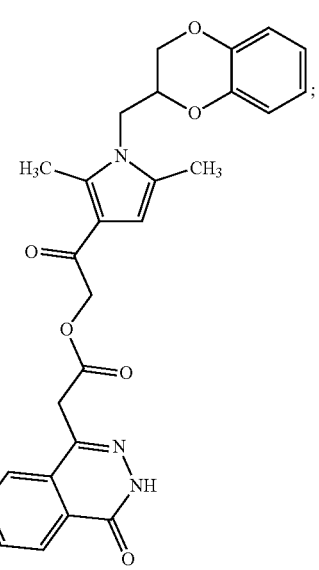

Formula I and
administering radiation treatment.

15. The method of claim 14, wherein the hormone receptor is the androgen receptor.

16. The method of claim 14, wherein the subject has hyperplasia.

17. The method of claim 14, wherein the subject has neoplasia.

18. The method of claim 14, wherein the subject has prostate cancer.

19. The method of claim 14, wherein the subject has breast cancer.

20. A method of treating prostate cancer or breast cancer comprising
administering to a subject having prostate cancer or breast cancer a compound having a chemical structure of Formula I Formula I
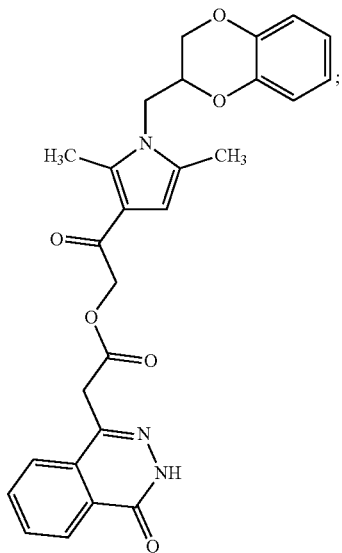
and
administering chemotherapy treatment.
21. A method of treating prostate cancer or breast cancer comprising
administering to a subject having prostate cancer or breast cancer a compound having a chemical structure of Formula I
Formula I
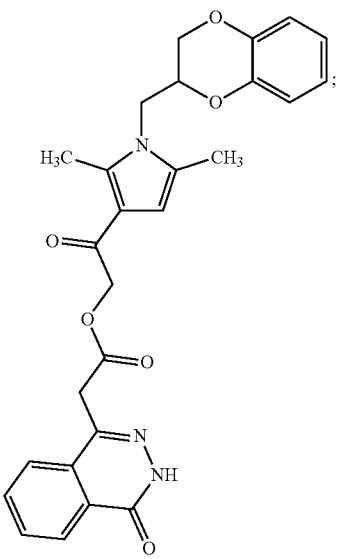
and
administering radiation treatment.
* * * * *

UNITED STATES PATENT AND TRADEMARK OFFICE
CERTIFICATE OF CORRECTION

PATENT NO. : 11,878,961 B2
APPLICATION NO. : 17/153340
DATED : January 23, 2024
INVENTOR(S) : Marc Cox, Artem Cherkasov and Fuqiang Ban Page 1 of 1

It is certified that error appears in the above-identified patent and that said Letters Patent is hereby corrected as shown below:

In the Specification

Replace Column 1, Lines 12-15 with the following:
STATEMENT OF GOVERNMENT INTEREST
This invention was made with government support under W81XWH-17-1-0436 and W81XWH-17-1-0435 awarded by the Defense Health Agency, Medical Research and Development Branch. The government has certain rights in the invention.

Signed and Sealed this
Thirtieth Day of July, 2024

Katherine Kelly Vidal
*Director of the United States Patent and Trademark Office*